US007932055B2

(12) United States Patent
Spee et al.

(10) Patent No.: US 7,932,055 B2
(45) Date of Patent: Apr. 26, 2011

(54) SOLUBLE HETERODIMERIC CD94/NKG2 RECEPTORS FUSION PROTEINS

(75) Inventors: Petrus Johannes Louis Spee, Allerød (DK); Søren Berg Padkær, Værløse (DK); Birgitte Nissen Friedrichsen, Gentofte (DK); Inga Sig Nielsen Nørby, Birkerød (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 12/305,678

(22) PCT Filed: Jun. 22, 2007

(86) PCT No.: PCT/EP2007/056276
§ 371 (c)(1),
(2), (4) Date: Jun. 24, 2009

(87) PCT Pub. No.: WO2007/147898
PCT Pub. Date: Dec. 27, 2007

(65) Prior Publication Data
US 2009/0281035 A1 Nov. 12, 2009

Related U.S. Application Data

(60) Provisional application No. 60/817,116, filed on Jun. 28, 2006.

(30) Foreign Application Priority Data

Jun. 22, 2006 (EP) .................................... 06115901

(51) Int. Cl.
C07K 14/725 (2006.01)
C12P 21/00 (2006.01)
(52) U.S. Cl. .................... 435/69.7; 530/350; 530/387.3; 530/387.9; 530/388.75; 530/388.85; 424/178.1; 424/192.1
(58) Field of Classification Search .................. None
See application file for complete search history.

(56) References Cited

U.S. PATENT DOCUMENTS

| | | | |
|---|---|---|---|
| 6,018,026 | A | 1/2000 | Sledziewski et al. |
| 6,238,890 | B1 | 5/2001 | Boime |
| 6,262,244 | B1 | 7/2001 | Houchins et al. |
| 6,833,441 | B2 | 12/2004 | Wang et al. |
| 2003/0078385 | A1 | 4/2003 | Arathoon et al. |
| 2003/0195338 | A1 | 10/2003 | Chung et al. |
| 2004/0072256 | A1 | 4/2004 | Mendelboim et al. |
| 2004/0138417 | A1 | 7/2004 | Fitzpatrick et al. |

FOREIGN PATENT DOCUMENTS

| | | |
|---|---|---|
| WO | WO 92/06204 | 4/1992 |
| WO | WO 95/33057 | 12/1995 |
| WO | WO 9734631 | 9/1997 |
| WO | WO 98/50431 | 11/1998 |
| WO | WO 99/28747 | 6/1999 |
| WO | WO 9929732 | 6/1999 |
| WO | WO 99/37772 | 7/1999 |
| WO | WO 0158957 | 8/2001 |
| WO | WO 02/03237 | 1/2002 |
| WO | WO 02/08272 | 1/2002 |
| WO | WO 02/12345 | 2/2002 |
| WO | WO 02/22153 | 3/2002 |
| WO | WO 02/101006 | 12/2002 |
| WO | WO 03/012069 | 2/2003 |

OTHER PUBLICATIONS

Gunturi et al., Immunologic Research 30(1):29-34.*
Hayer, Silvia et al, Natural Immunity, 1998, vol. 16, No. 2-3, p. 78.
Brooks, Andrews G. et al, Journal of Immunology, 1999, vol. 162, No. 1, pp. 305-313.
Vales-Gomez, M. et al, Embo Journal, 1999, vol. 18, No. 15, pp. 4250-4260.
Boyington et al., "Structure of CD94 Reveals a Novel C-Type Lectin Fold: Implications for the NK Cell-Associated CD94/NKG2 Receptors," Immunity, 1999, vol. 10, No. 1, pp. 75-82.
Chang et al., "Molecular Characterization of Human CD94: A Type II Membrane Glycoprotein Related to the C-Type Lectin Superfamily," European Journal of Immunology, 1995, vol. 25, pp. 2433-2437.
Clements et al., "The Production, Purification and Crystallization of a Soluble Heterodimeric Form of a Highly Selected T-Cell Receptor in Its Unliganded and Liganded State," Acta Crystallographica, 2002, vol. 58, pp. 2131-2134.
Ding et al., "Direct Binding of Purified HLA Class I Antigens by Soluble NKG2/CD94 C-Type Lectins From Natural Killer Cells," Scandinavian Journal of Immunology, 1999, vol. 49, pp. 459-465.
Farag et al., "New Directions in Natural Killer Cell-Based Immunotherapy of Human Cancer," Expert Opinion on Biological Therapy, 2003, vol. 3, pp. 237-250.
Hendsch et al., "Preferential Heterodimer Formation Via Undercompensated Electrostatic Interactions," Journal of the American Chemical Society, 2001, vol. 123, pp. 1264-1265.
Kabat et al., "Role That Each NKG2A Immunoreceptor Tyrosine-Based Inhibitory Motif Plays in Mediating the Human CD94/NKG2A Inhibitory Signal" Journal of Immunology, 2002, vol. 169, pp. 1948-1958.
Kaiser et al., "Interactions Between NKG2X Immunoreceptors and HLA-E Ligands Display Overlapping Affinities and Thermodynamics1," Journal of Immunology, 2005, vol. 174, pp. 2878-2884.
Kim et al., "Heterodimeric CD3EY Extracellular Domain Fragments: Production, Purification and Structural Analysis1," Journal of Molecular Biology, 2000, vol. 302, pp. 899-916.
Kontermann et al., "Recombinant Bispecific Antibodies for Cancer Therapy," Acta Pharmacologicasinica, 2005, vol. 26, pp. 1-9.
Laugel et al., "Design of Soluble Recombinant T Cell Receptors for Antigen Targeting and T Cell Inhibition," Journal of Biological Chemistry, 2005, vol. 280, pp. 1882-1892.

(Continued)

Primary Examiner — Lorraine Spector
(74) Attorney, Agent, or Firm — Teresa Chen

(57) ABSTRACT

Soluble versions of heterodimeric receptors, e.g., CD94/NKG2 receptors, and methods of producing and using such constructs, are described. The constructs comprise soluble fragments of, each receptor monomer, and some constructs further comprise at least one immunoglobulin Fc domain. Exemplary constructs are those wherein (1) each soluble fragment is linked to an immunoglobulin Fc domain, which are then allowed to dimerize, (2) each soluble fragment is linked to an immunoglobulin Fc domain mutated to promote forced dimerization with the correct counterpart, and (3) single-chain constructs where the monomeric receptor fragments are linked, and the C-terminal fragment is linked to an Fc domain.

20 Claims, 27 Drawing Sheets

OTHER PUBLICATIONS

Le Drean et al., "Inhibition of Antigen-Induced T Cell Response and Antibody-Induced NK Cell Cytotoxicity by NKG2A: Association of NKG2A With SHP-1 and SHP-2 Protein-Tyrosine Phosphatases," European Journal of Immunology, 1998, vol. 28, pp. 264-276.

Malmberg et al., "IFN-Y Protects Short-Term Ovarian Carcinoma Cell Lines From CTL Lysis Via a CD94/NKG2A-Dependent Mechanism," Journal of Clinical Investigation, 2002, vol. 110, pp. 1515-1523.

Marvin et al., "Recombinant Approaches to IGG-Like. Bispecific Antibodies," Acta Pharmacologicasinica, 2005, vol. 26, No. 6, pp. 649-658.

McPhee et al., "Engineering Human Immunodeficiency Virus 1 Protease Heterodimers as Macromolecular Inhibitors of Viral Maturation," Proceedings of the National Academy of Sciences of the USA, 1996, vol. 93, pp. 11477-11481.

Nohaile et al., "Altering Dimerization Specificity by Changes in Surface Electrostatics," Proceedings of the National Academy of Sciences of the USA, 2001, vol. 98, No. 6, pp. 3109-3114.

Ridgway et al., "Knobs-Into-Holes' Engineering of Antibody CH3 Domains for Heavy Chain Heterodimerization," Protein Engineering, 1996, vol. 9, No. 7, pp. 617-621.

Sal-Man et al., "Arginine Mutations Within a Transmembrane Domain of TAR, an *Escherichia coli* Aspartate Receptor, Can Drive Homodimer Dissociation and Heterodimer Association In Vivo," Biochemical Journal, 2005, vol. 385, pp. 29-36.

Sanni et al., "Exclusion of Lipid Rafts and Decreased Mobility of CD94/NKG2A Receptors at The Inhibitory NK Cell Synapse," Molecular Biology of the Cell, 2004, vol. 15, No. 7, pp. 3210-3223.

Speiser et al., "In Vivo Expression of Natural Killer Cell Inhibitory Receptors by Human Melanoma Specific Cytolytic T Lymphocytes," Journal of Experimental Medicine, 1999, vol. 190, No. 6, pp. 775-782.

Wu et al., "Solution Assembly of the Pseudo-High Affinity and Intermediate Affinity Interleukin-2 Receptor Complexes," Protein Science, 1999, vol. 8, pp. 482-489.

Zhu et al., "Remodeling Domain Interfaces to Enhance Heterodimer Formation," Protein Science, 1997, vol. 6, pp. 781-788.

\* cited by examiner

```
         1         2         3         4         5         6
123456789012345678901234567890123456789012345678901234567890
ASTKGPSVFPLAPSSKSTSGGTAALGCLVKDYFPEPVTVSWNSGALTSGVHTFPAVLQSS KM
ASTKGPSVFPLAPSSKSTSGGTAALGCLVKDYFPEPVTVSWNSGALTSGVHTFPAVLQSS GM 7         8         9        10        11        12
123456789012345678901234567890123456789012345678901234567890
GLYSLSSVVTVPSSSLGTQTYICNVNHKPSNTKVDKKVEPKSCDKTHTCPPCPAPELLGG KM
GLYSLSSVVTVPSSSLGTQTYICNVNHKPSNTKVDKRVEPKSCDKTHTCPPCPAPELLGG GM 13        14        15        16        17        18
123456789012345678901234567890123456789012345678901234567890
PSVFLFPPKPKDTLMISRTPEVTCVVVDVSHEDPEVKFNWYVDGVEVHNAKTKPREEQYN KM
PSVFLFPPKPKDTLMISRTPEVTCVVVDVSHEDPEVKFNWYVDGVEVHNAKTKPREEQYN GM 19        20        21        22        23        24
123456789012345678901234567890123456789012345678901234567890
STYRVVSVLTVLHQDWLNGKEYKCKVSNKALPAPIEKTISKAKGQPREPQVYTLPPSRDE KM
STYRVVSVLTVLHQDWLNGKEYKCKVSNKALPAPIEKTISKAKGQPREPQVYTLPPSREE GM 25        26        27        28        29        30
123456789012345678901234567890123456789012345678901234567890
LTKNQVSLTCLVKGFYPSDIAVEWESNGQPENNYKTTPPVLDSDGSFFLYSKLTVDKSRW KM
MTKNQVSLTCLVKGFYPSDIAVEWESNGQPENNYKTTPPVLDSDGSFFLYSKLTVDKSRW GM 31        32        33
123456789012345678901234567890
QQGNVFSCSVMHEALHNHYTQKSLSLSPGK KM
QQGNVFSCSVMHEALHNHYTQKSLSLSPGK GM
```

Figure 5

```
          1         2         3         4         5         6
 123456789012345678901234567890123456789012345678901234567890
 TVAAPSVFIFPPSDEQLKSGTASVVCLLNNFYPREAKVQWKVDNALQSGNSQESVTEQDS  Kap
          1         2         3         4         5         6
 1234567890123456789012345678901234567890123456789 1234567890
 QPKAAPSVTLFPPSSEELQANKATLVCLISDFYPGAVTVAWKADSSPVKAG-VETTTPSKQ Lam 7         8         9        10
 1234567890123456789012345678901234567890123456
 KDSTYSLSSTLTLSKADYEKHKVYACEVTHQGLSSPVTKSFNRGEC      Kap
          7         8         9        10
 123456789012345678901234567890123 456789012345
 SNNKYAASSYLSLTPEQWKSHRSYSCQVTHEG--STVEKTVAPTECS     Lam
```

Figure 6

```
          0         1         2         3         4         5
          123456789012345678901234567890123456789012345678901234567890
          AETTAPSVYPLAPGTALKSNSMVTLGCLVKGYFPEPVTVTWNSGALSSGVHTFPAVLQS-    GC1_RAT
          -TTTAPSVYPLVPGCSDTGSSVTLGCLVKGYFPEPVTVKWNYGALSSGVRTVSSVLQS-    GC3_MOUSE
          AKTTAPSVYPLAPVCGDTTGSSVTLGCLVKGYFPEPVTLTWNSGSLSSGVHTFPAVLQS-   GCAA_MOUSE
          AKTTAPSVYPLVPVCGGTTGSSVTLGCLVKGYFPEPVTLTWNSGSLSSGVHTFPALLQS-   GCAB_MOUSE
          AETTAPSVYPLAPGTALKSNSMVTLGCLVKGYFPEPVTVTWNSGALSSGVHTFPAVLQS-    GCA_RAT
          AKTTPPSVYPLAPGCGDTTGSSVTLGCLVKGYFPESVTVTWNSGSLSSSVHTFPALLQS-    GCB_MOUSE
          AQTTAPSVYPLAPGCGDTTSSTVTLGCLVKGYFPEPVTVTWNSGALSSDVHTFPAVLQS-    GCB_RAT
          ARTTAPSVYPLVPGCSGTSGSLVTLGCLVKGYFPEPVTVKWNSGALSSGVHTFPAVLQS-    GCC_RAT
          ASTKGPSVFPLAPSSKSTSGGTAALGCLVKDYFPEPVTVSWNSGALTSGVHTFPAVLQSS   IGHG1_HUMAN
          AKTTPPSVYPLAPGSAAQTNSMVTLGCLVKGYFPEPVTVTWNSGSLSSGVHTFPAVLQS-   IGHG1_MOUSE
          ASTKGPSVFPLAPCSRSTSESTAALGCLVKDYFPEPVTVSWNSGALTSGVHTFPAVLQSS   IGHG2_HUMAN
          ------------------QMQGVNCTVSSELKTP---------LGDTTHTCPRCPEP-    IGHG3_HUMAN
          ASTKGPSVFPLAPCSRSTSESTAALGCLVKDYFPEPVTVSWNSGALTSGVHTFPAVLQSS   IGHG4_HUMAN
                      :.* *.. :   .            * . ..:* .  :.

6         7         8         9         10        11
          123456789012345678901234567890123456789012345678901234567890123.456789012......3
          GLYTLTSSVTVPSSTWPSQTVTCNVAHPASSTKVDKKIVPRNC---GGDCKPC----ICT    GC1_RAT
          GFYSLSSLVTVPSSTWPSQTVICNVAHPASKTELIKRIEPRIP---KPSTPPG---SSCP    GC3_MOUSE
          DLYTLSSSVTVTSSTWPSQSITCNVAHPASSTKVDKKIEPRGP--TIKPCPPC----KCP   GCAA_MOUSE
          GLYTLSSSVTVTSNTWPSQTITCNVAHPASSTKVDKKIEPRVPI-TQNPCPPHQRVPPCA   GCAB_MOUSE
          GLYTLTSSVTVPSSTWSSQAVTCNVAHPASSTKVDKKIVPREC-------NPC----GCT    GCA_RAT
          GLYTMSSSVTVPSSTWPSQTVTCSVAHPASSTTVDKKLEPSGPISTINPCPPCKECHKCP    GCB_MOUSE
          GLYTLTSSVT--SSTWPSQTVTCNVAHPASSTKVDKKVERRNGG-IGHKCPTCPTCHKCP    GCB_RAT
          GLYTLSSSVTVPSSTWSSQTVTCSVAHPATKSNLIKRIEPRRP----KPRPPT---DICS    GCC_RAT
          GLYSLSSVVTVPSSSLGTQTYICNVNHKPSNTKVDKKVEPKSC-DKTHTCPPC------P   IGHG1_HUMAN
          DLYTLSSSVTVPSSPRPSETVTCNVAHPASSTKVDKKIVPRDC-----GCKPC----ICT   IGHG1_MOUSE
          GLYSLSSVVTVPSSNFGTQTYTCNVDHKPSNTKVDKTVERKCC---VECPPC------P   IGHG2_HUMAN
          -----KSCDTPPPCPRCPEPKSCDTPPPCPRCP-----EPKSC----DTPPPC---PRCP   IGHG3_HUMAN
          GLYSLSSVVTVPSSSLGTKTYTCNVDHKPSNTKVDKRVESKYG-------PPC---PSCP   IGHG4_HUMAN
                  .*    *  .   .i.  *...       .                .    .
```

Figure 7A

```
              12        13        14        15        16        17
     456789012345678901234567890123456789012345678901234567890123
     GSEV---SSVFIFPPKPKDVLTITLTPKVTCVVVDISQDDPEVHFSWFVDDVEVHTAQTR  GC1_RAT
     PGNILGGPSVFIFPPKPKDALMISLTPKVTCVVVDVSEDDPDVHVSWFVDNKEVHTAWTQ  GC3_MOUSE
     APNLLGGPSVFIFPPKIKDVLMISLSPIVTCVVVDVSEDDPDVQISWFVNNVEVHTAQTQ  GCAA_MOUSE
     APDLLGGPSVFIFPPKIKDVLMISLSPMVTCVVVDVSEDDPDVQISWFVNNVEVHTAQTQ  GCAB_MOUSE
     GSEV---SSVFIFPPKTKDVLTITLTPKVTCVVVDISQNDPEVRFSWFIDDVEVHTAQTH  GCA_RAT
     APNLEGGPSVFIFPPNIKDVLMISLTPKVTCVVVDVSEDDPDVQISWFVNNVEVHTAQTQ  GCB_MOUSE
     VPELLGGPSVFIFPPKPKDILLISQNAKVTCVVVDVSEEEPDVQFSWFVNNVEVHTAQTQ  GCB_RAT
     CDDNLGRPSVFIFPPKPKDILMITLTPKVTCVVVDVSEEEPDVQFSWFVDNVRVFTAQTQ  GCC_RAT
     APELLGGPSVFLFPPKPKDTLMISRTPEVTCVVVDVSHEDPEVKFNWYVDGVEVHNAKTK  IGHG1_HUMAN
     VPEV---SSVFIFPPKPKDVLTITLTPKVTCVVVDISKDDPEVQFSWFVDDVEVHTAQTQ  IGHG1_MOUSE
     APPV-AGPSVFLFPPKPKDTLMISRTPEVTCVVVDVSHEDPEVQFNWYVDGVEVHNAKTK  IGHG2_HUMAN
     APELLGGPSVFLFPPKPKDTLMISRTPEVTCVVVDVSHEDPEVQFKWYVDGVQVHNAKTK  IGHG3_HUMAN
     APEFLGGPSVFLFPPKPKDTLMISRTPEVTCVVVDVSQEDPEVQFNWYVDGVEVHNAKTK  IGHG4_HUMAN
           .***;***;  ** * *;  .. *******;*.;;*;*;..*;;;. .*...* *;

18        19        20        21        22        23
     456789012345678901234567890123456789012345678901234567890123
     PPEEQFNSTFRSVSELPILHQDWLNGRTFRCKVTSAAFPSPIEKTISKPEGRTQVPHVYT  GC1_RAT
     PREAQYNSTFRVVSALPIQHQDWMRGKEFKCKVNNKALPAPIERTISKPKGRAQTPQVYT  GC3_MOUSE
     THREDYNSTLRVVSALPIQHQDWMSGKEFKCKVNNKDLPAPIERTISKPKGSVRAPQVYV  GCAA_MOUSE
     THREDYNSTLRVVSALPIQHQDWMSGKEFKCKVNNRALPSPIEKTISKPRGPVRAPQVYV  GCAB_MOUSE
     APEKQSNSTLRSVSELPIVHRDWLNGKTFKCKVNSGAFPAPIEKSISKPEGTPRGPQVYT  GCA_RAT
     THREDYNSTIRVVSTLPIQHQDWMSGKEFKCKVNNKDLPSPIERTISKIKGLVRAPQVYI  GCB_MOUSE
     PREEQYNSTFRVVSALPIQHQDWMSGKEFKCKVNNKALPSPIEKTISKPKGLVRKPQVYV  GCB_RAT
     PHEEQLNGTFRVVSTLHIQHQDWMSGKEFKCKVNNKDLPSPIEKTISKPRGKARTPQVYT  GCC_RAT
     PREEQYNSTYRVVSVLTVLHQDWLNGKEYKCKVSNKALPAPIEKTISKAKGQPREPQVYT  IGHG1_HUMAN
     PREEQFNSTFRSVSELPIMHQDWLNGKEFKCRVNSAAFPAPIEKTISKTKGRPKAPQVYT  IGHG1_MOUSE
     PREEQFNSTFRVVSVLTVVHQDWLNGKEYKCKVSNKGLPAPIEKTISKTKGQPREPQVYT  IGHG2_HUMAN
     PREQQFNSTFRVVSVLTVLHQNWLDGKEYKCKVSNKALPAPIEKTISKTKGQPREPQVYT  IGHG3_HUMAN
     PREEQFNSTYRVVSVLTVLHQDWLNGKEYKCKVSNKGLPSSIEKTISKAKGQPREPQVYT  IGHG4_HUMAN
       .. ; *.* * ** * ; *;;*; *; ;;*;*.. ;*;.**;;*** .*  ;  *;**
```

Figure 7B

```
                    24        25        26        27        28        29
           4567890123456789012345678901234567890123456789012345678901234567890123
           MSPTKEEMTQNEVSITCMVKGFYPPDIYVEWQMNGQPQENYKNTPPTMDTDGSYFLYSKL  GC1_RAT
           IPPPREQMSKKKVSLTCLVTNFFSEAISVEWERNGELEQDYKNTPPILDSDGTYFLYSKL  GC3_MOUSE
           LPPPEEEMTKKQVTLTCMVTDFMPEDIYVEWTNNGKTELNYKNTEPVLDSDGSYFMYSKL  GCAA_MOUSE
           LPPPAEEMTKKEFSLTCMITGFLPAEIAVDWTSNGRTEQNYKNTATVLDSDGSYFMYSKL  GCAB_MOUSE
           MAPPKEEMTQSQVSITCMVKGFYPPDIYTEWKMNGQPQENYKNTPPTMDTDGSYFLYSKL  GCA_RAT
           LPPPAEQLSRKDVSLTCLVVGFNPGDISVEWTSNGHTEENYKDTAPVLDSDGSYFIYSKL  GCB_MOUSE
           MGPPTEQLTEQTVSLTCLTSGFLPNDIGVEWTSNGHIEKNYKNTEPVMDSDGSFFMYSKL  GCB_RAT
           IPPPREQMSKNKVSLTCMVTSFYPASISVEWERNGELEQDYKNTLPVLDSDESYFLYSKL  GCC_RAT
           LPPSRDELTKNQVSLTCLVKGFYPSDIAVEWESNGQPENNYKTTPPVLDSDGSFFLYSKL  IGHG1_HUMAN
           IPPPKEQMAKDKVSLTCMITDFFPEDITVEWQWNGQPAENYKNTQPIMNTNGSYFVYSKL  IGHG1_MOUSE
           LPPSREEMTKNQVSLTCLVKGFYPSDIAVEWESNGQPENNYKTTPPMLDSDGSFFLYSKL  IGHG2_HUMAN
           LPPSREEMTKNQVSLTCLVKGFYPSDIAVEWESSGQPENNYNTTPPMLDSDGSFFLYSKL  IGHG3_HUMAN
           LPPSQEEMTKNQVSLTCLVKGFYPSDIAVEWESNGQPENNYKTTPPVLDSDGSFFLYSRL  IGHG4_HUMAN
           : *. ::::..  .::**: .* .  * .:*  .*.   :*: *  . :::: ::*:**:*

30        31        32
           456789012345678901234567890123456789 0
           NVKKEKWQQGNTFTCSVLHEGLHNHHTEKSLSHSPGK  GC1_RAT
           TVDTDSWLQGEIFTCSVVHEALHNHHTQKNLSRSPGK  GC3_MOUSE
           RVEKKNWVERNSYSCSVVHEGLHNHHTTKSFSRTPGK  GCAA_MOUSE
           RVQKSTWERGSLFACSVVHEVLHNHLTTKTISRSLGK  GCAB_MOUSE
           NVKKETWQQGNTFTCSVLHEGLHNHHTEKSLSHSPGK  GCA_RAT
           NMKTSKWEKTDSFSCNVRHEGLKNYYLKKTISRSPGK  GCB_MOUSE
           NVERSRWDSRAPFVCSVVHEGLHNHHVEKSISRPPGK  GCB_RAT
           SVDTDSWMRGDIYTCSVVHEALHNHHTQKNLSRSPGK  GCC_RAT
           TVDKSRWQQGNVFSCSVMHEALHNHYTQKSLSLSPGK  IGHG1_HUMAN
           NVQKSNWEAGNTFTCSVLHEGLHNHHTEKSLSHSPGK  IGHG1_MOUSE
           TVDKSRWQQGNVFSCSVMHEALHNHYTQKSLSLSPGK  IGHG2_HUMAN
           TVDKSRWQQGNIFSCSVMHEALHNRFTQKSLSLSPGK  IGHG3_HUMAN
           TVDKSRWQEGNVFSCSVMHEALHNHYTQKSLSLSLGK  IGHG4_HUMAN
           :. . *    :  *.* ** *:*    *.:* . **
```

Figure 7C

```
                                                                60
              123456789012345678901234567890123456789012345678901234567890
mFc_IGHG1     VPRDCGCKPCICTVPEVSSVFIFPPKPKDVLTITLTPKVTCVVVDISKDDPEVQFSWFVD
mFc_dm_NKG2A  VPRDCGCKPCICTVPEVSSVFIFPPKPKDVLTITLTPKVTCVVVDISKDDPEVQFSWFVD
mFc_dm_CD94   VPRDCGCKPCICTVPEVSSVFIFPPKPKDVLTITLTPKVTCVVVDISKDDPEVQFSWFVD
mFc_sm_NKG2A  VPRDCGCKPCICTVPEVSSVFIFPPKPKDVLTITLTPKVTCVVVDISKDDPEVQFSWFVD
mFc_sm_CD94   VPRDCGCKPCICTVPEVSSVFIFPPKPKDVLTITLTPKVTCVVVDISKDDPEVQFSWFVD
mFc           VPRDCGCKPCICTVPEVSSVFIFPPKPKDVLTITLTPKVTCVVVDISKDDPEVQFSWFVD
              ************************************************************

120
              123456789012345678901234567890123456789012345678901234567890
mFc_IGHG1     DVEVHTAQTQPREEQFNSTFRSVSELPIMHQDWLNGKEFKCRVNSAAFPAPIEKTISKTK
mFc_dm_NKG2A  DVEVHTAQTKPREEQFNSTFRSVSELPIMHQDWLNGKEFKCRVNSAAFPAPIEKTISKTK
mFc_dm_CD94   DVEVHTAQTKPREEQFNSTFRSVSELPIMHQDWLNGKEFKCRVNSAAFPAPIEKTISKTK
mFc_sm_NKG2A  DVEVHTAQTKPREEQFNSTFRSVSELPIMHQDWLNGKEFKCRVNSAAFPAPIEKTISKTK
mFc_sm_CD94   DVEVHTAQTKPREEQFNSTFRSVSELPIMHQDWLNGKEFKCRVNSAAFPAPIEKTISKTK
mFc           DVEVHTAQTKPREEQFNSTFRSVSELPIMHQDWLNGKEFKCRVNSAAFPAPIEKTISKTK
              ********:***************************************************

180
              123456789012345678901234567890123456789012345678901234567890
mFc_IGHG1     GRPKAPQVYTIPPPKEQMAKDKVSLTCMITDFFPEDITVEWQWNGQPAENYKNTQPIMNT
mFc_dm_NKG2A  GRPKAPQVYTIPPPKEQMAKDKVSLTCMITDFFPEDITVEWQWNGQPAENYKNTQPIMKT
mFc_dm_CD94   GRPKAPQVYTIPPPKKQMAKDKVSLTCMITDFFPEDITVEWQWNGQPAENYKNTQPIMDT
mFc_sm_NKG2A  GRPKAPQVYTIPPPKEQMAKDKVSLTCMITDFFPEDITVEWQWNGQPAENYKNTQPIMDT
mFc_sm_CD94   GRPKAPQVYTIPPPKEQMAKDKVSLYCMITDFFPEDITVEWQWNGQPAENYKNTQPIMDT
mFc           GRPKAPQVYTIPPPKEQMAKDKVSLTCMITDFFPEDITVEWQWNGQPAENYKNTQPIMDT
              ***************:********************************************.*

227
              12345678901234567890123456789012345678901234567
mFc_IGHG1     NGSYFVYSKLNVQKSNWEAGNTFTCSVLHEGLHNHHTEKSLSHSPGK
mFc_dm_NKG2A  DGSYFVYSKLNVQKSNWEAGNTFTCSVLHEGLHNHHTEESLSHSPGK
mFc_dm_CD94   DGSYFVYSDLNVQKSNWEAGNTFTCSVLHEGLHNHHTEKSLSHSPGK
mFc_sm_NKG2A  DGSYFVTSKLNVQKSNWEAGNTFTCSVLHEGLHNHHTEKSLSHSPGK
mFc_sm_CD94   DGSYFVYSKLNVQKSNWEAGNTFTCSVLHEGLHNHHTEKSLSHSPGK
mFc           DGSYFVYSKLNVQKSNWEAGNTFTCSVLHEGLHNHHTEKSLSHSPGK
              :**** *.*****************************:*********
```

Figure 8

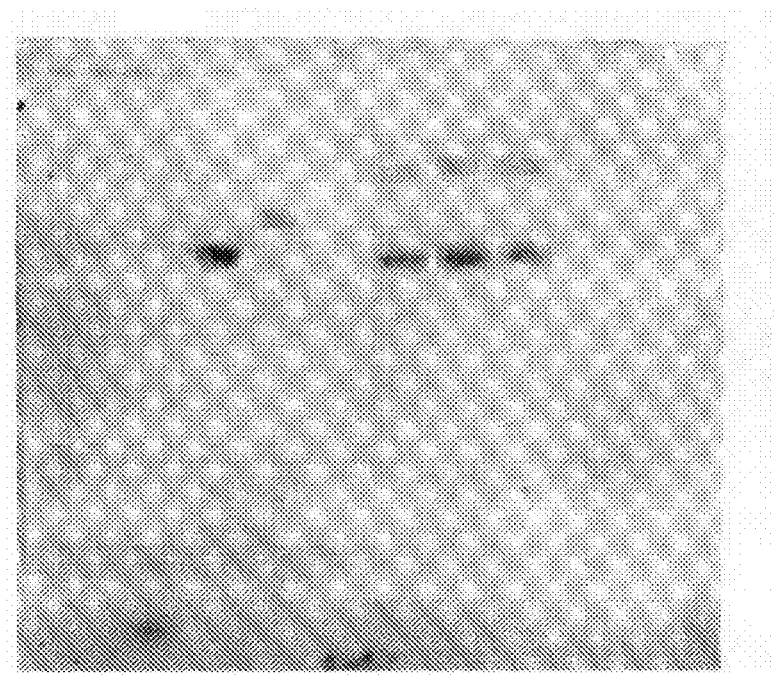
A
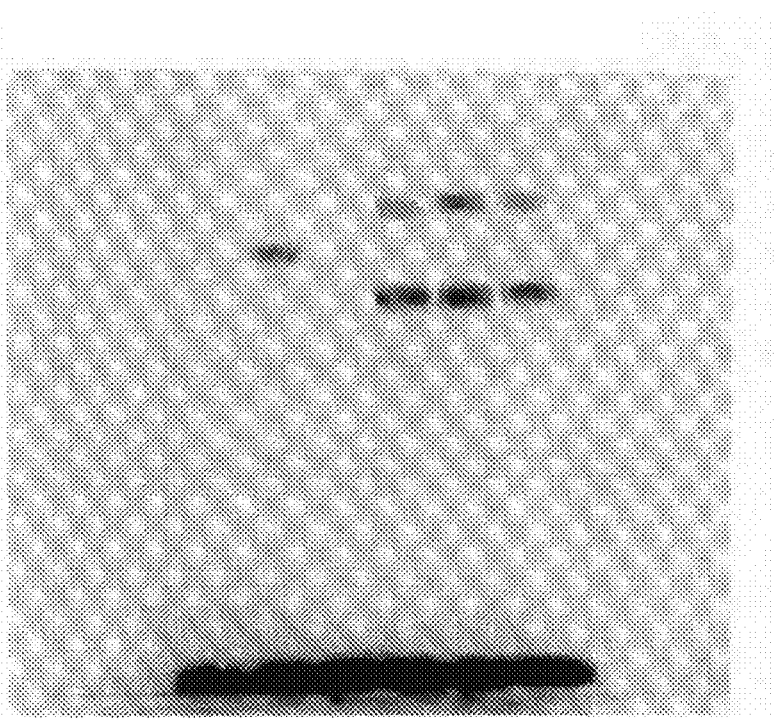
B
Figure 13

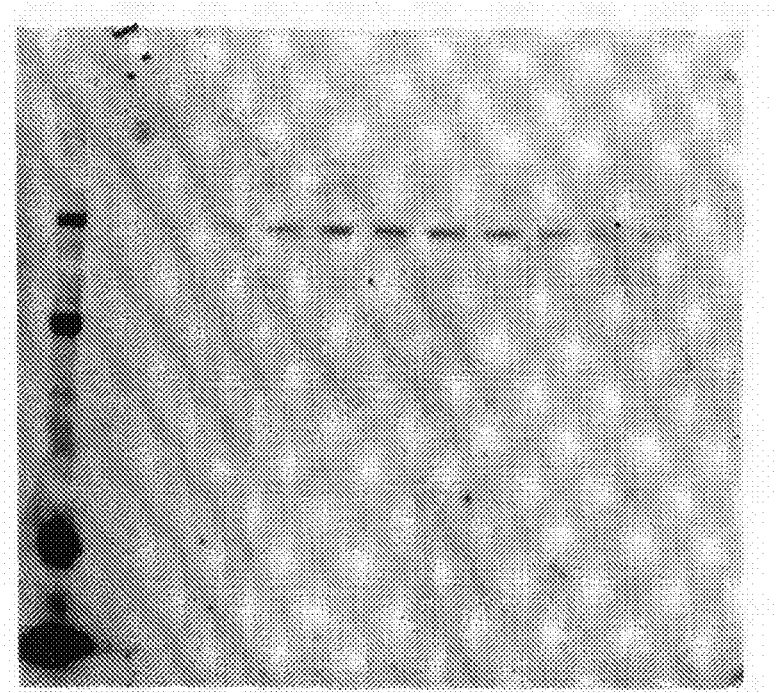
A
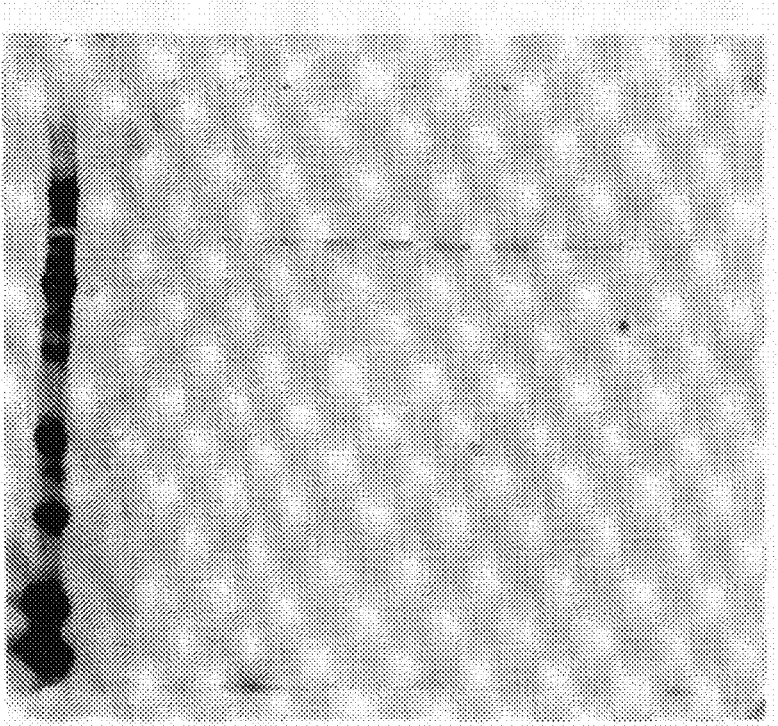
B
Figure 14

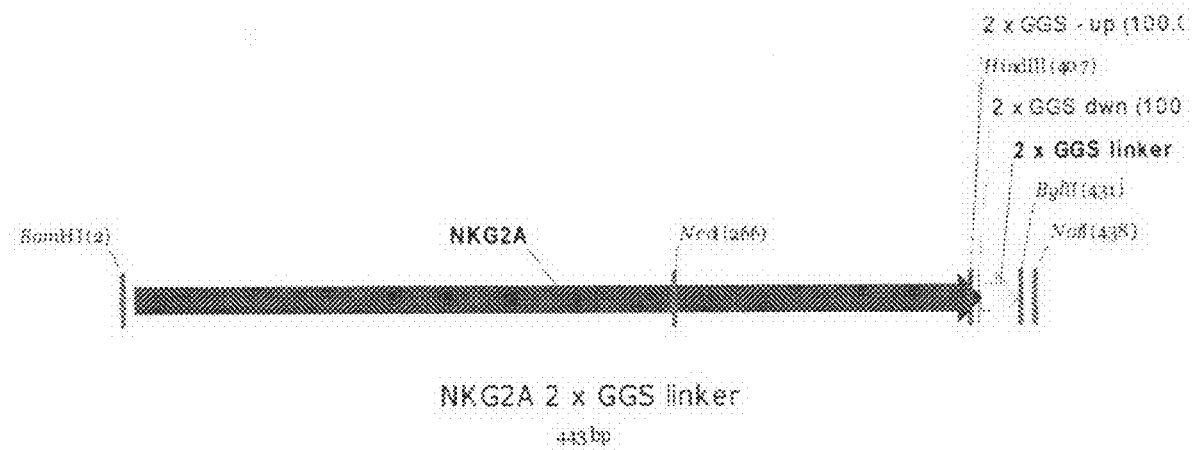
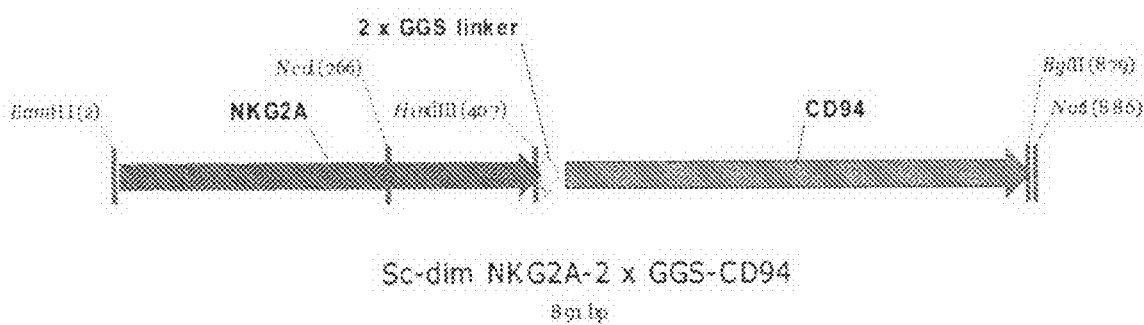
Figure 19

```
              9         10        11        12        13        14        15
              456789012345678901234567890123456789012345678901234567890 1A2
NKG2A_94_233  PSTLIQRHNNSSLNTRTQKARHCGHCPEEWITYSNSCYYIGKERRTWEESLLACTSKN-S
NKG2B_76_215  PS----------------RHCGHCPEEWITYSNSCYYIGKERRTWEESLLACTSKN-S
NKG2C_94_231  --IPFLEQNNSSPNTRTQKARHCGHCPEEWITYSNSCYYIGKERRTWEESLLACTSKN-S
NKG2E_94_240  --IPFLEQNNSSPNTRTQKARPCGHCPEEWITYSNSCYYIGKERRTWEESLQACASKNSS
NKG2F_96_158  -CIGVLEQNSFSLNRRMQKARHCGHCPEEWITYSNSCYYIGKERRTWEERV--C------
                                 * *************************** :  *

16        17        18        19        20        21
              345678901234567890123456789012345678901234567890123456789012
NKG2A_94_233  SLLSIDNEEEMKFLSIISPSSWIGVFRNSSHHPWVTMNGLAFKHEIKDSDNAELNCAVLQ
NKG2B_76_215  SLLSIDNEEEMKFLSIISPSSWIGVFRNSSHHPWVTMNGLAFKHEIKDSDNAELNCAVLQ
NKG2C_94_231  SLLSIDNEEEMKFLASILPSSWIGVFRNSSHHPWVTINGLAFKHKIKDSDNAELNCAVLQ
NKG2E_94_240  SLLSIDNEEEMKFLASILPSSWIGVFRNSSHHPWVTINGLAFKHEIKDSDHAERNCAMLH
NKG2F_96_158  --------------------W-PVLRRT------------------------LICFL--
                                  *  *:*.:                           * :

22        23
              345678901234567890123ABCDEFGH
NKG2A_94_233  VNRLKSAQCGSSIIYHCKHKL--------
NKG2B_76_215  VNRLKSAQCGSSIIYHCKHKL--------
NKG2C_94_231  VNRLKSAQCGSSMIYHCKHKL--------
NKG2E_94_240  VRGLISDQCGSSRIIRRGFIMLTRLVLNS
NKG2F_96_158  -----------------------------
```

Figure 25

SOLUBLE HETERODIMERIC CD94/NKG2 RECEPTORS FUSION PROTEINS

CROSS-REFERENCE TO RELATED APPLICATIONS

This application is a 35 U.S.C. §371 national stage application of International Patent Application PCT/EP2007/056276 (published as WO 2007/147898), filed Jun. 22, 2007, which claimed priority of European Patent Application 06115901.8, filed Jun. 22, 2006; this application further claims priority under 35 U.S.C. §119 of U.S. Provisional Application 60/817,116, filed Jun. 28, 2006.

FIELD OF THE INVENTION

This invention relates to soluble heterodimeric receptors for therapeutic and diagnostic applications, and to methods of designing and producing such soluble heterodimeric receptors. Exemplary compositions of the invention comprise soluble fragments of heterodimeric receptors as well as the Fc-portion of immunoglobulins.

BACKGROUND OF THE INVENTION

Soluble receptors, such as soluble TNFR (Enbrel®), have proven great value for therapeutical applications. Soluble receptors may also be used for diagnostic purposes, as well, e.g., for the screening of ligand-expression on diseased tissues, such as tumor-tissues in cancer patients.

The CD94/NKG2 family of receptors is composed of heterodimeric receptor members with activating or inhibitory potential. These receptors are expressed predominantly on NK cells and a subset of CD8+T cells, and they have been shown to play an important role in regulating responses against infected and tumorigenic cells. The main ligand for the CD94/NKG2 receptor is HLA-E. U.S. Pat. No. 6,262,244 to Houchins et al. described the human NKG2A sequence (SEQ ID NO:1), and Chang et al. (Eur J Immunol. 1995;25:2433-7) reported the human CD94 sequence (SEQ ID NO:2).

Soluble versions of CD94/NKG2 receptors are of interest not only as research tools but also as therapeutic agents. Both therapeutical and diagnostic applications, however, require stable soluble receptors that can be produced efficiently in a suitable biosystem. For many heterodimeric receptors such as, e.g., CD94/NKG2, this has, so far, proven difficult. Potential reasons are homo-dimerization of the single subunits, and that the more complex structure of heterodimeric receptors makes it more difficult to design soluble versions that are sufficiently stable.

Certain soluble CD94/NKG2A constructs, based on the expression of tagged soluble portions of the CD94 and NKG2A proteins, have been proposed in the literature (Brooks et al., J Immunol 1999:162:305-13; Ding et al Scand. J. Immunol. 1999;49:459-465; and Kaiser et al. Journal of Immunology, 2005, 174: 2878-2884). Soluble versions of other multimeric receptors, some of which fused to immunoglobulin Fc portions, have been described in, e.g., WO9937772, WO200208272, and WO20023237, relating to multimeric IL-18 receptor molecules; Wu et al. (Protein Sci. 1999;8:482-9), describing soluble forms of the IL-2 receptor; WO200222153, describing a soluble IL-20 receptor; WO200212345, relating to soluble ZCY-TOR 11 cytokine receptors, WO2002101006, relating to heteromultimeric proteins such as T-cell receptors, WO9533059, describing a heterodimeric receptor of gp130 and oncostatin M receptor beta chain, and U.S. Pat. No. 6,238,890, describing soluble forms of various glycoproteins. Soluble versions of heterodimeric T-cell receptors or subunits thereof have also been described in, e.g., Clements et al., Acta Crystallogr D Biol Crystallogr. 2002;58:21314; Laugel et al., J. Biol. Chem. 2005;280:1882-1892; Kim et al., J Mol Biol. 2000;302:899-916.

Further, U.S. Patent Publication Nos. 20030195338 and 20040072256 describe various types of Fc-linked receptor sequence proteins, U.S. Pat. No. 6,018,026 relates to dimerized fusion proteins; U.S. Pat. No. 6,833,441 relates to methods for generating chimeric heteromultimers; WO92/06204 and WO03012069 relate to, e.g., techniques for producing libraries of heterodimeric receptors; U.S. Patent Publication No. 20040138417 describes heteromultimer adhesins. Also, principles to promote heteromultimer formation are described in U.S. Patent Publication No. 20030078385, and reviewed in Marvin and Zhu, Acta Pharmacol Sin 2005;26(6):649-658 (see also Kontermann, Acta Pharmacol. Sin. 2005;26:1-9.

However, there remains a need for soluble versions of heterodimeric receptors such as CD94/NKG2 for diagnostic or therapeutic applications, and efficient methods of producing stable soluble heterodimeric receptors. The present invention addresses these and other needs in the art.

SUMMARY OF THE INVENTION

The present invention provides for soluble constructs of heterodimeric receptors. The constructs comprise an essentially soluble portion of a first and second subunits of a heterodimeric receptor. In some aspects, the constructs further comprise one or two Fc-portions of an immunoglobulin molecule. In one exemplary aspect, each soluble portion is associated or covalently linked to an Fc-portion of an immunoglobulin, and the final construct comprises one of each subunit-Fc fusion or hybrid polypeptide. In another exemplary aspect, the Fc-portion of each subunit-Fc fusion or hybrid polypeptide comprises one or more mutations promoting heterodimerization of a fusion or hybrid polypeptide comprising a soluble portion of the first subunit to a fusion or hybrid polypeptide comprising a soluble portion of the second subunit, thus reducing homodimerization between identical subunit-Fc polypeptides. In yet another exemplary aspect, the soluble receptor construct is a single-chain soluble receptor-Fc fusion or hybrid protein-complex, comprising the soluble portion of the first subunit linked to the soluble portion of the second subunit. In still another exemplary aspect, the soluble receptor construct is a single-chain soluble receptor-Fc fusion or hybrid protein-complex, comprising the soluble portion of the first subunit linked to the soluble portion of the second subunit which, in turn, is linked to an Fc-portion. In one embodiment, the invention provides dimers of the single-chain receptor-Fc fusion or hybrid protein.

In one aspect, the heterodimeric receptor is an CD94/NKG2 receptor. In another aspect, the heterodimeric receptor is a CD94/NKG2A receptor.

The invention also provides for various methods of making such soluble constructs, as well as various uses of the soluble constructs according to the invention. One exemplary use is in the detection of the natural ligand (e.g., HLA-E) in a biological sample.

These and other aspects are described in more detail below and in the drawings.

DESCRIPTION OF THE DRAWINGS

FIG. 5: Labeling of the constant part of the heavy chain for the GM (SEQ ID NO:8) and KM (SEQ ID NO:9) allotypes.

FIG. 6: Labeling of the Kappa (SEQ ID NO:10) and Lambda (SEQ ID NO.11) constant regions.

FIG. 7A-7C: Alignment of immunoglobulin sequences from human, mouse and rat, referred to by the respective UNIPROT entry name. (GC1_RAT: SEQ ID NO:12; GC3_MOUSE: SEQ ID NO:13; GCAA_MOUSE: SEQ ID NO:14; GCAB_MOUSE: SEQ ID NO:15; GCA_RAT: SEQ ID NO:16; GCB_MOUSE: SEQ ID NO:17; GCB_RAT: SEQ ID NO:18; GCC_RAT: SEQ ID NO:19; IGHG1_HUMAN: SEQ ID NO:20; IGHG1_MOUSE: SEQ ID NO:21; IGHG2_HUMAN: SEQ ID NO:22; IGHG3_HUMAN: SEQ ID NO:23; IGHG4_HUMAN: SEQ ID NO:24).

FIG. 8: Alignment of murine wild-type and variant immunoglobulin sequences. mFc: SEQ ID NO:25; mFc-IGHG1: residues 98 to 324 of SEQ ID NO:21; mFc_dm_NKG2A: SEQ ID NO:26; mFc_dm_CD94: SEQ ID NO:27; mFc_sm_NKG2A: SEQ ID NO:28; and mFc_sm_CD94: SEQ ID NO:29.

FIGS. 13A and B: SDS-PAGE/Western blot analysis of constructs after protein A purification using (A) anti-CD94 (HP-3D9) antibody (Cy3-labeled), or (B) anti-NKG2A (Z199) antibody (Cy5-labeled). Lane 1: MW marker (not seen); Lane 2: pBF5 CD94-mFc; Lane 3:pBF17 CD94-2× GGS-NKG2A-mFc; Lane 4: pBF6 NKG2A-mFc; Lane 5: pBF19 CD94-mFc T249Y and pBF20 NKG2A-mFc Y290T; Lane 6: pBF5 CD94-mFc and pBF6 NKG2A-mFc; Lane 7: pBF21 CD94-mFc E239K, K292D and pBF22 NKG2A-mFc D282K, K332E (Example 8).

FIGS. 14A and B: SDS-PAGE/Western blot of different fractions from purification of CD-94-2×GGS-NKG2A-mFc on Protein A column using (A) anti-CD94 (HP-3D9) antibody (Cy3-labelled B) and (B) anti-NKG2A (Z199) antibody (Cy5-labelled). Lane 1: MW marker; Lane 2: Application; Lane 3: Flowthrough; Lane 4: Fraction A10; Lane 5: Fraction A11; Lane 6: Fraction A12; Lane 7: Fraction B1; Lane 8: Fraction B2; Lane 9: Fraction B3; Lane 10: Fraction B4; Lane 11: Fraction B5; Lane 12: Fraction B6.

FIGS. 19A and B: (A) NKG2A-2×GGS construct; (B) NKG2A-2×GGS-CDF94 construct (Example 13).

FIG. 25: Alignment of extracellular portions of NKG2 proteins. Numbering according to the NKG2A full sequence (SEQ ID NO:1). See SEQ ID NOS:1 (NKG2A), 3 (NKG2C), 4 (NKG2E), 5 (NKG2F), and 70 (NKG2B) for full-length sequences.

DEFINITIONS

Figure 1:
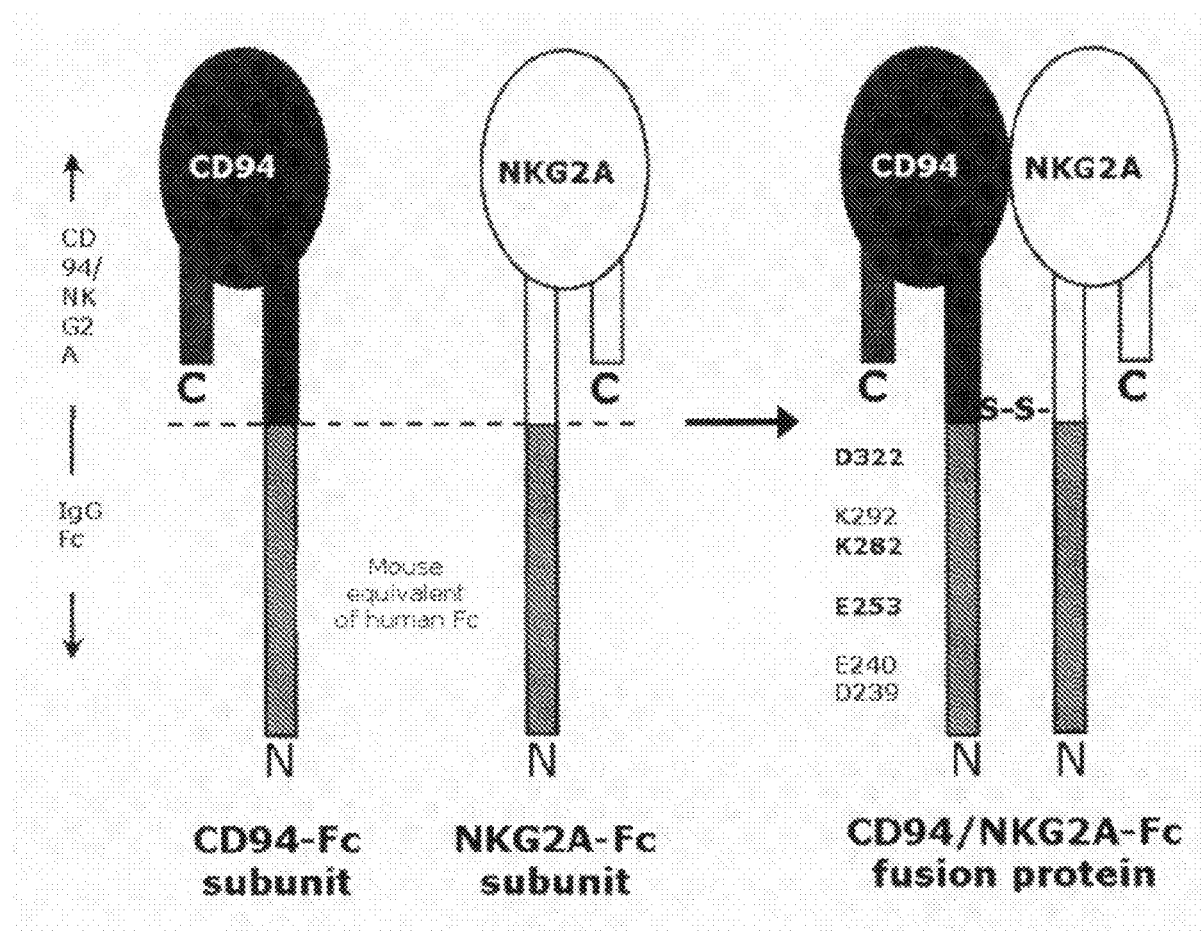
FIG. 1: Exemplary soluble CD94/NKG2A Fc fusion protein.

The term "receptor" denotes a cell-associated protein that binds to a bioactive molecule (i.e., a ligand) and mediates the effect of the ligand on the cell. Membrane-bound receptors are characterized by a multi-domain structure comprising an extracellular ligand-binding domain and an intracellular effector domain that is typically involved in signal transduction. Binding of ligand to receptor results in a conformational change in the receptor that causes an interaction between the effector domain and other molecule(s) in the cell. This interaction in turn leads to an alteration in the metabolism of the cell. Metabolic events that are linked to receptor-ligand interactions include gene transcription, phosphorylation, dephosphorylation, increases in cyclic AMP production, mobilization of cellular calcium, mobilization of membrane lipids, cell adhesion, hydrolysis of inositol lipids and hydrolysis of phospholipids. An exemplary receptor described herein is the CD94/NKG2A receptor.

By "multimeric" or "heteromultimeric" is meant comprising two or more different subunits. A "heterodimeric" receptor contains two different subunits, herein denoted "S1" (subunit 1) and "S2" (subunit 2).

By "soluble" multimeric receptor is meant herein a multimeric receptor, each of whose subunits comprises part or all of an extracellular domain of a receptor, but lacks part or all of any transmembrane domain, and lacks all of any intracellular domain. In general, a soluble receptor of the invention is soluble in an aqueous solution. However, under certain conditions, the receptor can be in the form of an inclusion body, which is readily solubilized by standard procedures. A "soluble portion of subunit 1" can herein be denoted "sS1" whereas "a soluble portion of subunit 2" can be denoted "sS2".

A "hybrid" protein is a protein comprising two polypeptide segments linked via at least one linkage other than a peptide bond (e.g., by chemical coupling or an affinity interaction such as via, e.g., biotin/avidin).

A "fusion" protein is a protein comprising two polypeptide segments linked by a peptide bond, produced, e.g., by recombinant processes.

The term "NKG2" includes full-length or partial polypeptides from any and all members of the NKG2 family, including, but not limited to, NKG2A, NKG2B, NKG2C, NKG2E, and NKG2F, as well a human and non-human orthologs of these members and variants thereof. Typically, the amino acid sequence of a variant of an NKG2 polypeptide is highly identical or similar to the amino acid sequence of the corresponding wild-type NKG2 polypeptide (e.g., at least about 80%, at least about 85%, at least about 90%, at least about 95%, 96%, 97%, 98%, or 99% identical).

The term "NKG2A" includes full-length or partial NKG2A polypeptides from both human and non-human orthologs, as well as variants thereof. Typically, the amino acid sequence of a variant of an NKG2A polypeptide is highly identical or similar to the amino acid sequence of a wild-type NKG2A polypeptide (e.g., at least about 80%, at least about 85%, at least about 90%, at least about 95%, 96%, 97%, 98%, or 99% identical).

The term "NKG2C" includes full-length or partial NKG2A polypeptides from both human and non-human orthologs, as well as variants thereof. Typically, the amino acid sequence of a variant of an NKG2A polypeptide is highly identical or similar to the amino acid sequence of a wild-type NKG2A polypeptide (e.g., at least about 80%, at least about 85%, at least about 90%, at least about 95%, 96%, 97%, 98%, or 99% identical).

The term "CD94" includes full-length or partial CD94 polypeptides from both human and non-human orthologs, as well as variants thereof. Typically, the amino acid sequence of a variant of an CD94 polypeptide is highly identical or similar to the amino acid sequence of a wild-type CD94 polypeptide (e.g., at least about 80%, at least about 85%, at least about 90%, at least about 95%, 96%, 97%, 98%, or 99% identical).

The term "ortholog" denotes a polypeptide or protein obtained from one species that is the functional counterpart of a polypeptide or protein from a different species. Sequence differences among orthologs are the result of speciation.

An "Fc domain" herein generally refers to a polypeptide comprising all or part of the Fc domain of an immunoglobulin heavy-chain. This includes, but is not limited to, polypeptides comprising the entire CH1, hinge, CH2, and/or CH3 domains as well as fragments of such peptides comprising only, e.g., the hinge, CH2, and CH3 domain. The Fc domain may be derived from an immunoglobulin of any species and/or any subtype, including, but not limited to, a human IgG1, IgG2, IgG3, IgG4, IgD, IgA, IgE, or IgM antibody. Exemplary Fc sequences are provided herein, e.g., in FIGS. 5-7.

As used herein, a "variant" polypeptide of a parent or wild-type polypeptide contains one or more amino acid substitutions, deletions and/or additions as compared to the parent or wild-type. Typically, such variants have a sequence identity to the parent or wild-type sequence of at least about 90%, at least about 95%, at least about 96%, at least about 97%, 98%, or at least about 99%, and have preserved or improved properties as compared to the parent or wild-type polypeptide. Some changes may not significantly affect the folding or activity of the protein or polypeptide; conservative amino acid substitutions, as are well known in the art, changing one amino acid to one having a side-chain with similar physicochemical properties (basic amino acid: arginine, lysine, and histidine; acidic amino acids: glutamic acid, and aspartic acid; polar amino acids: glutamine and asparagine; hydrophobic amino acids: leucine, isoleucine, valine; aromatic amino acids: phenylalanine, tryptophan, tyrosine; small amino acids: glycine, alanine, serine, threonine, methionine), small deletions, typically of one to about 30 amino acids; and small amino- or carboxyl-terminal extensions, such as an amino-terminal methionine residue, a small linker peptide of up to about 20-25 residues, or a small extension that facilitates purification (an affinity tag), such as a poly-histidine tract, protein A (Nilsson et al., EMBO 1985; 14:1075 et seq.; Nilsson et al., Methods Enzymol. 1991; 198:3 et seq.), glutathione S-transferase (Smith and Johnson, Gene 1988;67:31 et seq.), or other antigenic:epitope or binding domain. See, in general Ford et al., Protein Expression and Purification 1991;2:95-107. DNAs encoding affinity tags are available from commercial suppliers.

Sequence differences or "identity," in the context of amino acid sequences, can be determined by any suitable technique, such as (and as one suitable selection in the context of this invention) by employing a Needleman-Wunsch alignment analysis (see Needleman and Wunsch, J. Mol. Biol. (1970) 48:443453), such as is provided via analysis with ALIGN 2.0 using the BLOSUM50 scoring matrix with an initial gap penalty of −12 and an extension penalty of −2 (see Myers and Miller, CABIOS (1989) 4:11-17 for discussion of the global alignment techniques incorporated in the ALIGN program). A copy of the ALIGN 2.0 program is available, e.g., through the San Diego Supercomputer (SDSC) Biology Workbench. Because Needleman-Wunsch alignment provides an overall or global identity measurement between two sequences, it should be recognized that target sequences which may be portions or subsequences of larger peptide sequences may be used in a manner analogous to complete sequences or, alternatively, local alignment values can be used to assess relationships between subsequences, as determined by, e.g., a Smith-Waterman alignment (J. Mol. Biol. (1981) 147:195-197), which can be obtained through available programs (other local alignment methods that may be suitable for analyzing identity include programs that apply heuristic local alignment algorithms such as FastA and BLAST programs). Further related methods for assessing identity are described in, e.g., International Patent Application WO 03/048185. The Gotoh algorithm, which seeks to improve upon the Needleman-Wunsch algorithm, alternatively can be used for global sequence alignments. See, e.g., Gotoh, J. Mol. Biol. 162:705-708 (1982).

DESCRIPTION OF THE INVENTION

The present invention provides for soluble receptor-complexes from heterodimeric receptors, all comprising a soluble portion of each of the two subunits of a heterodimeric receptor, and, in some aspects, at least one Fc-portion of an immunoglobulin molecule.

In one aspect, each soluble portion is associated or covalently linked to an Fc-portion of an immunoglobulin, and the final soluble-receptor complex is formed by associating or covalently linking the hybrid or fusion protein comprising the soluble portion of the first subunit (sS1-Fc) to the hybrid or fusion protein comprising the soluble portion of the second subunit (sS2-Fc). Linkage of the various segments may be obtained via, e.g., covalent binding such as by chemical cross-linking, peptide linkers, disulfide bridges, etc., or affinity interactions such as by avidin-biotin or leucine zipper technology.

Another aspect is similar to the one describe above, but the Fc-molecule of each fusion protein comprises specific mutations designed to produce forced heterodimerisation between the different fusion proteins, resulting in a soluble-receptor complex where fusion protein sS1-Fc1 is fused with sS2-Fc2.

In yet another aspect, the soluble receptor complex is a single-chain soluble receptor-Fc fusion or -hybrid proteincomplex, comprising the soluble portion of the first subunit (sS1) linked to the soluble portion of the second subunit (sS2). In a particular embodiment, the C-terminal of one of sS1 and sS2 is further linked to an Fc-portion. Linkage of the various segments may be obtained via, e.g., covalent binding such as by chemical cross-linking, peptide linkers, disulfide bridges, etc., or affinity interactions such as by avidin-biotin or leucine zipper technology. In one embodiment, the single-chain receptor protein is a fusion protein, i.e., all linkages between different segments in the protein are via peptide linkers or via direct peptide-peptide binding.

In still another aspect, two units of the single-chain Fc-fusion protein described above are joined or linked, thus essentially forming a homodimer of a heterodimeric receptor. In one exemplary embodiment, the heterodimeric receptor is a CD94/NKG2 receptor, and the two single-chain Fc-fusion proteins are linked via a disulfide bond between cysteine residues naturally occurring in the soluble segments of the CD94 and NKG2 subunits.

The soluble receptor-complexes of heterodimeric receptors according to the invention can be more stable and thus can be stored longer. In addition, stable soluble receptor-complexes from heterodimeric receptors are suitable in applications where a longer half-life is required, e.g., for immunizations and therapeutical applications.

As described in the Examples, the N and C-terminals of CD94 and NKG2A were found to be close in an in silico CD94/NKG2A model. This confirmed the suitability of soluble CD94/NKG2 heterodimeric receptors according to the invention, since a C-terminal of a first subunit can then be linked to the N-terminal of the second subunit by a short peptide linker, and because of high sequence homology in the soluble portions of NKG2 proteins (see FIG. 25). Thus, in separate and specific embodiments, the heterodimeric receptor is one wherein the N-terminal of the first subunit is close to the C-terminal of the second subunit are close, or one wherein the N-terminal of the first subunit is close to the C-terminal of the second subunit and the C-terminal of the first subunit is close to the N-terminal of the second subunit. For example, in one embodiment, "close" as used herein means that the distance between the respective alpha-carbons is within about 4 to about 40, about 4 to about 30, about 4 to about 20, or about 4 to about 15, Ångström of each other. In another embodiment, "close" means within about 13 to about 15 Ångstrom of each other.

The following are exemplary soluble CD94/NKG2 constructs:

1) CD94-Fc/NKG2-Fc: A stable Fc-fusion protein or hybrid-protein conjugate comprising extracellular domains of CD94 and an NKG2 protein which are both conjugated or fused to murine Fc. The protein can be produced and secreted from mammalian cells and purified by a single-step affinity-chromatography. In one exemplary embodiment, this soluble receptor complex can be illustrated by FIG. 1, where the disulfide bridge illustrated is one that naturally occurs in the CD94/NKG2A receptor.

Figure 2:
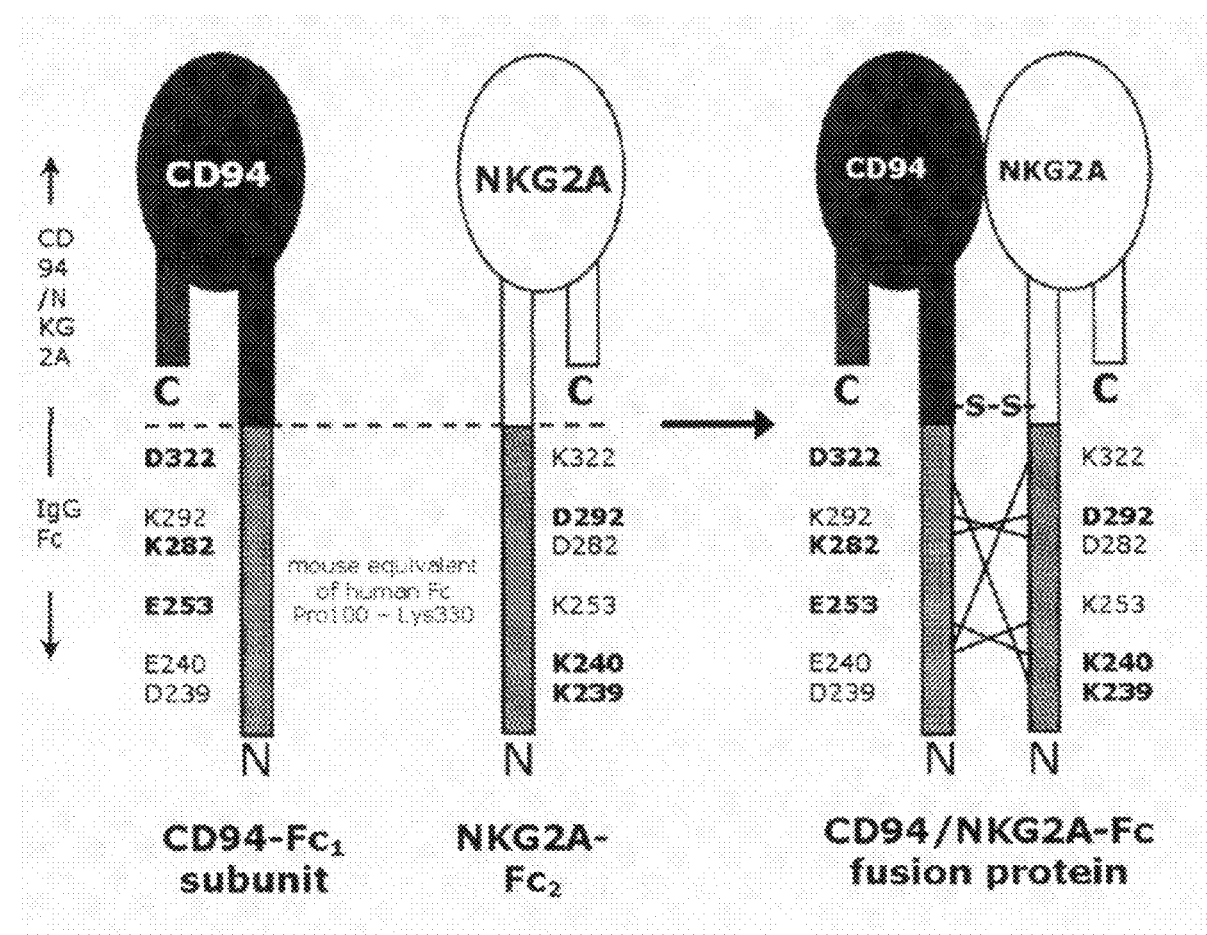
FIG. 2: Exemplary soluble CD94/NKG2A Fc-fusion protein comprising forced Fc1-Fc2 heterodimerisation. Constructs with mutations in the charged residues of the Fc domain allow the heterodimer be formed from independent CD94-Fc and NKG2A-Fc chains.

2) CD94-Fc$_1$/NKG2-Fc$_2$: A stable Fc-fusion protein or -protein conjugate comprising extracellular domains of CD94 and an NKG2 protein, each of which is fused to a differently mutated murine Fc-domain. The mutations in the Fc-domain fused or conjugated to the CD94 soluble segment promote dimerization with the mutated Fc-domain fused or conjugated to the soluble NKG2 segment, and vice versa, thus avoiding CD94- or NKG2-homodimerisation. The protein can be produced and secreted from mammalian cells and purified by a single-step affinity-chromatography. In one exemplary embodiment, this soluble receptor complex can be illustrated by FIG. 2, where the disulfide bridge illustrated is one that naturally occurs in the CD94/NKG2A receptor.

Figure 3:
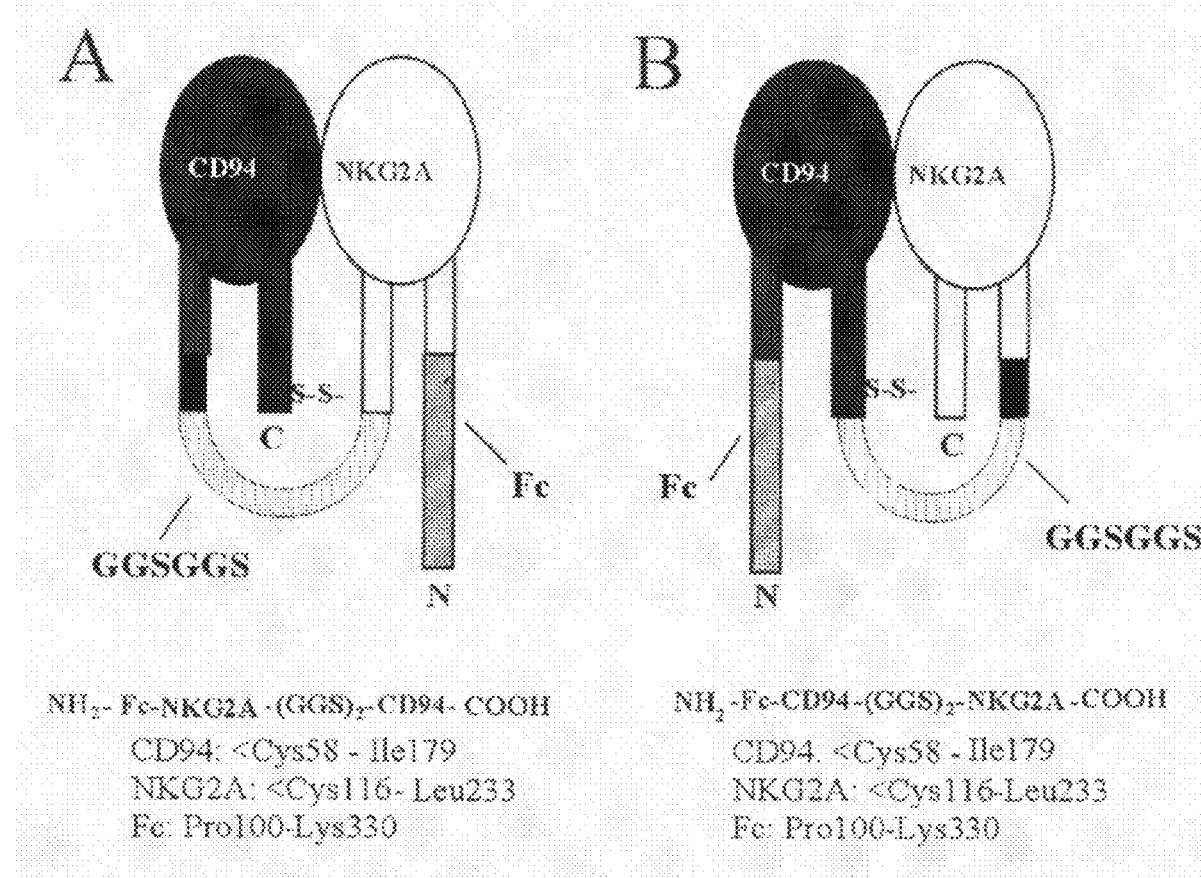
FIGS. 3A and B: (A) Exemplary single chain Fc-NKG2A-CD94 fusion protein with a GGSGGS linker from the C-terminal of NKG2A to the N-terminal of CD94. (B) Exemplary single chain Fc-CD94-NKG2A with a GGSGGS (SEQ ID NO:6) linker from the C-terminal of CD94 to the N-terminal of NKG2A. The constructs allow folding of the CD94/NKG2A into an active conformation and permit dimerization of the Fc part.

3) Single-chain CD94/NKG2-Fc: A stable single-chain Fc-fusion protein comprising extracellular domains of CD94 and an NKG2 protein that are, e.g., interlinked by a serine-glycine-spacer, and/or fused or conjugated to an Fc-sequence. The protein can be produced and secreted from mammalian cells and purified by a single-step affinity-chromatography. In one exemplary embodiment, a soluble receptor Fc-fusion protein can be illustrated by FIG. 3, where linkage between the various segments in the fusion protein is obtained via glycine-serine linkers.

As described in Examples 18 and 19, soluble CD94/NKG2A receptors bound soluble HLA-E, as well as MAb's specific for CD94 (HP-3D9) and NKG2A (Z199), indicating that they were properly folded. The soluble CD94/NKG2A receptors tested appeared stable, since they, with few exceptions, were capable of binding soluble HLA-E tetramers, HP3D9 (Anti-CD94) and anti-NKG2A (Z199) after storage at 4° C. or −20° C. in PBS for, in some cases, several weeks. Further, as described in Examples 20 and 21, a soluble CD94/NKG2C receptors were prepared, and were found capable of binding to an anti-NKG2C-specific antibody.

The heterodimeric receptor constructs of the invention comprises soluble parts of each monomeric subunit and at least one polypeptide comprising all or part of an immunoglobulin heavy-chain constant domain (i.e., an Fc domain).

Typical heterodimeric receptors on which the present principles can be applied include, but are not limited to, the CD94/NKG2A, CD94/NKG2B, CD94/NKG2C, CD94/NKG2E, and CD94/NKG2F receptor. The NKG2 family of receptors have a high sequence homology, as shown in FIG. 25. Suitable soluble portions of the monomeric subunits of these receptors for use in the constructs of the present invention can be known from scientific literature, or deduced using standard computerized analysis of amino acid sequence using publicly available computer-based algorithms such as TMHMM (available at the world-wide web (www) address cbs.dtu.dk/services/TMHMM/).

CD94 (Uniprot accession No. Q13241) comprises 179 amino acids in 3 domains, a cytoplasmic region comprising residues 1-10, a transmembrane region comprising residues 11-31, and an extracellular region comprising residues 32-179, of the following sequence:

(SEQ ID NO: 2)
MAVFKTTLWRLISGTLGIICLSLMATLGILLKNSFTKLSIEPAFTPGPNI

ELQKDSDCCSCQEKWVGYRCNCYFISSEQKTWNESRHLCASQKSSLLQLQ

NTDELDFMSSSQQFYWIGLSYSEEHTAWLWENGSALSQYLFPSFETFNTK

NCIAYNPNGNALDESCEDKNRYICKQQLI.

One exemplary heterodimeric receptor is the CD94/NKG2A receptor. NKG2A (Uniprot accession No. P26715) comprises 233 amino acids in 3 domains, with a cytoplasmic domain comprising residues 1-70, a transmembrane region comprising residues 71-93, and an extracellular region comprising residues 94-233, of the following sequence:

(SEQ ID NO: 1)
MDNQGVIYSDLNLPPNPKRQQRKPKGNKSSILATEQEITYAELNLQKASQ

DFQGNDKTYHCKDLPSAPEKLIVGILGIICLILMASVVTIVVIPSTLIQR

HNNSSLNTRTQKARHCGHCPEEWITYSNSCYYIGKERRTWEESLLACTSK

NSSLLSIDNEEEMKFLSIISPSSWIGVFRNSSHHPWVTMNGLAFKHEIKD

SDNAELNCAVLQVNRLKSAQCGSSIIYHCKHKL.

Another exemplary heterodimeric receptor is the CD94/NKG2C receptor. The NKG2C sequence (SEQ ID NO:3) comprises 231 amino acids in similar arrangement as described for NKG2A. FIG. 25 shows an alignment between the extracellular portions of hNKG2A and hNKG2C.

As described above, other NKG2 receptors may also be applied to construct heterodimeric receptors according to the invention. In such constructs, one monomer unit comprises a soluble segment of a CD94 sequence, and one monomer unit comprises a soluble segment of an NKG2 sequence from, e.g., human NKG2B (SEQ ID NO:70), NKG2E (SEQ ID NO:4), or NKG2F (SEQ ID NO:5).

Several non-human orthologs to NKG2A and CD94 are known that may also be used in the preparation of soluble CD94/NKG2A receptors. Non-limiting orthologues of human NKG2A include those having UNIPROT accession numbers Q95MI5 (UNIPROT-ID:NKG2A_PANTR (Chimpanzee)); Q9MZJ3 (UNIPROT-ID:NKG2A_MACMU (Rhesus macaque)); Q68VD2 (UNIPROT-ID:Q68VD2_MACFA (Cynomolgus monkey)); O54872 (UNIPROT-ID:O54872_RAT (Rat)); and Q9WU31 (UNIPROT-ID:Q9WU31_MOUSE (Mouse)). Non-limiting orthologues of human CD94 include those having UNIPROT accession numbers Q9MZ41 (UNIPROT-ID:KLRD1_PANTR (Chimpanzee)); Q8MHY9 (UNIPROT-ID:KLRD1_PONPY (Orangutan)); Q9MZK9 (UNIPROT-ID:KLRD1_MACMU (Rhesus macaque)); Q68VD4 (UNIPROT-ID:Q68VD4_MACFA (Cynomolgus monkey)); O35778 (UNIPROT-ID:O35778_RAT (Rat)); O54708 (UNIPROT-ID:O54708_MOUSE (Mouse)); and Q38HS3 (UNIPROT-ID:Q38HS3_CANFA (Dog)). These sequences are publicly available at the Uniprot website (World-wide Web address ebi.uniprot.org/index.shtml).

The immunoglobulin polypeptide of the constructs of the invention may comprise a full-length or fragment of an immunoglobulin Fc-portion, or a variant thereof. In one aspect, the immunoglobulin is a wild-type sequence of an Fc-domain, or a fragment thereof. In another aspect, the variant is designed to promote heterodimerization of the two different fusion proteins, resulting in a soluble-receptor complex where fusion protein sS1-Fc1 is fused with sS2-Fc2. In another aspect, the variant is designed to promote heterodimerization of two different single-chain single-chain receptors as described herein.

In particular aspects, the immunoglobulin heavy-chain constant domain are derived from human or non-human mammalian antibodies. In one embodiment, the constant domain is derived from a human IgG1. In another embodiment, the constant domain is derived from a human IgG4. In other aspects, the constant domain is derived from a non-human (e.g., a primate or rodent) IgG molecule (or antibody type that is recognized as being substantially similar to a human IgG in terms of composition). The phrase "derived from", in this context refers to a polypeptide identical (100%) or highly similar in terms of amino acid sequence composition (e.g., at least about 80%, at least about 85%, at least about 90%, at least about 95%, 96%, 97%, 98%, or 99% identical) to a wild-type or reference ("parent") immunoglobulin constant domain, other than any indicated changes (e.g., the below-described substitutions). The phrase "derived from" is, in this sense, not intended to indicate the method by which such an antibody or antibody fragment is generated, which may be by any suitable method, such as recombinant expression, chemical protein synthesis, etc.

In one embodiment, the portion of the Fc domain is of sufficient size and composition that it increases the in vivo half-life of the construct (e.g., due to slower clearance from the circulation) as compared to a construct lacking the Fc domain; in still another particular aspect the portion of the Fc domain is functional (i.e., imparts antibody effector function to the construct antibody)).

Exemplary wild-type immunoglobulin constant domains for use in the present constructs include SEQ ID NO:25, representing a murine Fc (mFc) sequence (clone #669: IMAGE3491766); residues Val98 to Lys324 of SEQ ID NO:21, representing a murine IgG1 sequence; residues Pro100 to Lys330 of SEQ ID NO:20, representing a human IgG1 Fc sequence; and residues Glu99 to Lys327of SEQ ID NO:24, representing a human IgG4 Fc sequence. Corresponding immunoglobulin polypeptides from other wild-type sequences (e.g., SEQ ID NOS: 12-19 and 21-23) can be made using established methods in the art.

In one aspect, the invention provides mutated versions of such wild-type immunoglobulin constant domains. It has now been discovered that pairs of amino acids in the constant domains of antibody monomers are significantly involved in the multimerization and stability of such antibody monomers (and antibody molecules as a whole in the case of antibody molecules such as IgG molecules) and can, accordingly, be modified by various methods, so as to better promote the formation of bispecific antibody monomers or molecules. Typically, such pairs of amino acids are primarily found in the heavy chains of antibody molecules (e.g., between certain amino acid residues present in the CH1 and CH3 constant regions of an IgG molecule).

For example, for human immunoglobulin G antibodies, it has been discovered that ionic forces, which contribute to cross-linking the two heavy chain ("HC") polypeptides of the tetrameric antibody molecule, are contributed mainly by six amino acids present in the CH3 region of the antibody in the following manner: E240-K253, D282-K292, and K322-D239 (sequence position numbers refer to the amino acid starting from the beginning of CH1 (similar to UNIPROT entry IGHG1_HUMAN (SEQ ID NO:20)).

Applying this discovery to the present invention, by substituting HC amino acids of an immunoglobulin peptide conjugated, fused, or linked to a soluble segment of a first subunit of a heterodimeric receptor antigen as follows—K253E, D282K, and K322D, it is possible to significantly reduce the homodimerization or "self-pairing" of the final polypeptide (which normally occurs in the original wild-type tetrameric antibody molecule). By similarly modifying the HC sequence of a second immunoglobulin polypeptide conjugated, linked, or fused to a soluble segment of a second subunit of a heterodimeric receptor by the substitutions D239K, E240K, and K292D, homodimerization of such polypeptides is also reduced or abolished.

Co-expressing the two polypeptides, each containing soluble segment from a different heterodimeric receptor subunit, can "restore" stabilizing ionic interactions (e.g., E240-

K253, D282-K292, and K322-D239) and pairing of the polypeptides, resulting in generation of a soluble heterodimeric receptor. Table 1 summarizes (in exemplary fashion) these various substitutions. Corresponding mutation sites in other exemplary constant domains can be derived by alignment (see example in FIG. 7) with human IgG1 (SEQ ID NO:20). For example, as shown in Table 1, at numbers above residue 103, the IgG4 residue corresponding to an IgG1 residue can be obtained by subtracting 3.

The Fc-domain of the constructs of the invention may comprise one, two or all of the mutation pairs in Table 1. Thus, in one non-limiting embodiment, a heterodimeric construct of the invention comprises a first variant Fc-domain comprising a lysine (K) at a residue corresponding to residue 239 in SEQ ID NO:20 and an aspartic acid (D) at a residue corresponding to residue 292 in SEQ ID NO:20, and a second variant Fc-domain comprising a lysine at a residue corresponding to residue 282 in SEQ ID NO:20 and an aspartic acid (D) at a residue corresponding to residue 322 in SEQ ID NO:20. This type of construct may be referred to as "double-mutation" construct herein. In another non-limiting embodiment, a heterodimeric construct of the invention comprises a first variant Fc-domain comprising lysine (K) at residues corresponding to residues 239 and 240 in SEQ ID NO:20 and an aspartic acid (D) at a residue corresponding to residue 292 in SEQ ID NO:20, and a second variant Fc-domain comprising a glutamic acid (E) at a residue corresponding to residue 253 in SEQ ID NO:20, a lysine at a residue corresponding to residue 282 in SEQ ID NO:20 and an aspartic acid (D) at a residue corresponding to residue 322 in SEQ ID NO:20. Additionally or alternatively, one or more mutation pairs may be combined with other mutation pairs. One exemplary alternative or additional mutation pair is T243Y, Y284T, referring to residue positions in SEQ ID NO: 21 (IGHG1_MOUSE).

TABLE 1

Exemplary amino acid substitution in constant domains of human IgG1 or IgG4, referring to SEQ ID NO: 20 (UniProt IGHG1_HUMAN) or SEQ ID NO: 24 (UniProt IGHG4_HUMAN), respectively.

| Antibody 1 | | Antibody 2 | |
|---|---|---|---|
| CH3 mutations | | | |
| IgG1: | IgG4: | IgG1: | IgG4: |
| K253E | K250E | E240K | E236K |
| D282K | D279K | K292D | E237K |
| K322D | K319D | D239K | R289D |
| CH1 mutations | | | |
| | K96E | | |

As described herein, various wild-type or variant murine Fc domains can also be used in the heterodimeric constructs according to the invention. FIG. 8 describes some of the murine wild-type or variant Fc domains used in preparing constructs in the Examples.

In the heterodimeric receptors of the invention, different segments of a polypeptide can be linked using a variety of conventional methods. In exemplary embodiments, a soluble portion of a subunit of a heterodimeric receptor is linked to an immunoglobulin polypeptide (e.g., sS1-linker-Fc or sS2-linker-Fc), or a soluble portion of a first subunit to a soluble portion of a second subunit (e.g., sS1-linker-sS2-Fc, sS2-linker-sS1-Fc, sS1-linker1-sS2-linker2-Fc, sS2-linker1-sS1-linker2-Fc). Different segments can be linked by, e.g., (1) chemical cross-linking; (2) affinity association by appending a moiety, such as a peptide, to soluble receptor segments and/or immunoglobulin polypeptide segments, and then joining the segments via the appended moiety or moieties to form a hybrid protein; and (3) linking soluble receptor segments and/or immunoglobulin polypeptide segments to form a single polypeptide chain via a polypeptide linker, i.e., a fusion protein.

In the first linkage category, any of a variety of conventional methods can be used to chemically couple (cross-link) two polypeptide chains. Covalent binding can be achieved either by direct condensation of existing side chains (e.g., the formation of disulfide bond between cysteine residues, such as may naturally occur between the soluble portions of the CD94 and NKG2 subunits in certain CD94/NKG2 receptors) or by the incorporation of external bridging molecules. Many bivalent or polyvalent agents are useful in coupling polypeptides.

In general, the cross-linking agents used are bifunctional agents reactive, e.g., with epsilon-amino group or thiol groups. These cross-linkers can be classified into two categories: homo- and hetero-bifunctional reagents. Homobifunctional reagents can react, e.g., with free thiols (e. g., generated upon reduction of disulfide bonds), and include, e.g., 5,5'-Dithiobis-(2-nitrobenzoic acid) (DNTB), and o-phenylenedimaleimide (O-PDM), which can form a thioether bond between two polypeptides having such free thiols. Heterobifunctional reagents can introduce a reactive group onto a polypeptide that will enable it to react with a second polypeptide. For example, N-succinimidyl-3-(2-pyridyldithio) propionate (SPDP) can react with a primary amino group to introduce a free thiol group. Other chemical cross-linking agents include, e.g., carbodiimides, diisocyanates, diazobenzenes, hexamethylene diamines, dimaleimide, glutaraldehyde, 4succinimidyl-oxycarbonyl-a-methyl a(2-pyridylthio) toluene(SMPT) and N-succinimidyl-S-acetyl-thioacetate (SATA). Procedures for cross-linking polypeptides with such agents are well-known in the art. See, e.g., Pierce Immuno-Technology Catalog & Handbook (1991) E8-E39; Karpovsky et al., J. Exp. Med. 1984;160:1686 et seq.; Liu et al. Proc. Natl. Acad. Sci. 1985;82:8648 et seq.; and U.S. Pat. No. 4,676,980.

Spacer arms between the two reactive groups of cross-linkers may have various lengths and chemical compositions. A longer spacer arm allows a better flexibility of the conjugated polypeptides. while some particular components in the bridge (e.g., a benzene group) may lend extra stability to the reactive groups or an increased resistance of the chemical link to the action of various aspects (e.g., disulfide bond resistance to reducing reagents). The use of peptide spacers such as the peptide linkers or linker peptides described below is also contemplated.

In the second category of linkage methods, conventional methods can be used to append any of a variety of moieties (e.g., peptides) to soluble receptor portions and/or immunoglobulin polypeptides, thereby generating hybrid or fusion proteins which then can be associated via the appended moieties.

In one embodiment, moieties such as biotin and avidin (streptavidin) are bound or complexed to soluble receptor portions and/or immunoglobulin polypeptides, and these moieties interact to associate the two subunits.

In another embodiment, the appended moieties are both peptides, which may herein be referred to as "dimerization-promoting peptides." Among the wide variety of such peptide linkers that can be used are the GST (glutathione S-transferase) fusion protein, or a dimerization motif thereof; a PDZ dimerization domain; FK-506 BP (binding protein) or a dimerization motif thereof; a natural or artificial helix-turnhelix dimerization domain of p53; and Protein A or its dimerization domain, domain B. In one embodiment, the appended peptides are components of a leucine zipper. The leucine zipper moieties are often taken from the human transcription factors c-jun and c-fos.

The dimerization-promoting peptide should provide an adequate degree of flexibility to prevent the two subunits from interfering with each others' activity, for example by steric hindrance, and to allow for proper protein folding. Therefore, it may be desirable to modify a dimerization-promoting peptide by altering its length, amino acid composition, and/or conformation, e.g., by appending to it still other "secondary linker moieties" or "hinge moieties." Among the many types of secondary linker moieties are, e.g., tracts of small, preferably neutral and either polar or nonpolar, amino acids such as, e.g., glycine, serine, threonine or alanine, at various lengths and combinations; polylysine; or the like. Alternatively, multiples of linkers and/or secondary linker moieties can be used. It is sometimes desirable to use a flexible hinge region, such as, e.g., the hinge region of human IgG, or polyglycine repeats interrupted by serine or threonine at certain intervals.

The length and composition of a dimerization-promoting peptide can readily be selected by one of skill in the art in order to optimize the desired properties of the soluble receptor, e.g., its ability to bind to its ligand. A conventional assay for binding to antibodies is described in the Examples.

The peptides can be appended to soluble receptor portions and immunoglobulin poypeptides by a variety of methods which will be evident to one of ordinary skill in the art, e.g., chemical coupling as described above (if necessary, following derivatization of appropriate amino acid groups); attachment via biotin/avidin interactions; covalent joining of the polypeptides by art-recognized methods (e.g., using appropriate enzymes); recombinant methods; or combinations thereof.

In the third linkage category, soluble receptor portions and/or immunoglobulin polypeptides are covalently linked via a peptide linker. In this category, recombinant techniques are used to join soluble portions of each of two segments, in frame, to form a single chain polypeptide molecule. Preferably, the receptor portions are separated from one another by a linker peptide, of any length or amino acid composition, most preferably a flexible loop structure, which allows the two receptor moieties to lie at an appropriate distance from each other and in a proper alignrunent for optimal. interaction, Typical linker peptides contain tracts of small, preferably neutral and either polar or nonpolar amino acids such as, e.g., glycine, serine, threonine or alanine, at various lengths and combinations; polylysine; or the like. The peptide linker can have at least one amino acid and may have 500 or more amino acids. Preferably, the linker is less than about 100 amino acids, more preferably about 2 to 30, most preferably about 3-10 amino acids. Flexible linker domains, such as the hinge region of human IgG, or polyglycine repeats interrupted by serine or threonine at certain intervals, can be used, alone or in combination with other moieties. Exemplary linkers are those based on combinations of glycine (G), serine (S), and/or arginine (R), including, but not limited to, GS, GSS, GGSGGS (SEQ ID NO:6), and GGSGGSRSS (SEQ ID NO:7). In one embodiment, the linker linking the first and second subunits in a single-chain heterodimeric receptor is GGSGGS (SEQ ID NO:6). In another embodiment, the linker linking the first and second subunits in a single-chain heterodimeric receptor is GGSGGSRSS (SEQ ID NO:7).

Recombinant methods which can be used to generate such linear, single chain heterodimeric receptors are conventional.

Furthermore, routine procedures can be used to select linker peptides and to optimize parameters so that the two soluble receptor portions are aligned at a distance and in an orientation which allow optimal function of the soluble, heterodimeric receptor. See, e.g., U.S. Pat. Nos. 4,935,233 and 4,751,180.

Of course, two subunits can be associated via any combination of the above moieties, e.g., a tandem arrangement in any relative order or orientation.

Thus, in one aspect, the present invention provides isolated nucleic acids that encode a soluble heterodimeric receptor polypeptide, with isolated nucleic acids encoding a polypeptide comprising a soluble portion of at least one monomeric receptor subunit, and at least one nucleic acid encoding an immunoglobulin peptide. In one embodiment, one nucleic acid encodes an NKG2 subunit (e.g., an NKG2A, NKG2B, NKG2C, NKG2E, or NKG2F subunit) and an immunoglobulin polypeptide, one nucleic acid encodes a CD94 subunit and an immunoglobulin polypeptide, and the heterodimeric receptor encoded binds to an antibody against the corresponding CD94/NKG2 receptor or a natural ligand of the CD94/NKG2 receptor. For example, one nucleic acid can encode an NKG2A subunit and an immunoglobulin peptide, one nucleic acid can encode a CD94 polypeptide and an immunoglobulin peptide, and the heterodimeric receptor encoded can bind to a CD94/NKG2A ligand such as HLA-E or an antibody against a CD94/NKG2A receptor, e.g., human CD94/NKG2A receptor. In another embodiment, a single isolated nucleic acid encodes a single-chain heterodimeric receptor comprising both an NKG2 subunit, a CD94 subunit, and an immunoglobulin subunit, where the heterodimeric receptor encoded binds to a CD94/NKG2 ligand such as HLA-E or an antibody against a CD94/NKG2 receptor. For example, a single isolated nucleic acid can encode a single-chain heterodimeric receptor comprising both an NKG2A (or NKG2C) subunit, a CD94 subunit, and an immunoglobulin subunit, where the heterodimeric receptor encoded binds to HLA-E or an antibody against the CD94/NKG2A (or CD94/NKG2C) receptor.

Of the above-described nucleic acids, one nucleic acid can encode a soluble portion of the NKG2A receptor set forth in SEQ ID NO:1, or a variant or ortholog thereof. In one embodiment, the nucleic acid encodes a soluble portion of the NKG2A subunit comprising residues 116-233 of SEQ ID NO:1. In another embodiment, the nucleic acid encodes a soluble portion of the NKG2A subunit comprising residues 99-233 of SEQ ID NO:1. In another embodiment, the nucleic acid encodes a fragment of the NKG2A subunit which begins with a residue selected from residues 99-116 and ends at residue 116 of SEQ ID NO.1. In another embodiment, the nucleic acid encodes a soluble portion of the NKG2A subunit consisting of residues 116-233 of SEQ ID NO:1. In another embodiment, the nucleic acid encodes a soluble portion of the NKG2A subunit consisting of residues 99-233 of SEQ ID NO:1.

In one embodiment, the nucleic acid encodes a soluble portion of the NKG2C subunit comprising residues 114-231 of SEQ ID NO:3. In another embodiment, the nucleic acid encodes a soluble portion of the NKG2C subunit comprising residues 97-231, e.g., 96-231, of SEQ ID NO:3. In another embodiment, the nucleic acid encodes a fragment of the NKG2C subunit which begins with a residue selected from residues 96-114 and ends at residue 114 of SEQ ID NO.3. In another embodiment, the nucleic acid encodes a soluble portion of the NKG2A subunit consisting of residues 114-231 of SEQ ID NO:3. In another embodiment, the nucleic acid encodes a soluble portion of the NKG2A subunit consisting of residues 96-231 of SEQ ID NO:3. One nucleic acid can also or alternatively encode a soluble portion of the CD94 receptor set forth in SEQ ID NO:2. In one embodiment, the nucleic acid encodes a soluble portion of the CD94 subunit comprising residues 58-179 of SEQ ID NO:2. In another embodiment, the nucleic acid encodes a soluble portion of the CD94 subunit comprising residues 35-179 of SEQ ID NO:2. In another embodiment, the nucleic acid encodes a fragment of the CD94 subunit which begins with a residue selected from residues 35-58 and ends at residue 179 of SEQ ID NO:2. In another embodiment, the nucleic acid encodes a soluble portion of the CD94 subunit consisting of residues 58-179 of SEQ ID NO:2. In another embodiment, the nucleic acid encodes a soluble portion of the CD94 subunit consisting of residues 35-179 of SEQ ID NO:2.

The nucleic acids of the invention may also encode additional features of the heterodimeric receptor construct, such as peptide linkers, multimerization domains, affinity tags, etc. For example, the nucleic acids may further encode one or more peptide linkers linking a soluble portion of a subunit of a heterodimeric receptor to an immunoglobulin polypeptide (e.g., sS1-linker-Fc or sS2-linker-Fc), or a soluble portion of a first subunit to a soluble portion of a second subunit (e.g., sS1-linker-sS2-Fc, sS2-linker-sS1-Fc, sS1-linker1-sS2-linker2-Fc, sS2-linker1-sS1-linker2-Fc). Exemplary linkers are those based on combinations of glycine (G), serine (S), and/or arginine (R), including, but not limited to, GS, GSS, GGSGGS (SEQ ID NO:6), and GGSGGSRSS (SEQ ID NO:7). In one embodiment, the linker linking the first and second subunits in a single-chain heterodimeric receptor is GGSGGS (SEQ ID NO:6). In another embodiment, the linker linking the first and second subunits in a single-chain heterodimeric receptor is GGSGGSRSS (SEQ ID NO:7).

In another embodiment, the nucleic acids of the expression vectors encode one or more secretory signal sequences, In one embodiment, the signal sequence is MPLLLLLPLLWA-GALAMD (SEQ ID NO:30).

The nucleic acids may also encode one or more cleavage sites, particularly between different segments in a fusion protein. See, e.g., Tuan et al., Connective Tissue Research 1996; 34:1-9.

In one aspect, the invention provides a nucleic acid encoding an amino acid sequence at least 90%, 95%, 96%, 97%, 98%, 99%, or 100% identical to an amino acid sequence listed in Table 2 with or without signal (Sig) sequences, as well as expression vectors and host cells comprising such nucleic acids. In another aspect, the invention provides variants of the amino acid sequences in Table 2. In a preferred embodiment, the encoded variant binds a natural ligand of the human CD94/NKG2A receptor, or an antibody raised against the human CD94/NKG2A receptor. In another preferred embodiment, the encoded variant binds a natural ligand of the human CD94/NKG2C receptor, or an antibody raised against the human CD94/NKG2C receptor

TABLE 2

Amino acid sequences of exemplary soluble CD94/NKG2A receptor constructs (Sig = signal sequence; mFc = murine Fc-portion; GS, GSS etc. = linkers based on glycine (G), serine (S), and arginine (R)). The Fc domain nomenclature refers to the designation in FIG. 8.

| Designation/Description | SEQ ID NOS: |
|---|---|
| CD94-mFc/NKG2A heterodimer (Sig)-(mFc)-GSS-(CD94)/(Sig)-(mFc)-GS-(NKG2A) | 31/32 |

TABLE 2-continued

Amino acid sequences of exemplary soluble CD94/NKG2A receptor constructs (Sig = signal sequence; mFc = murine Fc-portion; GS, GSS etc. = linkers based on glycine (G), serine (S), and arginine (R)). The Fc domain nomenclature refers to the designation in FIG. 8.

| Designation/Description | SEQ ID NOS: |
|---|---|
| CD94-mFc/NKG2A heterodimer with single mutation (Sig)-(mFc-sm-CD94)-GSS-(CD94)/(Sig)-(mFc-sm-NKG2A)-GS-(NKG2A) | 33/34 |
| CD94-mFc/NKG2A heterodimer with double mutation (Sig)-(mFc-dm-CD94)-GSS-(CD94)/(Sig)-(mFc-dm-NKG2A)-GS-(NKG2A) | 35/36 |
| NKG2A-CD94 single-chain hexaHis-GST NKG2A-2xGGS-CD94 | 37 |
| NKG2A-CD94 single-chain Trx-hexaHis-NKG2A-2xGGS-CD94 | 38 |
| CD94-NKG2A-mFc single-chain (Sig)-(mFc)-GS-(NKG2A)-GGS-GGS-RSS-(CD94) | 39 |
| CD94-NKG2C-mFc single chain (Sig)-(mFc)-GS-(NKG2A)-GGS-GGS-RSS-(CD94) | 59 |

In another aspect, the present invention provides a first expression vector comprising the following operably linked elements: (a) a transcription promoter; a first nucleic acid encoding a first subunit of a soluble portion of a heterodimeric receptor fused to an immunoglobulin polypeptide; and a transcription terminator; and a second expression vector comprising the following operably linked elements: (b) a second transcription promoter; a second nucleic acid encoding a second subunit of a soluble portion of a heterodimeric receptor fused to an immunoglobulin polypeptide; and a transcription terminator. In another aspect, the first and second nucleic acids are contained within a single expression vector, optionally in-frame. In another aspect, the expression vector comprises the following operably linked elements: (a) a transcription promoter; a first nucleic acid encoding a single-chain soluble heterodimeric receptor; and a transcription terminator. In one embodiment of any of the preceding aspects, the expression vector further encodes linker sequences, affinity tags, or secretory signal sequence operably linked to or comprised in the nucleic acid. In another embodiment of the preceding aspects, the heterodimeric receptor is a human CD94/NKG2 receptor. In another embodiment of the preceding aspects, the heterodimeric receptor is the human CD94/NKG2A receptor. In another embodiment of the preceding aspects, the heterodimeric receptor is the human CD94/NKG2C receptor.

In another aspect, the present invention provides a cultured cell comprising at least one of the expression vectors described above, wherein the cell expresses the polypeptides encoded by the expression vector. A single cell may contain, e.g., an expression vector encoding a single subunit of a soluble heterodimeric receptor fused to an immunoglobulin polypeptide (endoding, e.g., sS1-Fc or sS2-Fc), an expression vector encoding both first and second subunits of a soluble heterodimeric receptor, each fused to an immunoglobulin polypeptide (encoding, e.g., sS1-Fc and sS2-Fc), or an expression vector encoding a single-chain heterodimeric receptor comprising first and second subunits of a heterodimeric receptor and an immunoglobulin polypeptide (e.g., sS1-sS2-Fc or sS2-sS1-Fc).

The invention also provides methods of producing soluble heterodimeric receptors by transfecting host cells with such expression vectors, and expressing one or more nucleic acids in a cell or cell culture. In one embodiment, the cultured cell comprises an expression vector as disclosed above, wherein the first and second nucleic acids are located on the same expression vector, and the cell expresses the polypeptides encoded by the expression vector. In another embodiment, the cultured cell comprises expression vectors where the first and second nucleic acids are located on independent expression vectors and are co-transfected into the cell, and cell expresses the polypeptides encoded by the nucleic acids. In another embodiment, a first host cell is transfected with an expression vector encoding a first nucleic acid per above, and a second host cell (of the same or different type) is transfected with a nucleic acid encoding a second nucleic acid per above, and the first and second host cells separately express the polypeptides encoded by the nucleic acids. In another embodiment, the cultured cell comprises an expression vector as disclosed above, wherein the cell expresses a single-chain heterodimeric or multimeric soluble receptor polypeptide encoded by the nucleic acid. In another embodiment, the cultured cell secretes a monomeric fusion protein of a soluble portion of a heterodimeric receptor subunit and an immunoglobulin peptide. In another embodiment, the cultured cell secretes a soluble heterodimeric receptor polypeptide heterodimer or multimeric complex. In another embodiment, the cultured cell secretes a soluble CD94/NKG2 receptor that binds a CD94/NKG2 ligand or an antibody against the CD94/NKG2 receptor. In another embodiment, the cultured cell secretes a soluble CD94/NKG2A receptor that binds a CD94/NKG2A ligand or an antibody against CD94/NKG2A. In another embodiment, the cultured cell secretes a soluble CD94/NKG2C receptor that binds a CD94/NKG2C ligand or an antibody against CD94/NKG2C.

In one embodiment, the present invention provides a method of producing a soluble heterodimeric receptor polypeptide that forms a heterodimeric or multimeric complex comprising: culturing a cell as disclosed above; and isolating the soluble receptor polypeptides produced by the cell. In another embodiment, the present invention provides a method of producing a soluble heterodimeric receptor comprising: co-culturing a first cell expressing a soluble portion of a first subunit of a heterodimeric receptor linked to a first immunoglobulin polypeptide and a second cell expressing a soluble portion of a second subunit of a heterodimeric receptor linked to a second immunoglobulin polypeptide, and isolating soluble heterodimeric polypeptides formed in the culture media. In another embodiment, the present invention provides a method of producing a soluble heterodimeric receptor comprising: separately culturing a first cell expressing a soluble portion of a first subunit of a heterodimeric receptor linked to a first immunoglobulin polypeptide and a second cell expressing a soluble portion of a second subunit of a heterodimeric receptor linked to a second immunoglobulin polypeptide, separately purifying the first and second subunit fusion proteins, mixing the first and second subunit fusion proteins, and isolating soluble heterodimeric polypeptides formed. The isolating steps described above may comprise one or more purification steps according to known methods in the art.

In one aspect, the invention provides isolated soluble heterodimeric receptors comprising at least one hybrid protein, i.e., a protein where two polypeptides (typically fusion polypeptides comprising at least a receptor and an immunoglobulin segment and/or another dimerization-promoting peptide) are linked via an interaction other than a peptide bond (e.g., disulfide bonding, avidin-biotin, leucine zipper, etc.). In this method, the polypeptides are separately produced by recombinant methods, and thereafter joined.

If desired, the relative amounts of two recombinant fusion proteins produced in a single cell or cell culture can be regulated, e.g., by expressing them from promoters of different strengths. For example, if the appended peptide of a first subunit A forms homodimers at a high frequency, whereas the appended peptide of a second subunit B forms homodimers at a low frequency, one can drive the formation of the desired heterodimers by expressing much higher levels of subunit B than of A. The optimal relative amounts can be determined empirically by routine experimentation.

In another aspect, the invention provides isolated soluble heterodimeric receptors encoded by the nucleic acids described above. In one embodiment, the isolated soluble heterodimeric receptor polypeptide comprises two polypeptides, the first comprising a soluble portion of a first subunit of a heterodimeric receptor linked to an immunoglobulin polypeptide, and the second comprising a second subunit of a heterodimeric receptor linked to an immunoglobulin polypeptide. The first and second polypeptides are preferably associated, e.g., via ionic forces, covalent bonds, or a combination thereof. In soluble heterodimeric receptors comprising at least two polypeptides, the polypeptides can be associated by disulfide bonding between the receptor subunit portions or the immunoglobulin portions, and/or forced interaction via mutations in one immunoglobulin segment, as described herein. In one embodiment, one polypeptide comprises an NKG2 subunit (e.g. NKG2A, NKG2B, NKG2C, NKG2E, or NKG2F) and an immunoglobulin peptide, one polypeptide comprises a CD94 polypeptide and an immunoglobulin peptide, and the heterodimeric receptor formed binds to a CD94/NKG2 ligand such as, e.g., an antibody against the corresponding CD94/NKG2 receptor, or a natural ligand, e.g., HLA-E in the case of CD94/NKG2A, CD94/NKG2C etc. In another embodiment, the heterodimeric receptor is a single-chain polypeptide comprising soluble portions of first and second subunits of a heterodimeric receptor and an immunoglobulin polypeptide. In the case of heterodimeric NKG2 receptors, the heterodimeric receptor encoded can bind to an antibody against a CD94/NKG2 receptor, e.g., a human CD94/NKG2 receptor, or a natural ligand, e.g., HLA-E in the case of NKG2A, NKG2C etc.

The heterodimeric receptor can comprise a soluble portion of the NKG2A sequence set forth in SEQ ID NO:1, or a variant or ortholog thereof. In one embodiment, the soluble portion of the NKG2A subunit comprises residues 116-233 of SEQ ID NO:1. In another embodiment, the soluble portion of the NKG2A subunit comprises residues 99-233 of SEQ ID NO:1. In another embodiment, the soluble portion comprises a fragment of the NKG2A subunit which begins with a residue selected from residues 99-116 and ends at residue 116 of SEQ ID NO:1. In another embodiment, the soluble portion of the NKG2A subunit consists of residues 116-233 of SEQ ID NO:1. In another embodiment, the soluble portion of the NKG2A subunit consists of residues 99-233 of SEQ ID NO:1.

The heterodimeric receptor may also or alternatively comprise a soluble portion of the NKG2C sequence set forth in SEQ ID NO:3. In one embodiment, the NKG2C subunit comprises residues 114-231 of SEQ ID NO:3. In another embodiment, the soluble portion of the NKG2C subunit comprises residues 97-231, e.g., 96-231, of SEQ ID NO:3. In another embodiment, the soluble portion comprises a fragment of the NKG2C subunit which begins with a residue selected from residues 96-114 and ends at residue 114 of SEQ ID NO:3. In another embodiment, the soluble portion of the NKG2A subunit consists of residues 114-231 of SEQ ID NO:3. In another embodiment, the soluble portion of the NKG2A subunit consists of residues 96-231 of SEQ ID NO:3.

The heterodimeric receptor may also or alternatively comprise a soluble portion of NKG2B, NKG2E, comprising, e.g., the segment aligned with NKG2A-residues 99-233.

The heterodimeric receptor can comprise a soluble portion of the CD94 receptor set forth in SEQ ID NO:2, or a variant or ortholog thereof. In one embodiment, the soluble portion of the CD94 subunit comprises residues 58-179 of SEQ ID NO:2. In another embodiment, the soluble portion of the CD94 subunit comprises residues 34-179 or 35-179 of SEQ ID NO:2. In another embodiment, the soluble portion comprises a fragment of the CD94 subunit which begins with a residue selected from residues 34-58 and ends at residue 179 of SEQ ID NO:2. In another embodiment, the soluble portion of the CD94 subunit consists of residues 58-179 of SEQ ID NO:2. In another embodiment, the soluble portion of the CD94 subunit consists of residues 35-179 of SEQ ID NO:2.

In one aspect, the invention provides polypeptides having amino acid sequences at least 90%, 95%, 96%, 97%, 98%, 99%, or 100% identical to an amino acid sequence listed in Table 1, as well as pharmaceutical compositions comprising such polypeptides. In another aspect, the invention provides heterodimeric receptors comprising variants of the amino acid sequences in Table 2. In one embodiment, the variant binds a natural ligand of a human CD94/NKG2 receptor such as HLA-E and/or an antibody raised against a human CD94/NKG2A receptor. The variant may differ from the parent in, e.g., conservative amino acid substitutions, as described above, non-conservative amino acid substitutions, additions, and/or deletions. For example, essential amino acids in the receptor polypeptides of the present invention can be generated and identified according to procedures known in the art, such as site-directed mutagenesis or alanine-scanning mutagenesis (Cunningham and Wells, Science 1989;244: 1081-1085; Bass et al., Proc. Natl. Acad. Sci. USA 1991;88: 4498-4502). In the latter technique, single alanine mutations are introduced at every residue in the molecule, and the resultant mutant molecules are tested for biological activity (e.g., ligand binding and signal transduction) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., Science 1992; 255:306-312; Smith et al., J. Mol. Biol. 1992;224:899-904; Wlodaver et al., FEBS Lett. 1992;309:59-64. The identities of essential amino acids can also be inferred from analysis of homologies with related receptors.

Multiple amino acid substitutions can be made and tested using known methods of mutagenesis and screening, such as those disclosed by Reidhaar-Olson and Sauer Science 1988; 241:53-57 or Bowie and Sauer Proc. Natl. Acad. Sci. USA 1989;86:2152-2156. Briefly, these authors disclose methods for simultaneously randomizing two or more positions in a polypeptide, selecting for functional polypeptide, and then sequencing the mutagenized polypeptides to determine the spectrum of allowable substitutions at each position. Other methods that can be used include phage display e.g., Lowman et al., Biochem. 1991;30:10832-10837; Ladner et al., U.S. Pat. No. 5,223,409; Huse, WIPO Publication WO 92/06204, and region directed mutagenesis (Derbyshire et al., Gene 46:145, (1986); Ner et al., DNA 7:127, (1988)). Mutagenesis methods as disclosed above can be combined with high throughput screening methods to detect activity of cloned, mutagenized receptors in host cells. Preferred assays in this regard include cell proliferation assays and biosensor-based ligand-binding assays, which are described below. Mutagenized DNA molecules that encode active heterodimeric receptors or portions thereof (e.g., ligand-binding fragments) can be recovered from the host cells and rapidly sequenced using modem equipment. These methods allow the rapid determination of the importance of individual amino acid residues in a polypeptide of interest, and can be applied to polypeptides of unknown structure.

The following describes some additional exemplary aspects of the invention:

In one aspect, the invention provides a single-chain soluble CD94/NKG2 receptor comprising a soluble portion of an NKG2 amino acid sequence and a soluble portion of a CD94 amino acid sequence. The single-chain construct may, in one aspect, further comprise an immunoglobulin polypeptide comprising all or part of an Fc domain or variant thereof. Thus, the invention also provides a single-chain soluble CD94/NKG2 receptor comprising a soluble portion of an NKG2 amino acid sequence, a soluble portion of a CD94 amino acid sequence, and an immunoglobulin polypeptide comprising all or part of an Fc domain or variant thereof. In one embodiment, in the single-chain soluble CD94/NKG2 receptor, the C-terminal of the soluble portion of a CD94 amino acid sequence can be linked to the N-terminal of the soluble portion of an NKG2 amino acid sequence, and the C-terminal of the soluble portion of an NKG2 amino acid sequence is linked to the immunoglobulin polypeptide. In another embodiment, in the single-chain soluble CD94/NKG2 receptor, the C-terminal of the soluble portion of an NKG2 amino acid sequence is linked to the N-terminal of the soluble portion of a CD94 amino acid sequence, and the C-terminal of the soluble portion of a CD94 amino acid sequence is linked to the immunoglobulin polypeptide. In the single-chain soluble CD94/NKG2 receptor, the soluble portion of an NKG2 amino acid sequence, the soluble portion of a CD94 amino acid sequence, and, in embodiments comprising an immunoglobulin polypeptide, the immunoglobulin polypeptide, can be associated by, e.g., covalently linkage. For example, the soluble portion of an NKG2 amino acid sequence and soluble portion of a CD94 amino acid sequence can be linked by a peptide linker comprising glycine and serine.

In another aspect, the invention provides a single-chain soluble CD94/NKG2A receptor comprising a soluble portion of an NKG2A amino acid sequence and a soluble portion of a CD94 amino acid sequence. The single-chain construct may, in one aspect, further comprise an immunoglobulin polypeptide comprising all or part of an Fc domain or variant thereof. Thus, the invention also provides a single-chain soluble CD94/NKG2A receptor comprising a soluble portion of an NKG2A amino acid sequence, a soluble portion of a CD94 amino acid sequence, and an immunoglobulin polypeptide comprising all or part of an Fc domain or variant thereof. In one embodiment, in the single-chain soluble CD94/NKG2A receptor, the C-terminal of the soluble portion of a CD94 amino acid sequence can be linked to the N-terminal of the soluble portion of an NKG2A amino acid sequence, and the C-terminal of the soluble portion of an NKG2A amino acid sequence is linked to the immunoglobulin polypeptide. In another embodiment, in the single-chain soluble CD94/NKG2A receptor, the C-terminal of the soluble portion of an NKG2A amino acid sequence is linked to the N-terminal of the soluble portion of a CD94 amino acid sequence, and the C-terminal of the soluble portion of a CD94 amino acid sequence is linked to the immunoglobulin polypeptide. In the single-chain soluble CD94/NKG2A receptor, the soluble portion of an NKG2A amino acid sequence, the soluble portion of a CD94 amino acid sequence, and, in embodiments comprising an immunoglobulin polypeptide, the immunoglobulin polypeptide, can be associated by, e.g., covalently linkage. For example, the soluble portion of an NKG2A amino acid sequence and soluble portion of a CD94 amino acid sequence can be linked by a peptide linker comprising glycine and serine.

In another aspect, the invention provides a single-chain soluble CD94/NKG2C receptor comprising a soluble portion of an NKG2C amino acid sequence and a soluble portion of a CD94 amino acid sequence. The single-chain construct may, in one aspect, further comprise an immunoglobulin polypeptide comprising all or part of an Fc domain or variant thereof. Thus, the invention also provides a single-chain soluble CD94/NKG2C receptor comprising a soluble portion of an NKG2C amino acid sequence, a soluble portion of a CD94 amino acid sequence, and an immunoglobulin polypeptide comprising all or part of an Fc domain or variant thereof. In one embodiment, in the single-chain soluble CD94/NKG2C receptor, the C-terminal of the soluble portion of a CD94 amino acid sequence can be linked to the N-terminal of the soluble portion of an NKG2C amino acid sequence, and the C-terminal of the soluble portion of an NKG2C amino acid sequence is linked to the immunoglobulin polypeptide. In another embodiment, in the single-chain soluble CD94/NKG2C receptor, the C-terminal of the soluble portion of an NKG2C amino acid sequence is linked to the N-terminal of the soluble portion of a CD94 amino acid sequence, and the C-terminal of the soluble portion of a CD94 amino acid sequence is linked to the immunoglobulin polypeptide. In the single-chain soluble CD94/NKG2C receptor, the soluble portion of an NKG2C amino acid sequence, the soluble portion of a CD94 amino acid sequence, and, in embodiments comprising an immunoglobulin polypeptide, the immunoglobulin polypeptide, can be associated by, e.g., covalently linkage. For example, the soluble portion of an NKG2C amino acid sequence and soluble portion of a CD94 amino acid sequence can be linked by a peptide linker comprising glycine and serine.

In another aspect, the invention provides a dimer of any single-chain soluble CD94/NKG2, CD94/NKG2A or CD94/NKG2C receptor described above.

In another aspect, the invention provides a soluble CD94/NKG2 receptor comprising an NKG2 subunit comprising a soluble portion of an NKG2 amino acid sequence and a CD94 subunit comprising a soluble portion of an CD94 amino acid sequence, wherein at least one of the NKG2 subunit and CD94 subunit comprises an immunoglobulin polypeptide comprising all or part of an Fc domain or variant thereof, wherein non-limiting examples of NKG2 subunits are NKG2A and NKG2C. The immunoglobulin polypeptide may, for example, comprise a portion of an IgG Fc domain which increases the in vivo half-life of the construct. In one embodiment, the immunoglobulin polypeptide is a functional Fc domain. In another embodiment, the Fc domain is from an IgG4 antibody. In yet another embodiment, the Fc domain is from an IgG1 antibody.

In another aspect, only one of the NKG2 and CD94 subunits is linked to an immunoglobulin polypeptide. The immunoglobulin polypeptide can, for example, be linked to the C-terminal portion of the subunit. In one embodiment, the NKG2 and CD94 subunits are linked via a peptide linker. For example, the peptide linker may comprise the sequence GGSGGS (SEQ ID NO:6) or GGSGGSRSS (SEQ ID NO:7). In a particular embodiment, the NKG2A subunit is covalently bound to the immunoglobulin polypeptide. In an alternative embodiment, the CD94 subunit is covalently bound to the immunoglobulin polypeptide.

In another aspect, each of the NKG2 and CD94 subunits is covalently bound to an immunoglobulin polypeptide. For example, the N-terminal of the NKG2 subunit can be linked to the C-terminal of a first immunoglobulin polypeptide so as to form a first polypeptide, and the N-terminal of the CD94 subunit can be linked to the C-terminal of a second immunoglobulin polypeptide so as to form a second polypeptide. In one embodiment, both the first and second immunoglobulin polypeptides are variants of a human IgG1 Fc domain, the first immunolobulin polypeptide comprising substitutions corresponding to K253E, D282K, and K322D, and the second immunoglobulin polypeptide comprising substitutions corresponding to D239K, E240K, and K292D, or vice versa. In another embodiment, both the first and second immunoglobulin polypeptides are variants of a human IgG4 Fc domain, the first immunolobulin polypeptide comprising substitutions corresponding to K250E, D279K, and K319D, and the second immunoglobulin polypeptide comprising substitutions corresponding to E236K, E237K, R289D, or vice versa.

In any of the preceding aspects, the NKG2 subunit can be NKG2A wherein the NKG2A amino acid sequence can be, for example, that of human NKG2A (SEQ ID NO:1). For example, the NKG2A subunit may comprise residues 99-233 of SEQ ID NO: 1.

In any of the preceding aspects, the NKG2 subunit can alternatively be NKG2C wherein the NKG2C amino acid sequence can be, for example, that of human NKG2C (SEQ ID NO:3). For example, the NKG2C subunit may comprise residues 96-231 of SEQ ID NO:3.

In any of the preceding aspects, the CD94 amino acid sequence can be SEQ ID NO:2. For example, the CD94 subunit may comprise residues 35-179 of SEQ ID NO:2.

In any of the preceding aspects, the immunoglobulin polypeptide may comprise full-length or fragment of a sequence selected from SEQ ID NOS:12-29. A heterodimeric construct comprising a full-length or fragment of each of SEQ ID NOS:12-29 is a specific and separate embodiment according to the invention.

In any of the preceding aspects, the immunoglobulin polypeptide can be covalently bound to a signal sequence. For example, the signal sequence may comprise the sequence of SEQ ID NO:30.

In additional or alternative aspects, the invention provides soluble CD94/NKG2A receptor comprising the sequences of SEQ ID NOS:31 and 32; SEQ ID NOS:33 and 34; SEQ ID NOS:35 and 36; SEQ ID NO:37; SEQ ID NO:38, and SEQ ID NO:39 or a soluble CD94/NKG2C receptor comprising SEQ ID NO:59.

In another aspect, the invention provides nucleic acids encoding the soluble CD94/NKG2 receptor of any of the preceding aspects. Also provided for is a cell transformed with an expression vector comprising such nucleic acids, where the cell may be, e.g., a prokaryotic cell or eukaryotic cell. Also provided for is a method of producing a soluble CD94/NKG2 receptor, comprising culturing such a cell under conditions suitable for expression of the soluble CD94/NKG2 receptor.

In another aspect, the invention provides for a pharmaceutical composition comprising an effective amount of the soluble CD94/NKG2 receptor of any of the preceding aspects, and a pharmaceutically acceptable carrier or excipient.

In another aspect, the invention provides for a method of producing an antibody against a CD94/NKG2 receptor such as, e.g., CD94/NKG2A, the method comprising: inoculating an animal with a soluble CD94/NKG2 receptor of any of the preceding aspects, wherein the polypeptide elicits an immune response in the animal to produce the antibody; and isolating the antibody from the animal.

Preparation of Soluble Heterodimeric Receptors

The heterodimeric receptor polypeptides of the present invention can be produced in genetically engineered host cells according to conventional techniques.

Suitable host cells are those cell types that can be transformed or transfected with exogenous DNA and grown in culture, and include bacteria, fungal cells, and cultured higher eukaryotic cells. Eukaryotic cells, particularly cultured cells of multicellular organisms, are preferred. Techniques for manipulating cloned DNA molecules and introducing exogenous DNA into a variety of host cells is disclosed by Sambrook et al., Molecular Cloning: A Laboratory Manual, 2nd ed., Cold Spring Harbor Laboratory Press, Cold Spring Harbor, N.Y., (1989), which is incorporated herein by reference.

In general, a DNA sequence encoding a soluble heterodimeric receptor polypeptide is operably linked to other genetic elements required for its expression, generally including a transcription promoter and terminator, within an expression vector. The vector will also commonly contain one or more selectable markers and one or more origins of, replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers. Multiple components of a soluble receptor complex can be co-transfected on individual expression vectors or be contained in a single expression vector. Such techniques of expressing multiple components of protein complexes are well known in the art.

To direct a heterodimeric receptor polypeptide into the secretory pathway of a host cell, a secretory signal sequence (also known as a leader sequence, prepro sequence or pre sequence) can be provided in the expression vector. The secretory signal sequence may be that of the receptor, or may be derived from another secreted protein (e.g., t-PA) or synthesized de novo. The secretory signal sequence is joined to the heterodimeric receptor polypeptide DNA sequence in the correct reading frame. Secretory signal sequences are commonly positioned 5' to the DNA sequence encoding the polypeptide of interest, although certain signal sequences may be positioned elsewhere in the DNA sequence of interest (see, e.g., Welch et al., U.S. Pat. No. 5,037,743; Holland et al., U.S. Pat. No. 5,143,830).

Cultured mammalian cells are preferred hosts within the present invention.

Methods for introducing exogenous DNA into mammalian host cells include calcium phosphate-mediated transfection (Wigler et al., Cell 1 1978;4:725 et seq.; Corsaro and Pearson, Somatic Cell Genetics 1981;7:603 et seq.: Graham and Van der Eb, Virology 1973;52:456 et seq., electroporation (Neumann et al., EMBO J. 1982;1:841-845), DEAE dextran mediated transfection (Ausubel et al., eds., Current Protocols in Molecular Biology, (John Wiley and Sons, Inc., N.Y., 1987), and liposome-mediated transfection (Hawley-Nelson et al., Focus 1993;15:73 et seq.; Ciccarone et al., Focus 1993;15:80 et seq.), which publications are incorporated herein by reference. The production of recombinant polypeptides in cultured mammalian cells is disclosed, for example, by Levinson et al., U.S. Pat. No. 4,713,339; Hagen et al., U.S. Pat. No. 4,784, 950; Pahniter et al., U.S. Pat. No. 4,579,821; and Ringold, U.S. Pat. No. 4,656,134. Suitable cultured mammalian cells include the COS-1 (ATCC No. CRL 1650), COS-7 (ATCC No. CRL 1651), BHK (ATCC No. CRL 1632), BHK 570 (ATCC No. CRL 10314),293 (ATCC No. CRL 1573; Graham et al., J. Gen. Virol. 36:59-72, 1977) and Chinese hamster ovary (e.g. CHO-K1; ATCC No. CCL 61) cell lines. In one embodiment, the cell is dependent upon an exogenously supplied hematopoietic growth factor for its proliferation. Preferred cell lines of this type are the human TF-1 cell line (ATCC number CRL-2003) and the AML-193 cell line (ATCC number CRL-9589), which are GM-CSF-dependent human leukemic cell lines and BaF3 (Palacios and Steinmetz, Cell 41: 727-734, (1995)) which is an IL-3 dependent murine pre-B cell line. Additional suitable cell lines are known in the art and available from public depositories such as the American Type Culture Collection, Rockville, Md. In general, strong transcription promoters are preferred, such as promoters from SV40 or cytomegalovirus. See, e.g., U.S. Pat. No. 4, 956,288. Other suitable promoters include those from metallothionein genes (U.S. Pat. Nos. 4, 579,821 and 4,601,978) and the adenovirus major late promoter.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neornycin-type drug, such as G418 or the like. Selection systems may also be used to increase the expression level of the gene of interest, a process referred to as "amplification."

Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate. Other drug resistance genes (e.g. hygromycin resistance, multidrug resistance, puromycin acetyltransferase) can also be used.

Other higher eukaryotic cells can also be used as hosts, including insect cells, plant cells and avian cells. Transformation of insect cells and production of foreign polypeptides therein is disclosed by Guarino et al., U.S. Pat. No. 5,162,222; Bang et al., U.S. Pat. No. 4,775,624; and WIPO publication WO 94/06463, which are incorporated herein by reference. The use of Agrobacteriuin rhizogenes as a vector for expressing genes in plant cells has been reviewed by Sinkar et al., J. Biosci. (Bangalore) 11:47-58, (1987).

Fungal cells, including yeast cells, and particularly cells of the genus *Saccharomyces*, can also be used within the present invention, such as for producing fusion polypeptides. Methods for transforming yeast cells with exogenous DNA and producing recombinant polypeptides therefrom are disclosed by, for example, Kawasaki, U.S. Pat. No. 4,599,311; Kawasaki et al., U.S. Pat. No. 4,931,373; Brake, U.S. Pat. No. 4,870,008; Welch et al., U.S. Pat. No. 5,037,743; and Murray et al., U.S. Pat. No. 4,845,075. Transformed cells are selected by phenotype determined by the selectable marker, commonly drug resistance or the ability to grow in the absence of a particular nutrient (e.g., leucine). A preferred vector system for use in yeast is the POT1 vector system disclosed by Kawasaki et al. (U.S. Pat. No. 4,931,373), which allows transformed cells to be selected by growth in glucose containing media. Suitable promoters and terminators for use in yeast include those from glycolytic enzyme genes (see, e.g., Kawasaki, U.S. Pat. No. 4,599,311; Kingsman et al., U.S. Pat. No. 4,615,974; and Bitter, U.S. Pat. No. 4,977, 092) and alcohol dehydrogenase genes. See also U.S. Pat. Nos. 4,990, 446; 5,063,154; 5,139,936 and 4,661,454. Transformation systems for other yeasts, including *Hansenula polymorpha, Schizosaccharomyces ponibe, Kluyveroinyces lactis, Kluyveromyces fragilis, Ustilago maydis, Pichia pastoris, Pichia methanolica, Pichia guillennondii* and *Candida maltosa* are known in the art. See, for example, Gleeson et al., J. Gen. Microbiol. 1986;132:3459-3465 and Cregg, U.S. Pat. No. 4,882,279. *Aspergillus* cells may be utilized according to the methods of McKnight et al., U.S. Pat. No. 4,935,349. Methods for transforming *Acreinonium chrysogenum* are disclosed by Sumino et al., U.S. Pat. No. 5,162,228. Methods for transforming *Neurospora* are disclosed by Lainbowitz, U.S. Pat. No. 4,486,533.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

Preferably, a soluble heterodimeric receptor of the invention is "isolated," e.g., is in a form other than it occurs in nature, for example in a buffer, in a dry form awaiting reconstitution, as part of a kit or a pharmaceutical composition, etc. The term "isolated polypeptide" refers to a soluble heterodimeric receptor of the present invention that (1) has been separated from at least about 50 percent of polynucleotides, lipids, carbohydrates or other materials (i.e., contaminants) with which it is naturally associated. Preferably, the isolated polypeptide is substantially free from any other contaminating polypeptides or other contaminants that are found in its natural environment which would interfere with its therapeutic, diagnostic, prophylactic or research use.

A variety of conventional methods can be used to isolate and/or purify a soluble heterodimeric receptor of the invention, or to isolate and/or purify its different polypeptide components prior to joining them. Soluble receptors of the invention and/or their subunits can be recovered from cells either as soluble proteins (preferably after having been secreted into the culture fluid) or as inclusion bodies, from which they may be extracted quantitatively, e.g., by 8M guanidium hydrochloride and dialysis. Conventional purification methods which can be used include, e.g., ion exchange chromatography, hydrophobic interaction chromatography, reverse phase chromatography, and/or -gel filtration. In a preferred embodiment, affinity chromatography is used, e.g., with a column containing protein A or protein G, which can bind to the Fc moieties present in certain soluble receptors. In another embodiment, each polypeptide is "tagged" with a moiety, preferably a cleavable one, that can bind to an appropriate affinity column. For example, one or both subunits can be tagged with poly His (e.g., H'S6) to allow rapid purification by metal-chelate chromatography; with a Strep-tag which binds to streptavidin and can be eluted with iminobiotin; with maltose binding protein (MBP), which binds to ainylose and can be eluted with maltose; or with any other such moiety which can be separated by affinity chromatography. Alternatively, one can tag one or both of the subunits with epitopes to which antibodies are available, such as the FLAGO peptide, Asp-Tyr-Lys-Asp-Asp-Asp-Asp-Lys (available from Eastman Kodak Co., Scientific Imaging Systems Division, New Haven, Conn.). For typical methods of using affinity tags, see, e.g., Recombinant Protein Protocols: Detection and Isolation, Edited by Rocky S. Tuan, Methods in Molecular Biology, Vol. 63, Humana Press, 1997 and Examples 5 and 6.

Combinations of any of the above types of purification methods can also be used.

The purity of the receptors can be determined using standard methods including, e.g., polyacrylamide gel electrophoresis, column chromatography, and amino-terminal amino acid sequence analysis.

Binding of the soluble heterodimeric receptors to, e.g., a natural ligand of the heterodimeric receptor or an antibody against the native heterodimeric receptor can be by assessed by conventional methods. A preferred assay system employing a ligand-binding receptor construct uses a commercially available biosensor instrument (BIAcoreTm, Pharmacia Biosensor, Piscataway, N.J.), wherein the ligand, an antibody, or a fragment thereof is immobilized onto the surface of a receptor chip. Use of this instrument is disclosed by Karlsson, J. Immunol. Methods 145:229-240, (1991) and Cunningham and Wells, J. Mol. Biol. 234:554-563, (1993). The ligand, antibody, or fragment is covalently attached, using amine or sulfhydryl chemistry, to dextran fibers that are attached to gold film within the flow cell. A test sample is passed through the cell. If the soluble heterodimeric receptor construct in the sample binds the ligand or antibody, it will bind to the immobilized ligand or antibody, causing a change in the refractive index of the medium, which is detected as a change in surface plasmon resonance of the gold film. This system allows the determination of on- and off-rates, from which binding affinity can be calculated, and assessment of stoichiometry of binding.

Ligand-binding receptor polypeptides can also be evaluated by other assay systems known in the art. Such systems include Scatchard analysis for determination of binding affinity. See, Scatchard, Ann. NY Acad. Sci. 1949;51: 660-672, and calorimetric assays (Cunningham et al., Science 1991; 253:545-548; Cunningham et al., Science 1991;254:821-825).

The stability of the receptor can be tested by storing it under different conditions (e.g., temperature, pH, in different buffers) for various lengths of time. Functional stability is then tested by analyzing the binding capacity. For example, soluble CD94/NKG2A or CD94/NKG2C can be tested for its capacity to bind its ligand (HLA-E) or specific anti-CD94/NKG2A or CD94/NKG2C antibodies (e.g. Z199, Z270, HP-3D9, FAB138P) in a BiaCore or similar assay after storage for various periods of time and under different storage conditions. The percentage of binding of a stored CD94/NKG2 in comparison with a reference soluble CD94/NKG2 (which may, e.g., have been stored under standard conditions) can be a measure of its stability.

Use Soluble Heterodimeric Receptors

Particular aspects of the invention relate to the use of the soluble heterodimeric receptor constructs as immunization agents, research and selection tools, diagnostic reagents, and therapeutic agents.

In one aspect, the invention provides a method for immunizing an animal with a soluble heterodimeric receptor according to the invention in order to elicit an antibody response against the heterodimeric receptor. Exemplary advantages of using the soluble heterodimeric receptor constructs of the invention instead of soluble fragments alone include longer half-life, correct three dimensional folding of the receptor and an efficient take-up in APC's facilitated by the Fc tag (thus promoting a more robust antibody response. Antibodies against the heterodimeric receptor can then be harvested from blood (polyclonal antibody preparation) or prepared from antibody-producing B cells using hybridoma techniques or other establish technologies for monoclonal antibody production. In one embodiment, the present invention provides a method of producing an antibody to a soluble heterodimeric receptor comprising: immunizing an animal with a soluble heterodimeric receptor described herein, wherein the polypeptide elicits an immune response in the animal to produce the antibody; and isolating the antibody from the animal.

In another aspect, the present invention provides an antibody produced by the method as disclosed above, which specifically binds to a soluble heterodimeric or multimeric receptor complex comprising a soluble heterodimeric receptor as described herein. In one embodiment, the antibody disclosed above is a monoclonal antibody.

The step of immunizing a non-human mammal with an antigen may be carried out in any manner well known in the art for stimulating the production of antibodies in a mouse (see, for example, E. Harlow and D. Lane, Antibodies: A Laboratory Manual., Cold Spring Harbor Laboratory Press, Cold Spring Harbor, N.Y. (1988)). The soluble heterodimeric receptor, or a fragment thereof, is suspended or dissolved in a buffer, optionally with an adjuvant, such as complete Freund's adjuvant. Methods for determining the amount of immunogen, types of buffers and amounts of adjuvant are well known to those of skill in the art. These parameters may be different for different immunogens, but are easily elucidated.

Similarly, the location and frequency of immunization sufficient to stimulate the production of antibodies are also well known in the art. In a typical immunization protocol, the non-human animals are injected intraperitoneally with antigen on day 1 and again about a week later. This is followed by recall injections of the antigen around day 20, optionally with adjuvant such as incomplete Freund's adjuvant. The recall injections are performed intravenously and may be repeated for several consecutive days. This is followed by a booster injection at day 40, either intravenously or intraperitoneally, typically without adjuvant. This protocol results in the production of antigen-specific antibody-producing B cells after about 40 days. Other protocols may also be utilized as long as they result in the production of B cells expressing an antibody directed to the antigen used in immunization.

For polyclonal antibody preparation, serum is obtained from an immunized non-human animal and the antibodies present therein isolated by well-known techniques. The serum may be affinity purified using any of the immunogens set forth above linked to a solid support so as to obtain antibodies that react with the soluble heterodimeric receptor or cells expressing the native heterodimeric receptor.

For monoclonal antibodies production, a non-human mammal is immunized with any soluble heterodimeric receptor described herein, including any full-length sequence, any extracellular sequence, or any fragment thereof. Splenocytes are then isolated and subsequently fused with an immortalized cell to form an antibody-producing hybridoma. The isolation of splenocytes from a non-human mammal is well-known in the art and typically involves removing the spleen from an anesthetized non-human mammal, cutting it into small pieces and squeezing the splenocytes from the splenic capsule and through a nylon mesh of a cell strainer into an appropriate buffer so as to produce a single cell suspension. The cells are washed, centrifuged and resuspended in a buffer that lyses any red blood cells. The solution is again centrifuged and remaining lymphocytes in the pellet are finally resuspended in fresh buffer.

Once isolated and present in single cell suspension, the lymphocytes are fused to an immortal cell line. This is typically a mouse myeloma cell line, although many other immortal cell lines useful for creating hybridomas are known in the art. Preferred murine myeloma lines include, but are not limited to, those derived from MOPC-21 and MPC-11 mouse tumors available from the Salk Institute Cell Distribution Center, San Diego, Calif. U.S.A., or X63 Ag8653 and SP-2 cells available from the American Type Culture Collection, Rockville, Md. U.S.A. The fusion is effected using polyethylene glycol or the like. The resulting hybridomas are then grown in selective media that contains one or more substances that inhibit the growth or survival of the unfused, parental myeloma cells. For example, if the parental myeloma cells lack the enzyme hypoxanthine guanine phosphoribosyl transferase (HGPRT or HPRT), the culture medium for the hybridomas typically will include hypoxanthine, aminopterin, and thymidine (HAT medium), which substances prevent the growth of HGPRT-deficient cells.

The hybridomas are typically grown on a feeder layer of macrophages. The macrophages are preferably from littermates of the non-human mammal used to isolate splenocytes and are typically primed with incomplete Freund's adjuvant or the like several days before plating the hybridomas. Fusion methods are described in (Goding, "Monoclonal Antibodies: Principles and Practice," pp. 59-103 (Academic Press, 1986)).

The cells are allowed to grow in the selection media for sufficient time for colony formation and antibody production; usually between 7 and 14 days. The hybridoma colonies are then assayed for the production of antibodies that bind the soluble heterodimeric receptor or cells expressing the native heterodimeric receptor. The assay is typically a calorimetric ELISA-type assay, although several other types of assays may be employed, including immunoprecipitation, radioimmunoassay, Biacore assays (see above), or Scintillation Proximity assays (SPA), as well known in the art. The wells positive for the desired antibody production are examined to determine if one or more distinct colonies are present. If more than one colony is present, the cells may be recloned and grown to ensure that only a single cell has given rise to the colony producing the desired antibody. Positive wells with a single apparent colony are typically re-cloned and re-assayed to insure only one monoclonal antibody is being detected and produced.

Hybridomas that are confirmed to be producing a monoclonal antibody of this invention are then grown up in larger amounts in an appropriate medium, such as DMEM or RPMI-1640. Alternatively, the hybridoma cells can be grown in vivo as ascites tumors in an animal.

After sufficient growth to produce the desired monoclonal antibody, the growth media containing monoclonal antibody (or the ascites fluid) is separated away from the cells and the monoclonal antibody present therein is purified. Purification is typically achieved by chromatography using protein A or protein G-Sepharose, or an anti-mouse 1 g linked to a solid support such as agarose or Sepharose beads (all described, for example, in the Antibody Purification Handbook, Amersham Biosciences, publication No. 18-1037-46, Edition AC, the disclosure of which is hereby incorporated by reference). The bound antibody is typically eluted from protein A/protein G columns by using low pH buffers (glycine or acetate buffers of pH 3.0 or less) with immediate neutralization of antibody-containing fractions. These fractions are pooled, dialyzed, and concentrated as needed.

Alternatively, the DNA encoding an antibody of the invention is isolated from the hybridoma, placed in an appropriate expression vector for transfection into an appropriate host. The host is then used for the recombinant production of the antibody, or variants thereof, such as a humanized version of that monoclonal antibody, active fragments of the antibody or chimeric antibodies comprising the antigen-recognition portion of the antibody.

In an additional or alternative aspect of the invention, the soluble receptors of the invention such as e.g., soluble CD94/NKG2 receptors, can be used in methods for selecting NKG2-binding and/or CD94-binding agents for therapeutic or diagnostic applications. For example, one or more single-chain soluble CD94/NKG2 receptors may be used in such methods, such as, e.g., single-chain CD94/NKG2A, single-chain CD94/NKG2C, single-chain CD94/NKG2B, single-chain CD94/NKG2E and/or single-chain CD94/NKG2F. Exemplary agents include, but are not limited to, antibodies against CD94, NKG2A, NKG2B, NKG2C, NKG2E, and/or NKG2F as well as antigen-binding fragments or derivatives of such antibodies. For exemplary antibody fragments, see, e.g., Holliger and Hudson (Nat Biotechnol 2005;23:1126-1136).

In one embodiment, the invention thus provides for a method of producing an anti-NKG2 antigen-binding compound, comprising: (a) providing an antigen-binding compound that specifically binds to an NKG2 polypeptide; (b) testing the antigen-binding compound for binding to a soluble CD94/NKG2A receptor described herein; (c) selecting the antigen-binding compound if it is determined that the antigen-binding compound binds to the soluble CD94/NKG2A receptor; and (d) optionally, producing a quantity of the selected antigen-binding compound.

In another embodiment, the invention provides for a method of producing an anti-NKG2 antigen-binding compound, the method comprising: (a) producing a quantity of an antigen-binding compound that specifically binds to an NKG2 polypeptide; (b) testing a sample from said quantity of an antigen-binding compound for binding to a soluble CD94/NKG2 receptor described herein; (c) selecting the quantity for use as a medicament and/or in the manufacture of a medicament if it is determined that the antigen-binding compound binds to the soluble CD94/NKG2 receptor; and (d) optionally, preparing the quantity for administration to a human, optionally formulating a quantity of the selected antigen-binding compound with a pharmaceutically acceptable carrier.

In another embodiment, the invention provides for a method of producing an anti-NKG2 antigen-binding compound, the method comprising: (a) providing a plurality of antigen-binding compounds that specifically bind to an NKG2 polypeptide, (b) testing each of the antigen-binding compounds for binding to a soluble CD94/NKG2 receptor described herein; (c) selecting an antigen-binding compound if it is determined that the antigen-binding compound binds to said soluble CD94/NKG2 receptor; and (d) optionally, making the antigen-binding compound suitable for human administration; and/or (e) optionally, producing a quantity of the selected antigen-binding compound.

The above methods may also comprise making the antigen-binding compound human-suitable by, e.g., making the antigen-binding compound chimeric or humanized. The above methods may also comprise producing a quantity of antigen-binding compound comprises culturing a cell expressing the antigen-binding compound in a suitable medium and recovering the antigen-binding compound. In specific embodiments, the antigen-binding compound in the above methods may comprise an antibody or an antigen-binding fragment thereof. The NKG2 polypeptide may be selected from, e.g., NKG2A, NKG2B, NKG2C, NKG2E, and/or NKG2F. For example, the antigen-binding compound may bind to one or more of NKG2A, NKG2B, NKG2C, NKG2E, and NKG2F. In a specific embodiment, the anti-gen-binding compound binds at least NKG2A. In another specific embodiment, the antigen-binding compound binds at least NKG2C.

The invention also relates to methods of detecting HLA-E molecules (in, e.g., experimental or diagnostic assays), comprising contacting a sample which may contain HLA-E molecules with a soluble heterodimeric receptor according to the invention. In one embodiment, the soluble heterodimeric receptor is a single-chain CD94/NKG2A or CD94/NKG2C receptor construct as described herein. The soluble heterodimeric receptor may be labeled with a conventional detectable moiety used for such purposes, e.g., a radioactive or fluorescent entity. Alternatively, indirect methods such as, e.g., conjugating the soluble heterodimeric receptor to an enzyme capable of converting a non-detectable substrate to a detectable product, or a secondary antibody against an Fc-portion of the soluble heterodimeric receptor, may be used. Such assays can, of course, be quantitative. In one embodiment, such an assay is used to determine whether a biological sample taken from a patient contains cells that express HLA-E at the cell surface. In another embodiment, such an assay is used to determine whether an agent of interest causes an increase or decrease in a cell of the amount of HLA-E which is available for binding to CD94/NKG2A or CD94/NKG2C (e.g., human or murine cells; in a test tube, tissue sample, in culture, or in an animal) and/or whether it modulates (inhibits or enhances) the biological activity of HLA-E (e.g., its binding to a soluble receptor). Exemplary biological samples include, but are not limited to, tumor samples obtained by, e.g., biopsy or surgery; and blood samples.

In another aspect, the invention provides a method for specifically targeting HLA-E expressing or HLA-E over-expressing cells in a subject by administering a soluble heterodimeric receptor according to the invention. The Fc-portion of the soluble CD94/NKG2A or CD94/NKG2C can then function as effector domain to induce cytolysis of the HLA-E expressing cell via a CDC and/or an ADCC response.

In another aspect, a soluble heterodimeric receptor is used for purification of a receptor ligand or an antibody against the native receptor. The soluble heterodimeric receptor is immobilized on a solid support, such as beads of agarose, cross-linked agarose, glass, cellulosic resins, silica-based resins, polystyrene, cross-linked polyacrylamide, or like materials that are stable under the conditions of use. The soluble heterodimeric receptor may also be attached via its Fc-portion to, e.g., a Protein A or Protein G affinity column. Methods for linking polypeptides to solid supports are known in the art, and include amine chemistry, cyanogen bromide activation, N-hydroxysuccinimide activation, epoxide activation, sulfhydryl activation, and hydrazide activation. The resulting media can generally be configured in the form of a column, and fluids containing ligand are passed through the column one or more times to allow ligand to bind to the receptor. The ligand is then eluted using changes in salt concentration or pH to disrupt ligand-receptor binding.

Cytotoxicity Assays

In a particular embodiment, the invention provides agents such as soluble CD94/NKG2A receptor constructs and antibodies generated against such soluble CD94/NKG2A receptor constructs. To determine whether such constructs or antibodies can reduce or block CD94/NKG2A interactions with HLA-E, and thereby increases the cytotoxicity of CD94/ NKG2A-restricted lymphocytes, the following tests can be performed.

NK cell activity can be assessed using a cell based cytotoxicity assays, e.g., measuring chromium release or other parameter to assess the ability of the antibody to stimulate NK cells to kill target cells such as P815, K562 cells, or appropriate tumor cells as disclosed in Sivori et al., J. Exp. Med. 1997;186:1129-1136; Vitale et al., J. Exp. Med. 1998; 187: 2065-2072; Pessino et al. J. Exp. Med. 1998;188:953-960; Neri et al. Clin. Diag. Lab. Immun. 2001;8:1131-1135; Pende et al. J. Exp. Med. 1999;190:1505-1516, the entire disclosures of each of which are herein incorporated by reference. In one exemplary assay, the ability of an agent to reduce CD94/NKG2A-mediated signalling can be tested in a standard 4-hour in vitro cytotoxicity assay using, e.g., NKL cells that express CD94/NKG2A, and target cells that express HLA-E. Such NKL cells do not efficiently kill targets that express HLA-E because CD94/NKG2A recognizes HLA-E, leading to initiation and propagation of inhibitory signalling that prevents lymphocyte-mediated cytolysis. Such an in vitro cytotoxicity assay can be carried out by standard methods that are well known in the art, as described for example in Coligan et al., eds., Current Protocols in Immunology, Greene Publishing Assoc. and Wiley Interscience, N.Y., (1992, 1993). The target cells are labeled with $^{51}$Cr prior to addition of NKL cells, and then the killing is estimated as proportional to the release of $^{51}$Cr from the cells to the medium, as a result of killing. Addition of an agent that prevents CD94/NKG2A from binding to HLA-E results in prevention of the initiation and propagation of inhibitory signalling via CD94/NKG2A. Therefore, addition of such agents results in increases in lymphocyte-mediated killing of the target cells. This step thereby identifies agents that prevent CD94/NKG2A-induced negative signalling by, e.g., blocking ligand binding. In a particular $^{51}$Cr-release cytotoxicity assay, CD94/NKG2A-expressing NKL effector-cells can kill HLA-E-negative LCL 721.221 target cells, but less efficient HLA-E-expressing LCL 721.221-Cw3 cells. In contrast, YTS effector-cells that lack CD94/NKG2A kill both cell-lines efficiently. Thus, NKL effector cells cannot kill HLA-E+ LCL 721.221-Cw3 cells due to HLA-E-induced inhibitory signalling via CD94/NKG2A. When NKL cells are pre-incubated with blocking anti-CD94/NKG2A antibodies according to the present invention in such a $^{51}$Cr-release cytotoxicity assay, HLA-E-expressing LCL 721.221-Cw3 cells are killed in an antibody-concentration-dependent fashion.

The inhibitory or potentiating activity of a receptor or antibody composition of this invention can be assessed in any of a number of other ways, e.g., by its effect on intracellular free calcium as described, e.g., in Sivori et al., J. Exp. Med. 1997;186:1129-1136, the disclosure of which is herein incorporated by reference.

NK cell activity can also be addressed using a cytokine-release assay, wherein NK cells are incubated with the receptor construct or antibody to stimulate the cytokine production of the NK cells (for example IFN-γ and TNF-α production). In an exemplary protocol, IFN-γ production from PBMC is assessed by cell surface and intracytoplasmic staining and analysis by flow cytometry after 4 days in culture. Briefly, Brefeldin A (Sigma Aldrich) is added at a final concentration of 5 μg/ml for the last 4 hours of culture. The cells are then incubated with anti-CD3 and anti-CD56 mAb prior to permeabilization (IntraPrep™; Beckman Coulter) and staining with PE-anti-IFN-γ or PE-IgG1 (Pharmingen). GM-CSF and IFN-γ production from polyclonal activated NK cells are measured in supernatants using ELISA (GM-CSF: DuoSet Elisa, R&D Systems, Minneapolis, Minn, IFN-: OptEIA set, Pharmingen).

The compounds of this invention, including receptor constructs and antibodies, may exhibit partial inhibitory activity, e.g., partially reduce the CD94/NKG2A-mediated inhibition of NK cell cytotoxicity. In one embodiment, an antibody preparation causes at least a 10% augmentation in NK cytotoxicity, preferably at least a 40% or 50% augmentation in NK cytotoxicity, or more preferably at least a 70% augmentation in NK cytotoxicity. Most preferred compounds are able to inhibit (or stimulate, in the case of activating receptors) at least 20%, preferably at least 30%, 40% or 50% or more of the activity of the NK cell, e.g. as measured in a cell toxicity assay, in comparison to cells in the absence of the compound. Also preferred, the compound can provide an increase of depletion of target cells by 10%, 20%, 30%, 40%, 50%, 60%, 70%, 80%, 90%, 100%, 200%, 300%, 400%, 500%, 1000%, or more relative to the depletion level in the absence of the compound. Alternatively, the compounds of this invention are able to induce the lysis of matched or HLA compatible or autologous target cell population, i.e., cell population that would not be effectively lysed by NK cells in the absence of said antibody. Accordingly, compounds of this invention may also be defined as facilitating NK cell activity in vivo.

Pharmaceutical Compositions

The invention also provides compositions that comprise a soluble heterodimeric receptor or antibody (including fragments and derivatives thereof), in any suitable vehicle in an amount effective to detectably potentiate lymphocyte cytotoxicity in a patient or in a biological sample comprising lymphocytes and, optionally, HLA-E-expressing target cells. The composition further comprises a pharmaceutically acceptable carrier or excipient. Such carriers and excipients are well-known in the art, and are described in, e.g., Remington: The Science and Practice of Pharmacy, 19th edition, 1995.

The term "biological sample" as used herein includes but is not limited to a biological fluid (for example serum, lymph, or blood), cell sample or tissue sample (for example bone marrow).

Further aspects and advantages of this invention will be disclosed in the following experimental section, which should be regarded as illustrative and not limiting the scope of this application.

EXAMPLES

Example 1

Modelling of CD94/NKG2A Interaction with HLA-E

This Example describes in silico modelling identifying CD94/NKG2A segments covering the interaction with HLA-E. The protein data base (PDB; Protein Data Bank) referred to herein is described in: H. M. Berman, J. Westbrook, Z. Feng, G. Gilliland, T. N. Bhat, H. Weissig, I. N. Shindyalov, P. E. Bourne: The Protein Data Bank. Nucleic Acids Research, 28 pp. 235-242 (2000). PDB identifiers are always 4 alphanumeric characters, e.g., 1NKR & 1OM3, sometimes referred to as 1 NKR.pdb & 1OM3.pdb.

Figure 4:
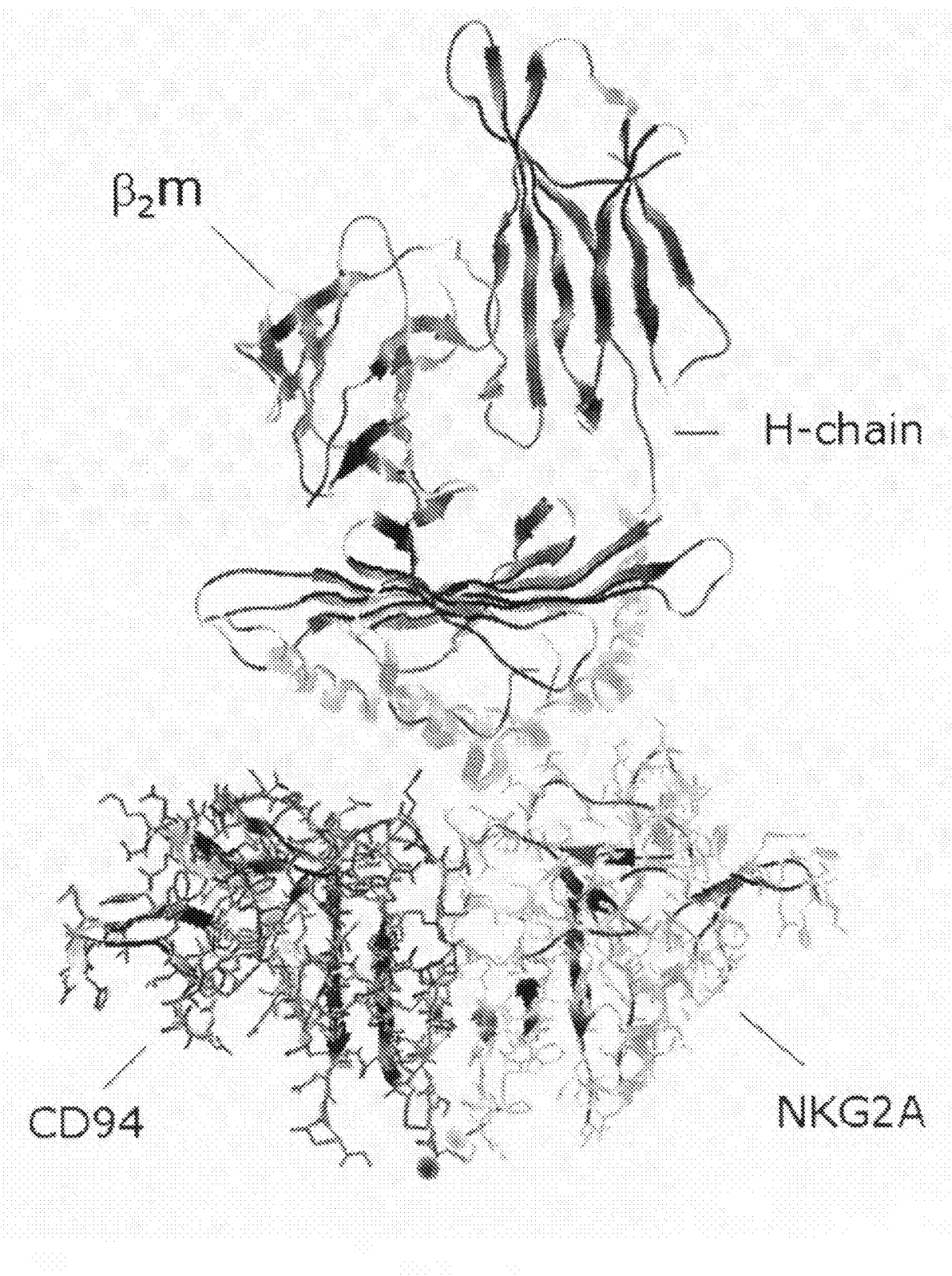
FIG. 4. In silico model of CD94/NKG2A complexed with HLA-E. The model shows that N and C terminals are close together, allowing for several types of constructs.

A model of CD94/NKG2A complexed with its ligand HLA-E was built in silico. For this, a model of the CD94/NKG2A heterodimer was built using the X-ray structure of the CD94 homodimer as a homology model (PDB-ID:1B6E). In addition, the resolved crystal structure of HLA-E was used (PDB-ID:1MHE). The complex of CD94/NKG2A and HLA-E was then built in silico, using the X-ray structure of the related NKG2D-MICA complex (PDB-ID:1HYR). The complete model is shown in FIG. 4.

The model was consistent with mutational studies which identify the HLA-E residues R65, D69, Q72, R75, R79, H155, D162, E166 as the interacting residues (H. Wada et al., Eur. J. Immunol. 2004. 34, 81-90). In the alignment of CD94, NKG2A and NKG2D, the model also identifies a critical residue for pairing with CD94: F107 (CD94), F165 (NKG2A). The corresponding residue is not conserved in NKG2D.

The model also identified that the N- and C-terminals were close together. In the model, shown in FIG. 4, the distance was 13.2 Å between the alpha-carbons of the CD94 C-terminal and the NKG2A N-terminal, and 14.7 Å between alpha carbons of the CD94 N-terminal and the NKG2A C-terminal. By comparison, the length of one amino acid residue is about 3.75 Å, and the length of, e.g., a GGSGGS (SEQ ID NO:6) linker is about 22.5 Å.

Example 2

Identification of Amino Acid Residues Responsible for Ionic Interactions in Immunoglobulins References to heavy chain constant region position numbers here specifically indicate the position of the wild-type constant region sequence starting from the beginning (N-terminus) of CH1 (similar to Uniprot-id:IGHG1_HUMAN (SEQ ID NO:20). For constant light chain positions, numbering is according to Uniprot-id:KAC_HUMAN (SEQ ID NO:10). The amino acids responsible for the ionic interactions in human IgG1 s were identified using an analysis of X-ray structures available for the CH3-CH3 domain-domain interactions of both the GM and KM allotypes, and X-ray structures available for CH1-CKappa and CH1-CLambda interactions.

Specifically, the following KM X-ray structures were analysed: 1HZH, 1ZA6, 1OQX, 1OQO, 1L6X; the following GM X-ray structures were analysed: 1T89, 1T83, 1IIX, 1H3X; the following CH1-Ckappa X-ray structures were analysed: 1TZG, 1HZH; and the following CH1-Clambda X-ray structure was analysed: 2RCS.

Alignment of the constant domains of GM (SEQ ID NO:8) and KM (SEQ ID NO:9) allotypes are shown in FIG. 5. Alignment of the constant domains of Kappa (SEQ ID NO:10) and Lambda (SEQ ID NO:11) are shown in FIG. 6.

Using standard methods in available molecular modelling packages, e.g., MOE (Molecular Operating Environment) software available from Chemical Computing Group (www.chemcomp.com), intramolecular ionic interactions were identified. This analysis specifically led to the to the identification of 6 CH3-CH3 GM ionic interactions, 6 CH3-CH3 KM ionic interactions, 2 CH1-CKappa and 2 CH1-CLambda interactions all listed below.
CH3-CH3 KM: D239-K322, E240-K253, D282-K292
CH3-CH3 GM: E239-K322, E240-K253, D282-K292
CKappa-CH1: E15-K96, D14-K101
CLambda-CH1: E16-K96, E17-K30

Example 3

Modification of Amino Acids in First and Second Light-chain Heavy Chain Pairs to Promote Heterodimer Formation Amino acid residues involved in the above-described interactions were subjected to substitutions in two light-chain heavy chain pairs from different antibodies having different specificities in order to increase the energy of (required for) homodimeric interactions and thereby favor heterodimeric interactions. The same principle can be applied for heavy-light chain interactions, and for soluble heterodimeric receptors.

| CH3-Unmodified | <-> | CH3-Unmodified |
|---|---|---|
| D239 | <-> | K322 |
| E240 | <-> | K253 |
| K292 | <-> | D282 |
| K322 | <-> | D239 |
| K253 | <-> | E240 |
| D282 | <-> | K292. |

Suggesting the modifications K322D, K253E, D282K in chain A and D239K, E240K, K292D in chain B leads to a CH3-Modified-A<->CH3-Modified-B interaction with only matching pairs as follows:

| D239 | <-> | K322 |
|---|---|---|
| E240 | <-> | K253 |
| K292 | <-> | D282 |
| D322 | <-> | K239 |
| E253 | <-> | K240 |
| K282 | <-> | D292. |

The CH3-Modified-A<->CH3-Modified-A interaction becomes:

| D239 | <-> | D322 |
|---|---|---|
| E240 | <-> | E253 |
| K292 | <-> | K282 |
| D322 | <-> | D239 |
| E253 | <-> | E240 |
| K282 | <-> | K292, | with only charge repulsion pairs.

A similar approach can be applied for the GM, and Heavy light-chain interactions.

Based on the high homology of immunoglobulins, a structural homology can be predicted, and the interactions described above have counterparts for other human isotypes (IgG24) and mouse and rat IgGs. To identify the corresponding residues, an alignment has been performed and is shown in FIG. 7.

With respect to conservation of heavy chain, the following can be concluded:
D239 or E239 is conserved in all subtypes and species
K322 is conserved in all subtypes and species
E240 is conserved in humans, rat IgG1, IgG2a, mouse IgG2a
K253 is conserved in humans, rat IgG1, IgG2a
D282 is conserved in all subtypes and species except for mouse IgG1
K322 is conserved in all subtypes and species
K96 is conserved in all subtypes and species except for human IgG3
K101 or R101 is conserved in all subtypes and species except for mouse IgG2b
K30 is conserved in all subtypes and species except for human IgG3

With respect to conservation of light chain, the following can be concluded:

E15 is conserved in human and mice (rat not investigated)
D14 is not conserved
E16 is conserved in human and mice (rat not investigated)
E17 is conserved in human and mice (rat not investigated).

Example 3

Cloning of Soluble Human CD94 (hCD94) and Human NKG2A (hNKG2A)

Human CD94 (hCD94) and human NKG2A (hNKG2A) were cloned from a human NK cDNA library purchased from Spring Bioscience (#PHD-138). Primers were designed using sequences from the NCBI database with accession numbers U30610 (hCD94) and AF461812 (hNKG2A). Primers used for hCD94 were

```
                               (forward; SEQ ID NO: 40)
5' GGATCCTCTTTTACTAAACTGAGTATTGAGCCAGC,
and (reverse, SEQ ID NO: 41)
5' GCGGCCGCAGATCTATTAAATGAGCTGTTGCTTACAGATATAACG.
```

Primers used for hNKG2A were

```
                               (forward, SEQ ID NO: 42)
5'GGATCCCAGAGGCACAACAATTCTTCCCTG (reverse, SEQ ID NO: 43)
5'GCGGCCGCAGATCTATTAAAGCTTATGCTTACAATG.
```

The forward primers contained a BamHI restriction site and the reverse primers contained NotI and BglII restriction sites. The products were amplified using a touch-down PCR-procedure.

Soluble hCD94 resulted in a 438 bp fragment that was cloned into pCR4blunt-Topo and sequence verified. Soluble hNKG2A (405 bp) was cloned into pCR2.1-TOPO and correct clones were identified by sequencing.

Example 4 mFc-hNKG2A or mFc-hCD94 Expression Constructs for Mammalian Cells

Murine Fc (mFc) was cloned from an IMAGE clone #2651217. Primers used were

```
                               (forward, SEQ ID NO: 44)
5'GCTAGCATGCCGCTGCTGCTACTGCTGCCCCTGCTGTGGGCAGGGGCC

CTGGCTATGGATGTGCCCAGGGATTGTGGTTG (reverse, SEQ ID NO: 45)
5'GGATCCTTTACCAGGAGAGTGGGAGAGGC
```

Figure 9:
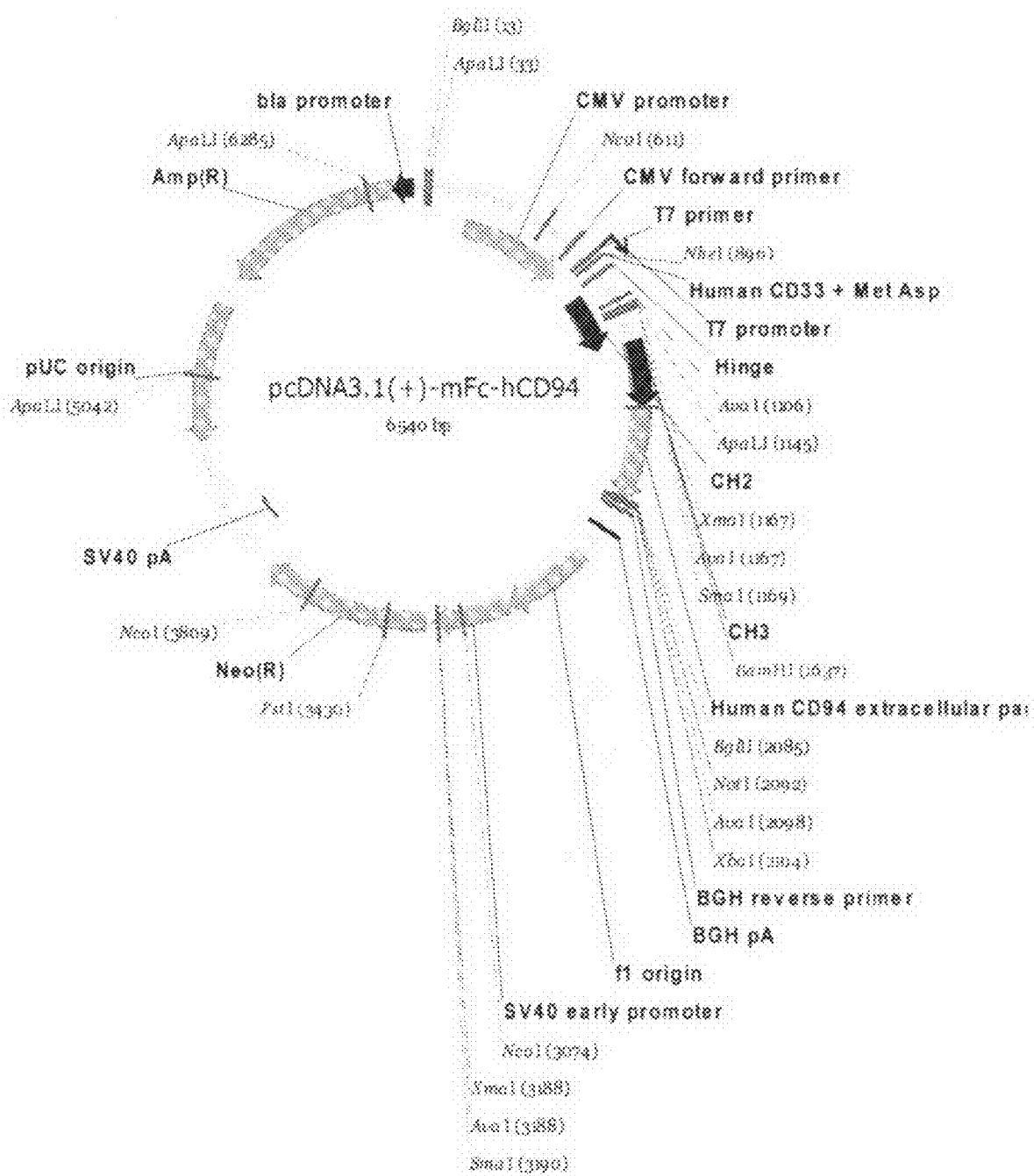
FIG. 9: pcDNA3.1(+)-mFc-hCD94 plasmid construct (Example 4).
Figure 10:
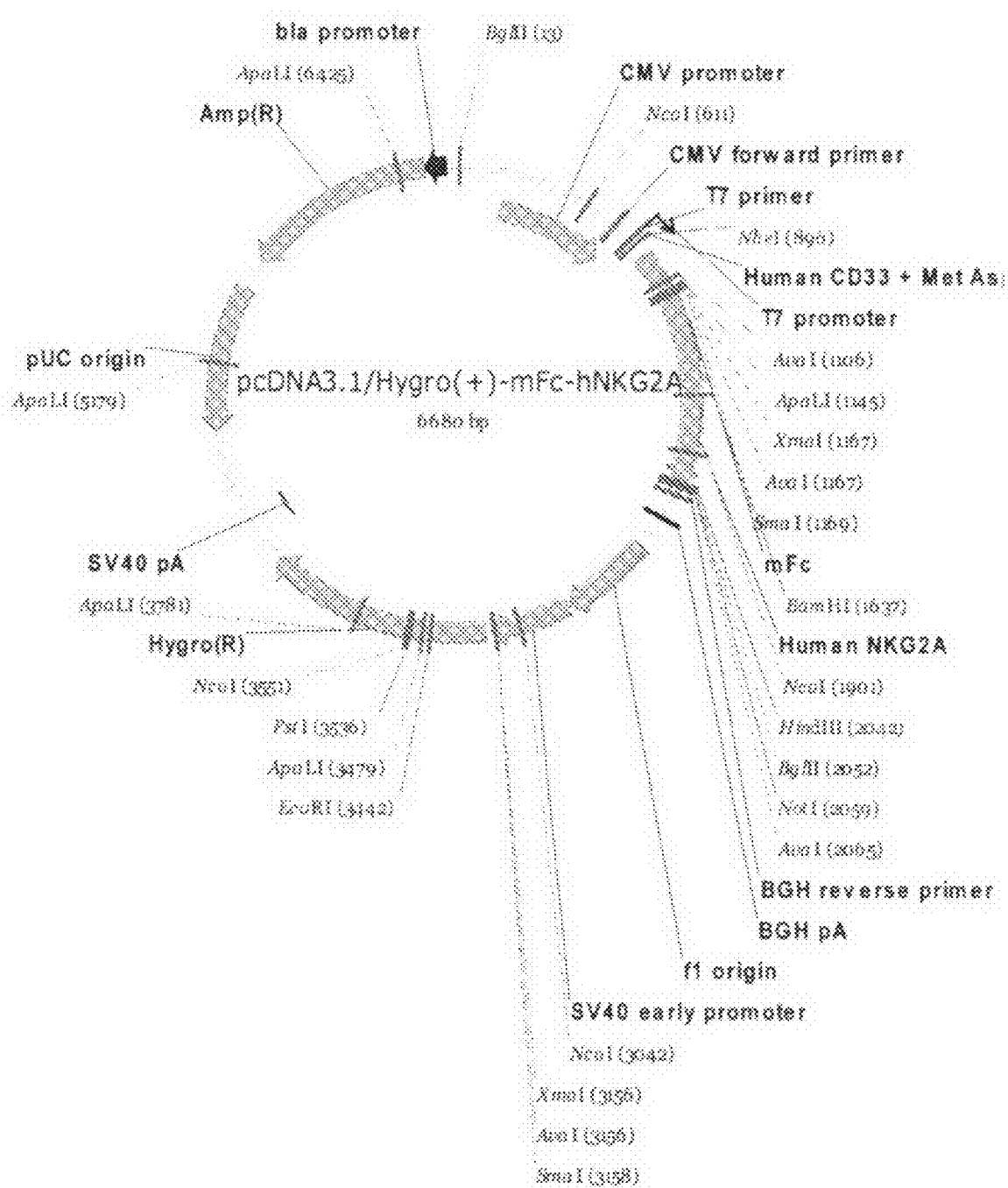
FIG. 10: pcDNA3.1/Hygro(+)-mFc-hNKG2A plasmid construct (Example 4).

The forward primer contains a NheI restriction site followed by CD33 signal peptide and a met and a asp residue. The reverse primer contains a BamHI restriction site. PCR was carried out in 50 µl reaction using 300 ng template, 200 µM dNTP mix, Easy-A High-Fidelity PCR cloning enzyme and buffer from Stratagene #600400. A single denaturerring step at 94 C/2 min was followed by 15 cycles as given: 94° C./30 sec; 68° C./30 sec; 72° C./90 sec, ending with 72° C./10 min. The PCR product was separated on a 1% agarose containing EtBr, purified with GFX kit from Amersham Biosciences #27-9602-01 and cloned into pCR4-TOPO (Invitrogen) and sequenced.

mFc was inserted into pcDNA3.1 or pcDNA3.1/Hygro (Invitrogen) using the restriction sites NheI and BamHI. hCD94 was inserted into pcDNA3.1 with mFc using BamHI and NotI (pBF5) and hNKG2A was inserted into pcDNA3.1/Hygro the same way (pBF6). See FIGS. 9 and 10.

pBF6 Encodes the Following (SEQ ID NO:31):

```
1
MPLLLLLPLLWAGALAMDVPRDCGCKPCICTVPEVSSVFIFPPKPKDVLT

51
ITLTPKVTCVVVDISKDDPEVQFSWFVDDVEVHTAQTKPREEQFNSTFRS

101
VSELPIMHQDWLNGKEFKCRVNSAAFPAPIEKTISKTKGRPKAPQVYTIP

151
PPKEQMAKDKVSLTCMITDFFPEDITVEWQWNGQPAENYKNTQPIMDTDG

201
SYFVYSKLNVQKSNWEAGNTFTCSVLHEGLHNHHTEKSLSHSPGKGSQRH

251
NNSSLNTRTQKARHCGHCPEEWITYSNSCYYIGKERRTWEESLLACTSKN

301
SSLLSIDNEEEMKFLSIISPSSWIGVFRNSSHHPWVTMNGLAFKHEIKDS

351
DNAELNCAVLQVNRLKSAQCGSSIIYHCKHKL
``` pBF5 Encodes the Following (SEQ ID NO:32):

```
1
MPLLLLLPLLWAGALAMDVPRDCGCKPCICTVPEVSSVFIFPPKPKDVLT

51
ITLTPKVTCVVVDISKDDPEVQFSWFVDDVEVHTAQTKPREEQFNSTFRS

101
VSELPIMHQDWLNGKEFKCRVNSAAFPAPIEKTISKTKGRPKAPQVYTIP

151
PPKEQMAKDKVSLTCMITDFFPEDITVEWQWNGQPAENYKNTQPIMDTDG

201
SYFVYSKLNVQKSNWEAGNTFTCSVLHEGLHNHHTEKSLSHSPGKGSSFT

251
KLSIEPAFTPGPNIELQKDSDCCSCQEKWVGYRCNCYFISSEQKTWNESR

301
HLCASQKSSLLQLQNTDELDFMSSSQQFYWIGLSYSEEHTAWLWENGSAL

351
SQYLFPSFETFNTKNCIAYNPNGNALDESCEDKNRYICKQQLI
```

Example 5

Mutated Fc-Portion Constructs for Mammalian Cell Expression

Mutations in the mFc part were achieved using QuikChange mutagenesis on the constructs in Example 3. The single mutation (made as T243Y, Y284T in SEQ ID NO: 21 [IGHG1_MOUSE; IgG1], corresponding to T249Y, Y290T in SEQ ID NO: 14 [GCM_MOUSE; IgG2A]) was carried out using QuikChange II Site-directed Mutagenesis Kit and manual from Stratagene #200523 and the following 2 primer sets:

```
                                         (SEQ ID NO: 46)
5'GGCCAAGGATAAAGTCAGTCTGTACTGCATGATAACAGACTTC (SEQ ID NO: 47)
5'GAAGTCTGTTATCATGCAGTACAGACTGACTTTATCCTTGGCC
and (SEQ ID NO: 48)
5'CAGATGGCTCTTACTTCGTCACCAGCAAGCTCAATGTGCAGAAG (SEQ ID NO: 49)
5'CTTCTGCACATTGAGCTTGCTGGTGACGAAGTAAGAGCCATCTG.
```

A single denaturering step at 95° C./30 sec was followed by 15 cycles as given: 95° C./30 sec; 55° C./1 min; 68° C./7 min., ending with 72° C./10 min.

The double mutations (E239K and K292D in one Fc-peptide, D282K and K332E in the other Fc-peptide) were carried out using QuickChange multi Site-directed mutagenesis kit and manual (Stratagene) #200513 and the following primer sets:

```
E239K:
                                         (SEQ ID NO: 50)
CCATTCCACCTCCCAAGAAGCAGATGGCCAAGG

K292D:
                                         (SEQ ID NO: 51)
GCTCTTACTTCGTCTACAGCGACCTCAATGTGCAGAAGAGCAAC,
and D282K:
                                         (SEQ ID NO: 52)
GAACACTCAGCCCATCATGAAGACAGATGGCTCTTACTTCG K322E:
                                         (SEQ ID NO: 53)
CCACCATACTGAGGAGAGCCTCTCCCACTCTCCTGG.
```

A single denaturering step at 95° C./1 min was followed by 30 cycles as given: 95° C./1 min; 55° C./1 min; 65° C./13.5 min.

Example 6

Single-chain NKG2ACD94 for Expression in Mammalian Cells

Figure 11:
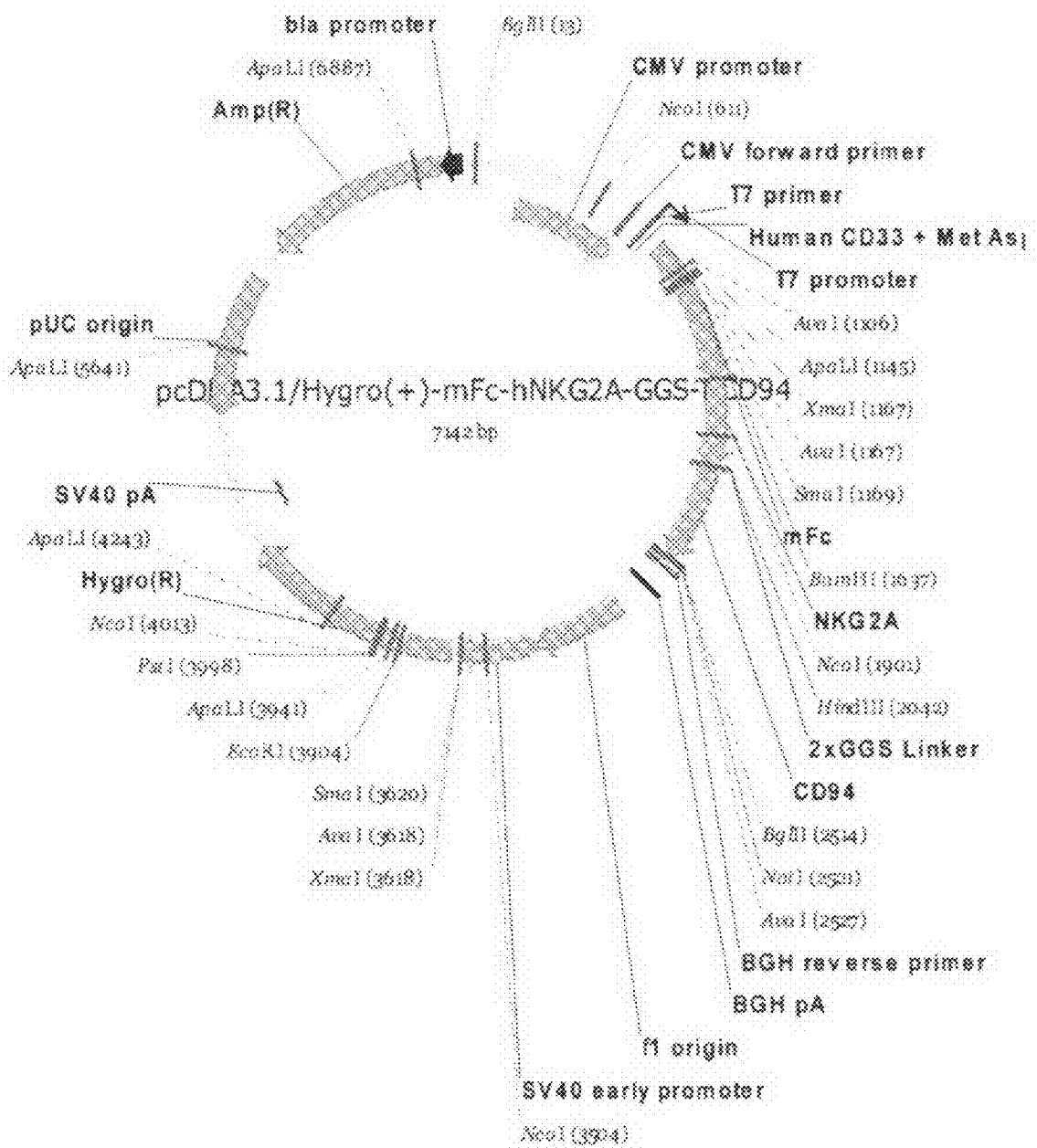
FIG. 11: pcDNA3.1/Hygro(+)-mFc-hNKG2A-GGS-GGS-hCD94 plasmid construct (Example 6).

NKG2A-2×GGS-CD94 was cloned into pcDNA3.1/hygro with mFc in the BamHI/NotI site (pBF17). See FIG. 11.

pBF17 Encodes the Following (SEQ ID NO:39):

```
1
MPLLLLLPLLWAGALAMDVPRDCGCKPCICTVPEVSSVFIFPPKPKDVLT

51
ITLTPKVTCVVVDISKDDPEVQFSWFVDDVEVHTAQTKPREEQFNSTFRS

101
VSELPIMHQDWLNGKEFKCRVNSAAFPAPIEKTISKTKGRPKAPQVYTIP

151
PPKEQMAKDKVSLTCMITDFFPEDITVEWQWNGQPAENYKNTQPIMDTDG

201
SYFVYSKLNVQKSNWEAGNTFTCSVLHEGLHNHHTEKSLSHSPGKGSQRH

251
NNSSLNTRTQKARHCGHCPEEWITYSNSCYYIGKERRTWEESLLACTSKN

301
SSLLSIDNEEEMKFLSIISPSSWIGVFRNSSHHPWVTMNGLAFKHEIKDS

351
DNAELNCAVLQVNRLKSAQCGSSIIYHCKHKLGGSGGSRSSFTKLSIEPA

401
FTPGPNIELQKDSDCCSCQEKWVGYRCNCYFISSEQKTWNESRHLCASQK

451
SSLLQLQNTDELDFMSSSQQFYWIGLSYSEEHTAWLWENGSALSQYLFPS

501
FETFNTKNCIAYNPNGNALDESCEDKNRYICKQQLI
```

Example 7

Expression in Mammalian Cells

All the constructs in Examples 2-5 were expressed transient in HEK293 cells using 293fectin #12347-019 from Invitrogen for transfection. 5×10$^5$ cells/ml were seeded in a 125 ml Erlen-Meyer flask. The following day, the cells were transfected as follows: 30 μg DNA was diluted in 1 ml Opti-Mem and 40 μl 293 fectin was diluted in 960 μl Opti-Mem. After 5 min. at room temperature (RT) the two mixtures were mixed and incubated 25 min. at RT before the addition to the cell culture. Media was harvested 4-6 days later by centrifugation at 1500×g for 15 min. The results were visualized by western blot analysis, where all the blots were probed with goat-anti-mouse-IgG.

Figure 12:
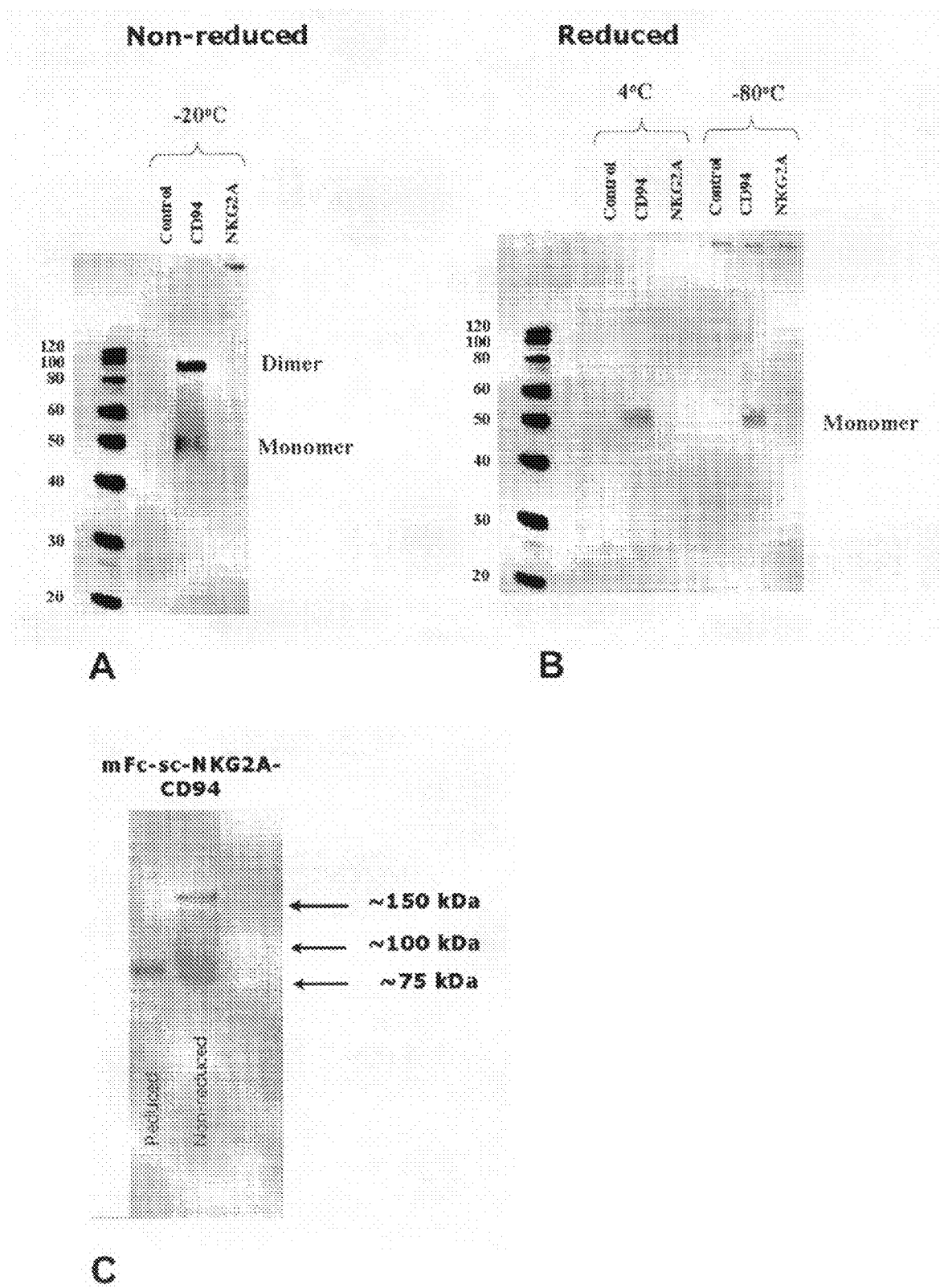
FIGS. 12A-C: Western blot analysis of (A) hCD94-mFc/hNKG2A-mFc under non-reducing conditions, (B) hCD94-mFc/hNKG2A-mFc under reducing conditions, and (C) mFc-single-chain-NKG2A-CD94 expressed in HEK293 under reducing and non-reducing conditions (Example 7).

Exemplary results of western blot analysis are shown in FIGS. 12A-12C. All blots were probed with goat-anti-mouse-IgG. mFc-CD94 and mFc-NKG2A were expressed individually in HEK293. mFc-NKG2A was not expressed in the absence of mFc-CD94. mFc-single-chain-NKG2A-CD94 was expressed in HEK293.

Example 8

Purification of CD94-mFc/NKG2A-mFc Heterodimers Produced in Mammalian Cell Lines Six different variants of CD94-mFc and NKG2A-mFc fusion proteins were purified from cell culture supernatants by Protein A affinity chromatography. The fusion proteins were CD94-mFc homodimer, CD94-2×GGS-NKG2A-mFc, NKG2A-mFc, CD94-mFc(T249Y) NKG2A-mFc(Y290T), CD94-mFc NKG2A-mFc, CD94-mFc(E239K, K292D) NKG2A-mFc(D282K, K332E). CD94/NKG2A-mouse Fc fusion proteins were produced using serum-free medium. CD94/NKG2A-mouse Fc fusion protein was expressed from CHO-DUKX B11 cells.

Purification of CD94/NKG2A-mouse Fc fusion proteins was performed as follows. Cell culture supernatants were sterile filtered and applied to a 10 ml Protein A sepharose column (Sigma, St. Louis, Mo.) packed in a XK16 column (GE-Healthcare, Hillerd, Denmark) using an ÄKTA explorer FPLC system (GE-Healthcare, Hillerd, Denmark). The protein A column was equilibrated in 20 mM Tris pH 7.5 at 6 ml/min. After sample application, the column was washed until UV absorbance at 280 nm was low. The bound proteins were eluted using a step gradient from 0 to 100% 50 mM Glycine pH 2.7 and 2 ml fractions were collected. Fractions containing the proteins of interest were pooled and titrated to neutral pH. In some cases the pooled proteins were concentrated using a Vivaspin 20, 30.000 MWCO (Sartorius, Roskilde, Denmark) and buffer exchanged into PBS buffer. Protein concentrations were determined by OD280 with an extension coefficient of $(1.5 \text{ g/l})^{-1} \times \text{cm}^{-1}$.

The purified proteins were analyzed by 1-D SDS-PAGE on 4-12% NuPage gels (In-Vitrogen, Carlsbad, Calif.) running in MOPS buffer. 1-D gels were stained using Gelcode coomassie stain (Pierce, Rockford, Ill.) or blotted onto PVDF membranes (InVitrogen, Carlsbad, Calif.).

The antibodies Z199 (anti-NKG2A, Beckman Coulter, Fullerton, Calif.) and HP-3D9 (anti-CD59, Santa Cruz Biotechnology Inc., Santa Cruz, Calif.) were prepared for western-blotting by labeling with Cy3 and Cy5 using Cy-dye protein labeling kits (GE-Healthcare, Hillerd, Denmark). After blotting, the membranes were blocked in 5% blotto (Pierce, Rockford, Ill.) and incubated with both antibodies diluted 1:200 in washing buffer. After washing the blots were scanned on either an Ettan Dige Imager or a Typhoon Trio+ scanner (GE-Healthcare, Hillerd, Denmark) using the settings for the two different fluorophors.

Results Proteins purified from 330-350 ml serum-free culture supernatant from HEK293 cells resulted in 0.08 to 1.17 mg protein. See Table 3. The largest protein amounts were purified from cells expressing the two plasmids with a single mutation in murine immunoglobulin constant region. Analysis of the purified proteins by 1-D SDS PAGE showed that the purification yielded quite pure proteins with no obvious contaminants present. The main band corresponded to dimer formation of the proteins, whereas a higher molecular weight species corresponded to tetramer formation.

TABLE 3

Proteins purified from serum free expression in HEK293 freestyle cells

| Protein | Plasmid Constructs | Amount (mg) |
| --- | --- | --- |
| CD94-mFc homodimer | pBF5 | 0.37 |
| CD94-2xGGS-NKG2A-mFc | pBF17 | 0.18 |
| NKG2A-mFc | pBF6 | 0.27 |
| CD94-mFc T249Y NKG2A-mFc Y290T | pBF19 and pBF20 | 1.7 |
| CD94-mFc NKG2A-mFc | pBF5 and pBF6 | 0.88 |
| CD94-mFc E239K, K292D NKG2A-mFc D282K, K332E | pBF21 and pBF22 | 0.08 |

To ascertain that the purified proteins were combinations of both CD94 and NKG2A, a western blot were made, where the two antibodies Z199 and HP-3D9 (against NKG2A and CD94 respectively) were used. The antibodies were labeled with fluorescence dyes, making it possible to use both antibodies on a single blot (FIGS. 13A and B). From the two different detections of the blot it was evident that the cell lines expressing CD94-mFc alone only produced this protein. No protein could be observed where the NKG2A homodimer should be, showing that this protein does not produce homodimers. In all the other lanes, bands could be observed corresponding to the presence of both CD94 and NKG2A, showing that true heterodimers have been produced.

A stable CHO cell line (CHO-DUKX B11) expressing the single-chain CD94-2xGGS-NKG2A-mFc constructs was used to produce protein for Biacore analysis. 215 ml cell culture supernatant was purified on Protein A column and buffer exchanged into PBS. The resulting protein was analyzed by 1-D SDS PAGE and western blotting using the two antibodies Z199 and HP-3D9 labeled with fluorescence dyes (FIGS. 14A and B). Both the 1-D gel as well as the western blot showed that the single-chain protein appeared as a dimer and gave responses to both anti-CD94 and anti-NKG2A antibodies.

Example 9

NKG2A Plasmid Construct for Expression in *E. Coli*

Figure 15:
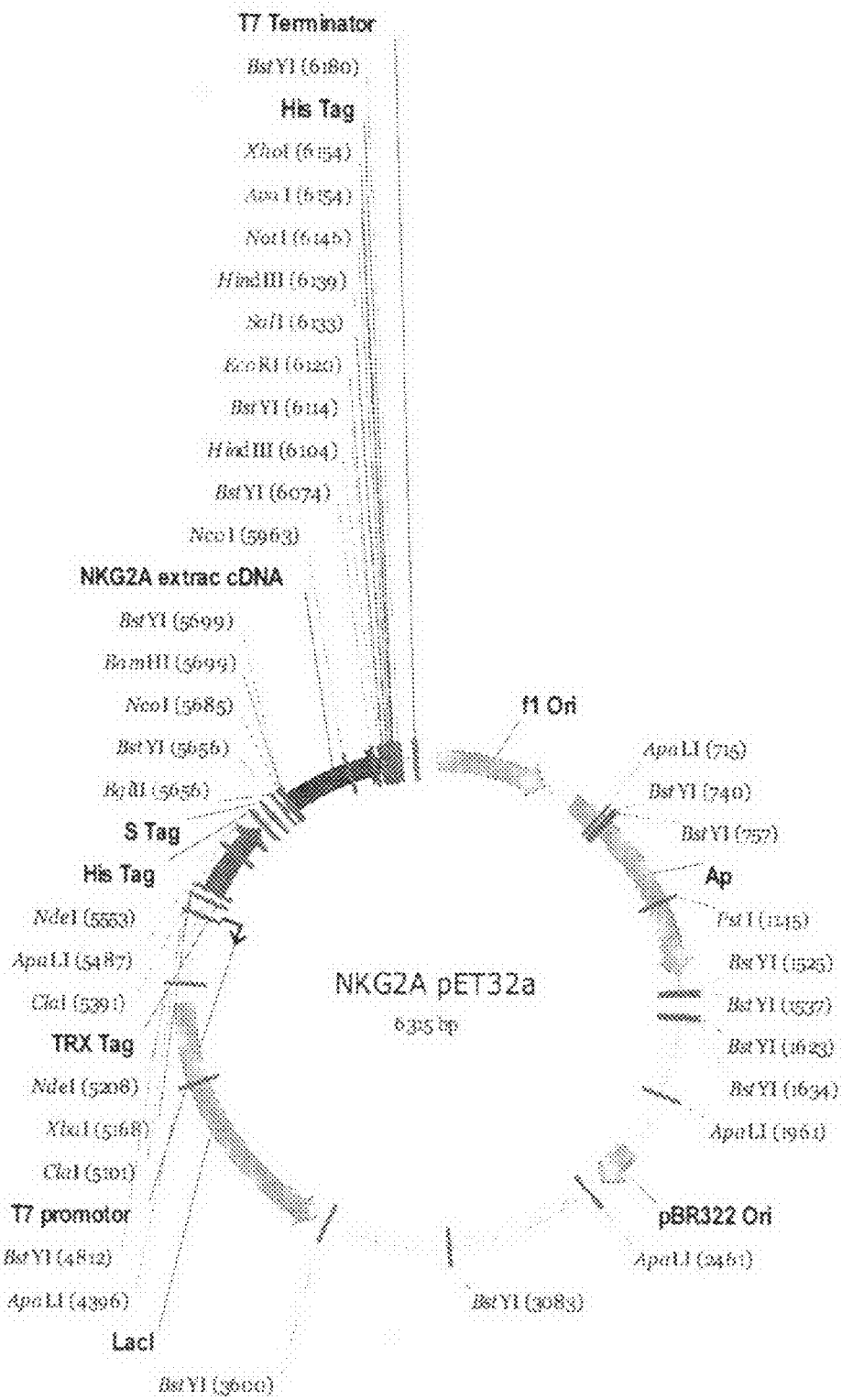
FIG. 15: Trx-hexaHis pET32a hNKG2A plasmid construct (pISNN415) (Example 9).

NKG2A was subcloned BamHI-BgIII in BamHI+dephosphorylated (using calf intestine phophatase) in Trx-hexaHis pET32a to produce pISNN415, encoding the following sequence (SEQ ID NO:54) (FIG. 15):

```
MSDKIIHLTDDSFDTDVLKADGAILVDFWAEWCGPCKMIAPILDEIADEYQGKLTVAKLN    60

IDQNPGTAPKYGIRGIPTLLLFKNGEVAATKVGALSKGQLKEFLDANLAGSGSGHMHHHH   120

HHSSGLVPRGSGMKETAAAKFERQHMDSPDLGTDDDDKAMADIGSQRHNNSSLNTRTQKA   180

RHCGHCPEEWITYSNSCYYIGKERRTWEESLLACTSKNSSLLSIDNEEEMKFLSIISPSS   240

WIGVFRNSSHHPWVTMNGLAFKHEIKDSDNAELNCAVLQVNRLKSAQCGSSIIYHCKHKL   300

**                                                           302
```

Example 10

Expression of NKG2A Extracellular Domain in *E. Coli*

Figure 16:
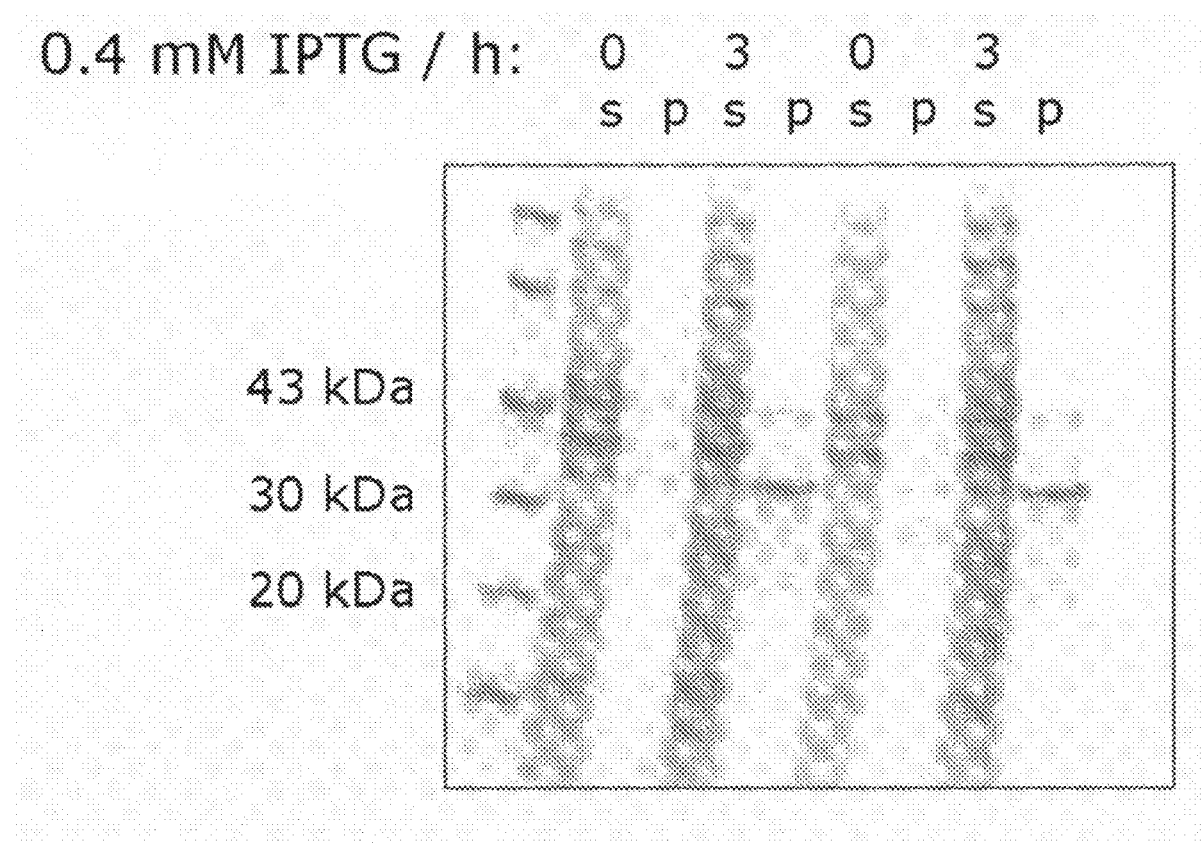
FIG. 16: Analysis of Trx-hexaHis-NKG2A expression in E. coli (Example 10; p=pellet fraction; s=soluble fraction).).

The human NKG2A (residues 99-233 of SEQ ID NO:1) extracellular domain was expressed in *E. coli*. NKG2A was fused N-terminally to Thioredoxin (Trx) and hexaHis tag. The expected molecular weight was 33 kDa. Trx and hexaHis can be proteolytically removed using Enterokinase. Trx-NKG2A was expressed at approximately 10 mg/L in 500 mL lab-scale cultures (FIG. 16).

Example 11

CD94 Plasmid Construct for Expression in *E. Coli*

Figure 17:
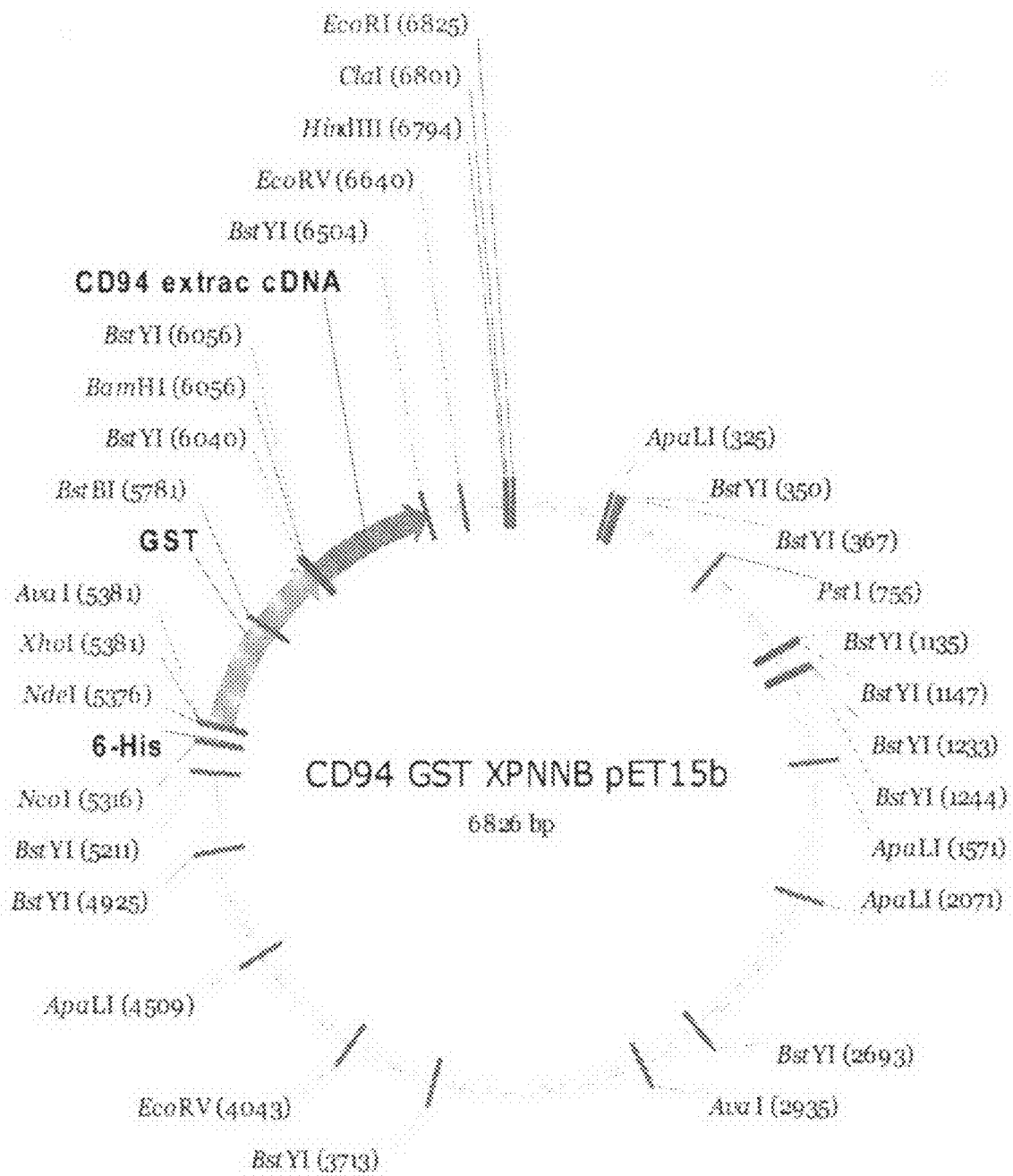
FIG. 17: HexaHis-GST XPNNB pET15b hCD94 plasmid construct (pISNN427) (Example 11).

CD94 was subcloned BamHI-BgIII in BamHI+dephosphorylated (using calf intestine phophatase) hexaHis-GST XPNNB pET15b to produce pISNN427, encoding the following sequence (SEQ ID NO:55) (FIG. 17):

```
MGSSHHHHHHSSGLVPRGSHMLESPILGYWKIKGLVQPTRLLLEYLEEKYEEHLYERDEG    60

DKWRNKKFELGLEFPNLPYYIDGDVKLTQSMAIIRYIADKHNMLGGCPKERAEISMLEGA   120

VLDIRYGVSRIAYSKDFETLKVDFLSKLPEMLKMFEDRLCHKTYLNGDHVTHPDFMLYDA   180

LDVVLYMDPMCLDAFPKLVCFKKRIEAIPQIDKYLKSSKYIAWPLQGWQATFGGGDHPPK   240

SDLVPRGSSFTKLSIEPAFTPGPNIELQKDSDCCSCQEKWVGYRCNCYFISSEQKTWNES   300

RHLCASQKSSLLQLQNTDELDFMSSSQQFYWIGLSYSEEHTAWLWENGSALSQYLFPSFE   360

TFNTKNCIAYNPNGNALDESCEDKNRYICKQQLI**                          396
```

Example 12

Expression of CD94 Extracellular Domain in E. Coli

Figure 18:
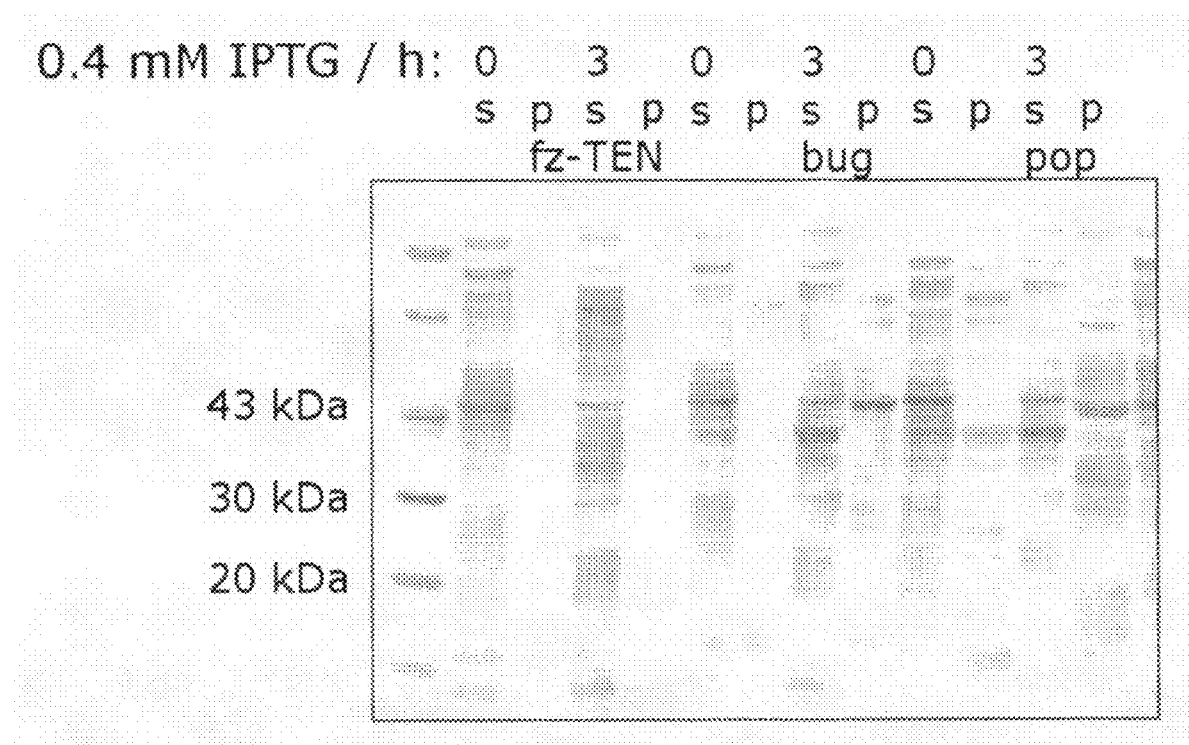
FIG. 18: Analysis of hexaHis-GST-CD94 expression in E. coli (Example 12; p=pellet fraction; s=soluble fraction).).

The human CD94 (residues 34-179 of SEQ ID NO:2) extracellular domain was expressed in *E. coli*. CD94 was fused N-terminally to hexaHis and Glutathione-S-transferase (GST). The expected molecular weight was 46 kDa. hexaHis-GST can be removed by cleavage with Thrombin. The expression level of GST-CD94 was approximately 50 mg/L in 500 mL lab-scale cultures. Expression was obtained at 30° C. The fusion proteins were expressed in an insoluble form. Various lysis methods were screened in this particular experiment (freeze-thaw (fz) cycles using TEN (tris, EDTA, NaCl), or detergent based lysis using BugBuster (Novagen) or PopCulture (Novagen)) (FIG. 18).

Example 13

Cloning of Single-chain NKG2A-CD94 or CD94-NKG2A Expression Constructs; Two Strategies Primers used were:

```
2 × GGS - up:
                                              (SEQ ID NO: 56)
AGCTTGGCGGTAGCGGCGGTAGCA

2 × GGS dwn:
                                              (SEQ ID NO: 57)
GATCTGCTACCGCCGCTACCGCCA 2 × GGS insertion dwn:
                                              (SEQ ID NO: 58)
GTTGTGCCTCTGGCTACCGCCGCTACCGCCAATGAG-CTGTTGC
```

NKG2A-2×GGS-CD94. First, the NKG2A 3' end was altered in pBluescript-SK(−). The annealed oligos ('2×GGS-up' and '2×GGS dwn') which at the same time added a hydrophilic linker and removed stopcodons of the original clone was cloned HindIII-BgIII in NKG2A-pBluescript-SK(−) (pISNN425) (FIG. 19A). Second, CD94 was inserted BamHI-NotI in NKG2A-2×GGS linker pBluescript-SK(−) restricted BgIII-NotI (FIG. 19B). Correct clones were identified by restriction digestion and sequencing using T7 og T3 primers.

Figure 20:
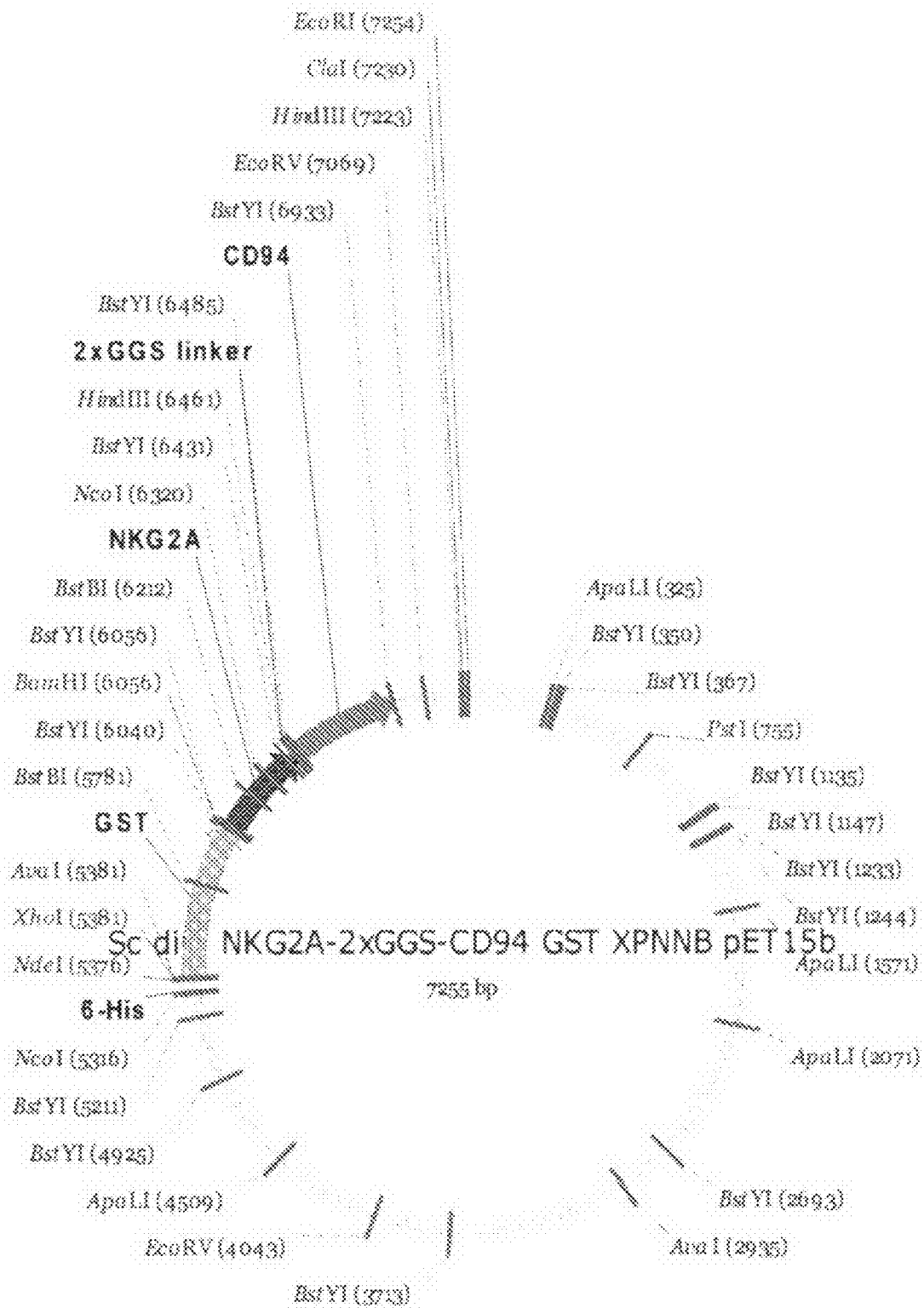
FIG. 20: Single-chain dimer NKG2A-2×GGS-CD94 GST XPNNB pET15b plasmid construct (Example 13).

NKG2A-2×GGS-CD94 (NKG2A-2×GGS-CD94-pBluescript-SK(−))) was subcloned BamHI-BgIII in BamHI restricted and +de-phosphorylated (using calf intestine phosphatase)-hexaHis-GST XPNNB pET15b or BamHI-BgIII in BamHI+dephosphorylated Trx-hexaHis pET32a (FIG. 20).

Figure 21:
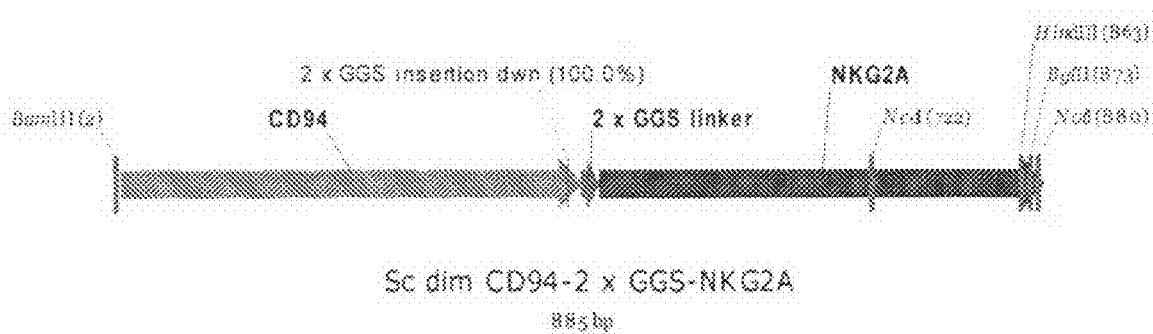
FIG. 21: Single-chain dimer NKG2A-2×GGS-CD94 construct.
Figure 22:
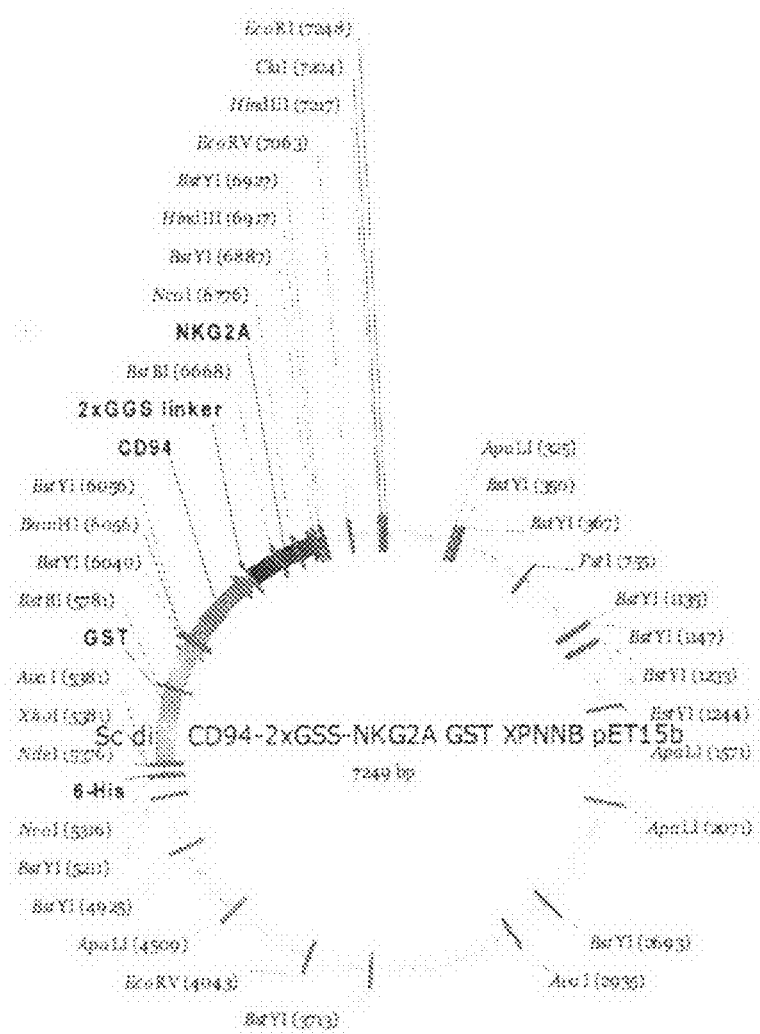
FIG. 22: CD94-2×GGS-NKG2A GST XPNNB pET15b plasmid construct (Example 13).

CD94-2×GGS-NKG2A. In another approach, CD94 is inserted BamHI-BgIII in BamHI restricted and dephosphorylated NKG2A pBluescript-SK(−) (pISNN425). A linker (2×GGS insertion dwn) which at the same time removes a stop codon and adds a hydrophilic linker is inserted by site-directed mutagenesis. The primer is 5-Phosphorylated and the 'Quick-change multi site-directed mutagenesis kit' (purchased form Stratagene) is used. T7 and T3 primers are used for sequence verification. CD94-2×GGS-NKG2A heterodimers are subcloned BamHI-BgIII in BamHI+dephosphorylated hexaHisGST XPNNB pET15b og BamHI-BgIII in BamHI+dephosphorylated Trx-hexaHis pET32a. See FIGS. 21 and 22.

The constructs are expressed in BL21 (DE3).

The amino-acid sequence for hexaHis-GST NKG2A-2× GGS-CD94 is (SEQ ID NO:37):

```
MGSSHHHHHHSSGLVPRGSHMLESPILGYWKIKGLVQPTRLLLEYLEEKYEEHLYERDEG    60

DKWRNKKFELGLEFPNLPYYIDGDVKLTQSMAIIRYIADKHNMLGGCPKERAEISMLEGA   120

VLDIRYGVSRIAYSKDFETLKVDFLSKLPEMLKMFEDRLCHKTYLNGDHVTHPDFMLYDA   180

LDVVLYMDPMCLDAFPKLVCFKKRIEAIPQIDKYLKSSKYIAWPLQGWQATFGGGDHPPK   240

SDLVPRGSQRHNNSSLNTRTQKARHCGHCPEEWITYSNSCYYIGKERRTWEESLLACTSK   300

NSSLLSIDNEEEMKFLSIISPSSWIGVFRNSSHHPWVTMNGLAFKHEIKDSDNAELNCAV   360

LQVNRLKSAQCGSSIIYHCKHKLGGSGGSRSSFTKLSIEPAFTPGPNIELQKDSDCCSCQ   420

EKWVGYRCNCYFISSEQKTWNESRHLCASQKSSLLQLQNTDELDFMSSSQQFYWIGLSYS   480

EEHTAWLWENGSALSQYLFPSFETFNTKNCIAYNPNGNALDESCEDKNRYICKQQLI**   539
```

The amino-acid sequence for Trx-hexaHis-NKG2A-2×GGS-CD94 is (SEQ ID NO:38):

```
MSDKIIHLTDDSFDTDVLKADGAILVDFWAEWCGPCKMIAPILDEIADEYQGKLTVAKLN    60
IDQNPGTAPKYGIRGIPTLLLFKNGEVAATKVGALSKGQLKEFLDANLAGSGSGHMHHHH   120
HHSSGLVPRGSGMKETAAAKFERQHMDSPDLGTDDDDKAMADIGSQRHNNSSLNTRTQKA   180
RHCGHCPEEWITYSNSCYYIGKERRTWEESLLACTSKNSSLLSIDNEEEMKFLSIISPSS   240
WIGVFRNSSHHPWVTMNGLAFKHEIKDSDNAELNCAVLQVNRLKSAQCGSSIIYHCKHKL   300
GGSGGSRSSFTKLSIEPAFTPGPNIELQKDSDCCSCQEKWVGYRCNCYFISSEQKTWNES   360
RHLCASQKSSLLQLQNTDELDFMSSSQQFYWIGLSYSEEHTAWLWENGSALSQYLFPSFE   420
TFNTKNCIAYNPNGNALDESCEDKNRYICKQQLI**                           456
```

Example 14

Expression of NKG2A-2×GGS-CD94 in *E. Coli*

Figure 23:
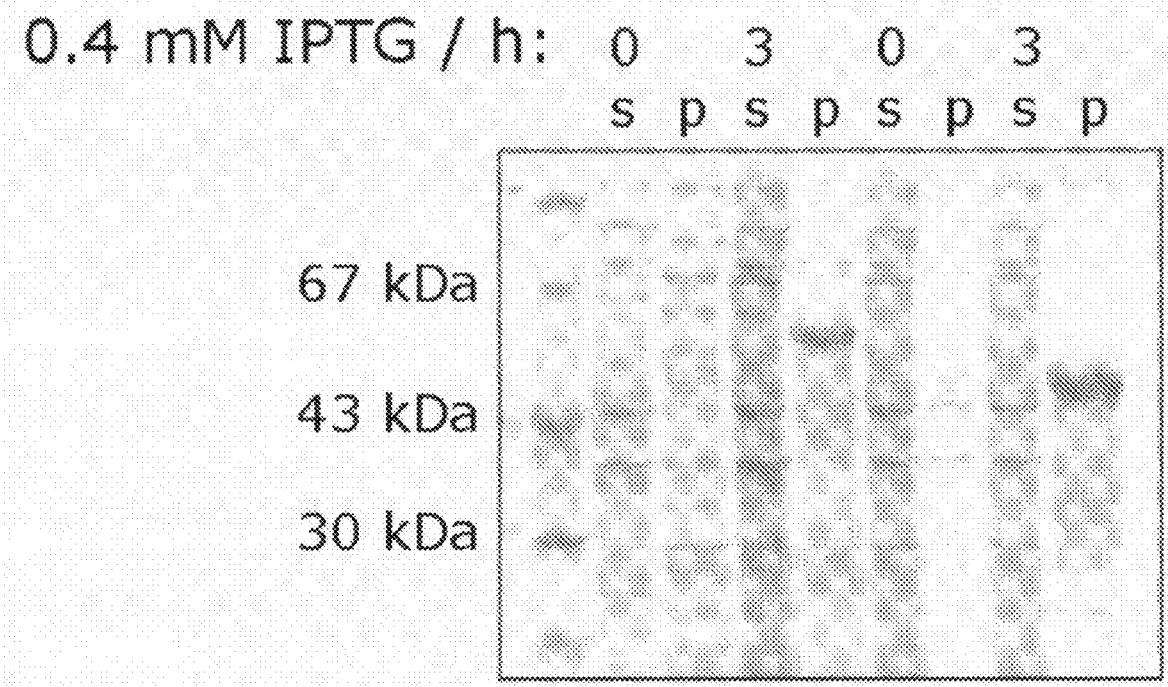
FIG. 23: 6His-GST-NKG2A-2×GGS-CD94 & Trx-6His-NKG2A-2×GGS-CD94 expression in E. coli (Example 14; p=pellet fraction; s=soluble fraction).

Human NKG2A (residues 99-233 of SEQ ID NO:1) and human CD94 (residues 34-179 of SEQ ID NO:2) extracellular parts, separated by a gly-gly-ser-gly-gly-ser linker, were expressed as a single-chain fusion in the *E. coli* strain BL21 (DE3). Two different NKG2A-CD94 fusion constructs were expressed carrying respectively Thioredoxin (Trx) and hexaHis tag or hexaHis and Glutathione-S-transferase (GST) at their N-termini. Trx-hexaHis-NKG2A-2×GGS-CD94 was expressed at approximately 100 mg/L in 500 mL lab-scale cultures. The expression level of hexaHis-GST-NKG2A-2×GGS-CD94 was approximately 70 mg/L in 500 mL lab-scale cultures. Trx-hexaHis may be proteolytically removed using Enterokinase. hexaHis-GST can be removed by cleavage with Thrombin. Expression was obtained at 37° C. The fusion proteins were highly expressed in the insoluble pellet fractions (p) (FIG. 23).

Example 15

Expression of TRX-His-tag-NKG2A-GGSGGS-CD94 Single Chain Constructs in *E. Coli*

Isolated cells from 250 ml fermentation were washed once with 50 mM Tris pH 8, 200 mM NaCl, 5 mM EDTA. The obtained pellet was resuspended in 50 mM Tris pH 8, 200 mM NaCl, 5 mM EDTA, 10 w/v % sucrose, 5 mM DTT, 5 mM benzamidine, and lysed in a French press. The insoluble inclusion bodies were collected by centrifugation, washed and dissolved in 6M guadiniumhydrochlorid, 100 mM Tris pH 8, 40 mM DTT.

The solubilized protein was diluted into 20 ml refolding buffer 50 mM Tris pH 8.2, 750 mM arginine, 10 mM NaCl, 0.5 mM KCl, 0.5 g/L PEG3350, 2 mM MgCl2, 2 mM CaCl2, 4 mM cystine, 1.5 mM DTT. The refolding mixture was left at 5° C. over night.

The refolded protein was diluted 5 times with 10 mM Tris pH 8 and purified by application to a 5 ml Q sepharose fast flow column. After wash with 2 Cv 10 mM Tris pH 8, 50 mM NaCl, the protein was eluted by a linear gradient over 10 CV to 10 mM Tris pH 8, 2 M NaCl.

Example 16

TRX-His-tag-NKG2A-GGSGGS-CD94

The isolated cells from 1 L fermentation were washed once with 50 mM Tris pH 8, 200 mM NaCl, 5 mM EDTA. The obtained pellet was resuspended in 50 mM Tris pH 8, 200 mM NaCl, 5 mM EDTA, 10 w/v % sucrose, 5 mM DTT, 5 mM benzamidine, and lysed in a French press. The insoluble inclusion bodies were collected by centrifugation, washed and dissolved in 6M guadiniumhydrochlorid, 100 mM Tris pH 8, 40 mM DTT.

The solubilized protein was diluted into 100 ml refolding buffer 50 mM Tris pH 8.2, 750 mM aginine, 10 mM NaCl, 0.5 mM KCl, 0.5 g/L PEG3350, 2 mM MgCl2, 2mM CaCl2, 4 mM cystine, 1.5 mM DTT. The refolding mixture was left at 5° C. over night.

The refolded protein was diluted 5 times with 10 mM Tris pH 8 and purified by application to a 5 ml Q sepharose fast flow column. After wash with 2 Cv 10 mM Tris ph 8, 50 mM NaCl, the protein was eluted by a linear gradient over 10 CV to 10 mM Tris pH 8, 2 M NaCl.

Example 17

His-Tag-GST-NKG2a-GGSGGS-CD94

Isolated cells from 1 L fermentation are washed once with 50 mM Tris pH 8, 200 mM NaCl, 5 mM EDTA. The obtained pellet is resuspended in 50 mM Tris pH 8, 200 mM NaCl, 5 mM EDTA, 10 w/v % sucrose, 5 mM DTT, 5 mM benzamidine, and lysed in a French press. The insoluble inclusion bodies are collected by centrifugation, washed and dissolved in 6M guadiniumhydrochlorid, 100 mM Tris pH 8, 40 mM DTT.

The solubilized protein is diluted into 20 ml refolding buffer 50 mM Tris pH 8.2, 750 mM aginine, 10 mM NaCl, 0.5 mM KCl, 0.5 g/L PEG3350, 2 mM MgCl2, 2 mM CaCl2, 4 mM cystine, 1.5 mM DTT. The refolding mixture is left at 5° C. over night.

The refolded protein is diluted 5 times with 10 mM Tris pH 8 and is purified by application to a 5 ml Q sepharose fast flow column. After wash with 2 Cv 10 mM Tris ph 8, 50 mM NaCl, the protein is eluted by a linear gradient over 10 CV to 10 mM Tris pH 8, 2 M NaCl.

Example 18

Characterization of Recombinant CD94/NKG2A Constructs by Surface Plasmon Resonance Analysis The following constructs were analyzed for binding to the immobilized antibodies HP-3D9, Z199 and rabbit anti-mouse (RaM), with subsequent binding of HLA-E tetramer:
CD94-mFc homo dimer
CD94-NKG2A-mFc singlechain
NKG2A-mFc homo dimer CD94-mFc/NKG2A heterodimer with single mutation
CD94-mFc/NKG2A heterodimer
CD94-mFc/NKG2A heterodimer with double mutation.
Materials Surface plasmon resonance studies were performed on a Biacore3000 instrument (Biacore AB, Uppsala, Sweden). Immobilization of ligands were conducted on a CM5 sensor chip (Biacore AB), using a standard amine coupling kit as described by the manufacture (Biacore AB).

HBS-EP buffer (10 mM HEPES, 150 mM NaCl, 3 mM EDTA, 0.005% Polysorbat 20 (v/v)) was used as running buffer, and for all dilutions. Regeneration of the sensor chip was performed by a short pulse (15 ul, Flow 30 ul/min) of 10 mM glycin-HCl pH 1.8.

All experiments were performed at flow rate 10 ul/min. at 25° C. Data was analyzed using Biaevaluation 4.1 software.

Anti-CD94 monoclonal antibody HP-3D9 (BD Pharmingen, cat #555887), anti-CD94/NKG2A monoclonal antibody Z199 (Immunotech, France) and Rabbit anti-mouse (RaM) polyclonal antibody (Biacore AB), were immobilized by amine coupling to a level of ~5000 RU in individual flow cells on a CM5 sensor chip.
Binding of CD94INKG2A Constructs to Anti-CD94 and Anti-CD94/NKG2A Monoclonal Antibodies, and Competition on HLA-E Tetramer Binding All constructs were diluted to 1 ug/ml in HBS-EP. HLA-E tetramer was tested in 5 ug/ml conc. Each cycle consisted of initial injection of a given construct, followed by injection of HLA-E tetramer. Construct and HLA-E tetramer were injected for 3 min., each followed by a 2.5 min. dissociation phase, prior to regeneration of the sensor chip surface.

All constructs were tested as stored at 4° C., and at −20° C.

All constructs, except NKG2A-mFc homodimer, demonstrated binding to immobilized HP-3D9. Binding of the individual constructs to HP-3D9 appeared not to be affected by the storage conditions, except for the CD94-mFc/NKG2A heterodimer with single mutation construct, where an apparent reduction in the on-rate could be detected for the construct stored at −20° C. However the construct did bind immobilized HP-3D9.

The apparent off-rate of the CD94-mFc/NKG2A heterodimer with double mutation construct was higher as compared to the other constructs which demonstrated apparent identical dissociation patterns. All constructs, except the CD94-mFc/NKG2A heterodimer with double mutation, demonstrated stable binding during the 2.5 min. dissociation phase.

No binding of HLA-E tetramer to any of the individual constructs in complex with HP-3D9 was detected.

Binding to immobilized Z199 was observed for the CD94-NKG2A-mFc singlechain, CD94-mFc/NKG2A heterodimer and CD94-mFc/NKG2A heterodimer with double mutation constructs irrespective of the storage conditions. Also, binding of the CD94-mFc/NKG2A heterodimer with single mutation construct stored at 4° C. was detected, while the same construct stored at −20° C. demonstrated no binding. Although binding of the CD94-mFc/NKG2A heterodimer and CD94-mFc/NKG2A heterodimer with single mutation constructs was detected, their association to immobilized Z199 appeared reduced as compared to that of the CD94-NKG2A-mFc singlechain and CD94-mFc/NKG2A heterodimer with double mutation constructs.

While the binding of the CD94-NKG2A-mFc singlechain, CD94-mFc/NKG2A heterodimer and CD94-mFc/NKG2A heterodimer with single mutation (4° C. storage) appear stable during the 2.5 min. dissociation phase, dissociation of CD94-mFc/NKG2A heterodimer with double mutation was fairly fast.

Binding of HLA-E tetramer to a construct in complex with Z199, was detected for the CD94-NKG2A-mFc singlechain construct. The binding of HLA-E tetramer appeared stable during the 2.5 min. dissociation period.

All constructs, except NKG2A-mFc homo dimer, bind to immobilized RaM. Again, the association of the CD94-mFc/NKG2A heterodimer with single mutation construct stored at −20° C. appear reduced compared to the same construct stored at 4° C.

Binding of HLA-E tetramer to complexes between RaM and the individual constructs was observed for all constructs, except for the NKG2A-mFc homodimer. The relative highest amounts of HLA-E tetramer bound, was detected for the CD94-NKG2A-mFc singlechain and CD94-mFc/NKG2A heterodimer with double mutation complexes.

Example 19

Binding of TRX-His-Tag-NKG2a-GSS-GSS-CD94-His-Tag/pET32a to Anti-CD94 and Anti-CD94/NKG2A Monoclonal Antibodies

*E Coli* expressed THX-His-tag-NKG2a-GSS-GSS-CD94-His-Tag/pET32a was analyzed for binding to immobilized HP-3D9 and Z199 monoclonal antibodies (see Example 18). Two different preparations prepared at pH 6.0, 7.0 and 8.0 respectively, were tested; one obtained from a 250 ml fermentation (B3), and one from a 1 L fermentation (B12) (see Examples 15 and 16).

Figure 24:
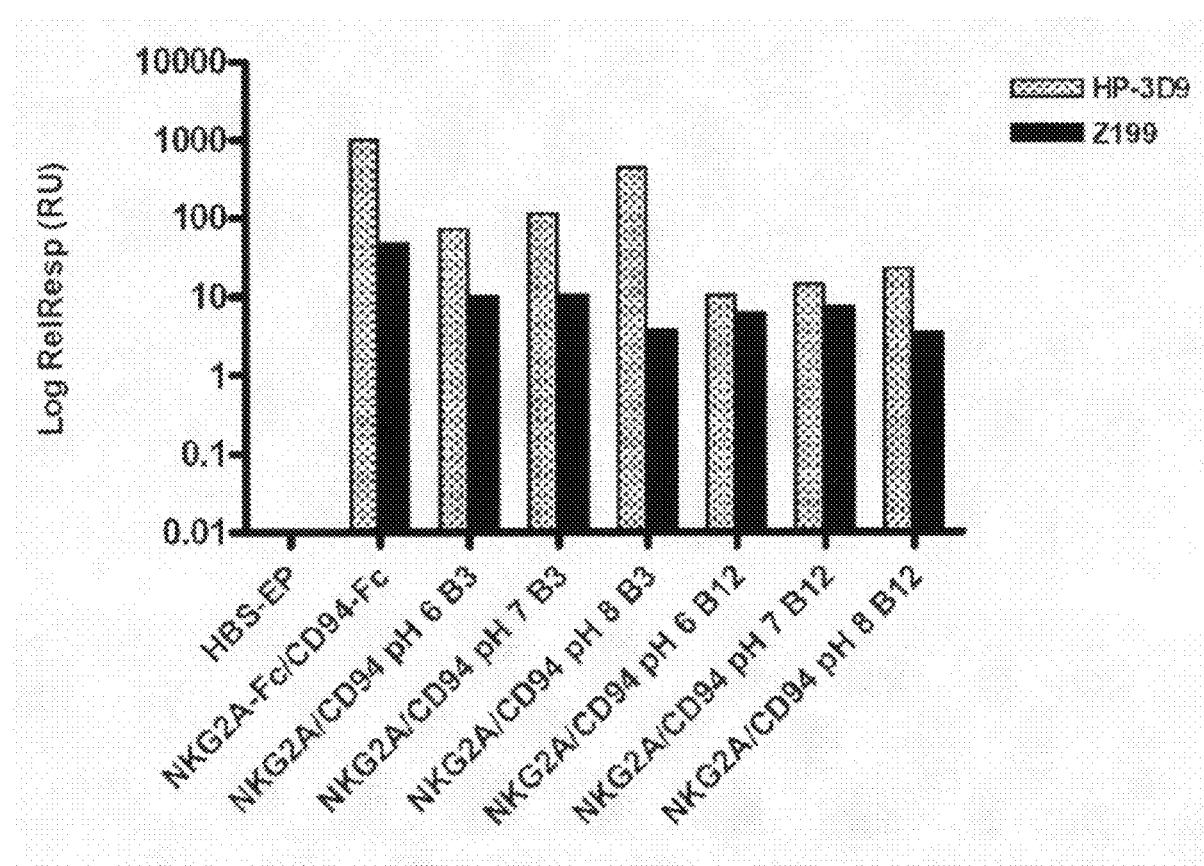
FIG. 24: Binding of single-chain NKG2A/CD94 construct (mFc-GS-NKG2A-GGS-GGS-RSS-CD94) to anti-NKG2A (Z199, light grey) and anti-CD94 (HP-3D9, dark grey) antibodies (Example 19).

The preparations from the 250 ml fermentation were tested in 1:10 dilution in HBS-EP, and injected for 3 min., followed by 2.5 min. dissociation. The preparations bound to both immobilized HP-3D9 and immobilized Z199, with higher amounts bound to immobilized HP-3D9 (FIG. 24).

The preparations from the 1 L fermentation were diluted to 10 ug/ml, and injected for 3 min., followed by 2.5 min. dissociation. This preparation also demonstrated binding to both immobilized HP-3D9 and Z199 (FIG. 24).

Example 20

Design and Production of mFc-hNKG2C-hCD94 Expression Constructs

Soluble human NKG2C was ordered from Geneart, Regensburg, Deutschland. The sequence was ordered with a 5' BamHI restriction site and a 3' HindIII restriction site in order to easily replace hNKG2A from pBF17 resulting in pBF74 (NKG2C/CD94-Fc) (SEQ ID NO:59):

```
  1 MPLLLLLPLL WAGALAMDVP RDCGCKPCIC TVPEVSSVFI FPPKPKDVLT

51 ITLTPKVTCV VVDISKDDPE VQFSWFVDDV EVHTAQTKPR EEQFNSTFRS

101 VSELPIMHQD WLNGKEFKCR VNSAAFPAPI EKTISKTKGR PKAPQVYTIP
```

```
151 PPKEQMAKDK VSLTCMITDF FPEDITVEWQ WNGQPAENYK NTQPIMDTDG

201 SYFVYSKLNV QKSNWEAGNT FTCSVLHEGL HNHHTEKSLS HSPGKGSFLE

251 QNNSSPNTRT QKARHCGHCP EEWITYSNSC YYIGKERRTW EESLLACTSK

301 NSSLLSIDNE EEMKFLASIL PSSWIGVFRN SSHHPWVTIN GLAFKHKIKD

351 SDNAELNCAV LQVNRLKSAQ CGSSMIYHCK HKLGGSGGSR SSFTKLSIEP

401 AFTPGPNIEL QKDSDCCSCQ EKWVGYRCNC YFISSEQKTW NESRHLCASQ

451 KSSLLQLQNT DELDFMSSSQ QFYWIGLSYS EEHTAWLWEN GSALSQYLFP

501 SFETFNTKNC IAYNPNGNAL DESCEDKNRY ICKQQLI
```

The construct comprise the signal peptide CD33 (SEQ ID NO:30), an 227 Fc-portion (Hinge-CH2-CH3) (SEQ ID NO:21), linker (GS), residues 96-231 of hNKG2C (SEQ ID NO:3), an GGSGGSRSS spacer and residues 34 to 180 of hCD94 (SEQ ID NO:2).

Mutated NKG2A-Portion Constructs for Mammalian Cell Expression

The amino acid sequences of the soluble portions of NKG2A and NKG2C used in the single chain constructs differ only in residues 99, 100, 101, 106, 167, 168, 170, 189 and 197, using the numbering of the alignment in FIG. 25. Note that the sequences used in the single-chain constructs starts at position 98 for NKG2C (FLEQ . . . ) and at 99 for NKG2A (QRH . . . ) according to the above numbering scheme.

A series of CD94/NKG2C-single chain constructs were developed based on the single chain construct (Sig)-(mFc)-GS-(NKG2A)-GGS-GGS-RSS-(CD94) (SEQ ID NO:39). This construct comprises residues 34 to 180 of hCD94 (SEQ ID NO:2), residues 99-233 of hNKG2A (SEQ ID NO:1), an GGSGGSRSS spacer between the CD94 and NKG2A portions, and an 227 Fc-portion. The series was prepared with iterative mutations listed in Table 4 below:

TABLE 4

| Iterative mutations to convert ssCD94/NKG2A to ssCD94/NKG2C construct | |
|---|---|
| Mut1 | Q99L, R100E, H101Q, L106P |
| Mut2 | S167A, I168S, S170L |
| Mut3 | M189I |
| Mut4 | E197K |
| Mut5 | I225M |

Mutations in the hNKG2A part were achieved using quikchange mutagenesis on the construct pBF17(SEQ ID NO:39). The primers used in the quikchange mutagenesis were:

Mut1 LEQ-P; Forward (SEQ ID NO:60), Reverse (SEQ ID NO:61)

Mut2 AS-L; Forward (SEQ ID NO:62), Reverse (SEQ ID NO:63)

Mut3 I; Forward (SEQ ID NO:64), Reverse (SEQ ID NO:65)

Mut4 K; Forward (SEQ ID NO:66), Reverse (SEQ ID NO:67)

Mut5 M; Forward (SEQ ID NO:68); Reverse (SEQ ID NO:69)

These mutations were carried out using QuikChange II Site-directed Mutagenesis Kit and manual from Stratagene #200523: A single denaturering step at 95° C./30 sec was followed by 15 cycles as given: 95° C./30 sec; 55° C./1 min; 68° C./7 min., ending with 72° C./10 min.

Example 21

SPR Study of Anti-NKG2A or -NKG2C Antibodies Binding to scCD94/NKG2A or scCD94/NKG2C Recombinant Proteins Materials & Methods Surface plasmon resonance (SPR) measurements were performed on a Biacore T100 apparatus (Biacore GE Healthcare) at 25° C. In all Biacore experiments HBS-EP+buffer (Biacore GE Healthcare) served as running buffer and sensorgrams were analyzed with Biaevaluation 4.1 and Biacore T100 Evaluation softwares. The antibodies used were anti-NKG2A (humZ270 and Z199), anti-NKG2C (Immunotech-Beckman Coulter), and anti-NKG2D (ON72).

Protein Immobilization.

Recombinant proteins were immobilized covalently to carboxyl groups in the dextran layer on a Sensor Chip CM5 (chip). The chip surface was activated with EDC/NHS (N-ethyl-N'-(3-dimethylaminopropyl) carbodiimidehydrochloride and N-hydroxysuccinimide (Biacore GE Healthcare)). Proteins were diluted to 10 µg/ml in coupling buffer (10 mM acetate, pH 5.6) and injected until the appropriate immobilization level was reached (i.e. 700, 630 and 400 RU for 2A, 2C and 2D respectively).

Deactivation of the remaining activated groups was performed using 100 mM ethanolamine pH 8 (Biacore GE Healthcare).

Binding Study

For simple binding experiments, antibodies were injected at a constant concentration of 10 µl g/ml for 1 minute at a flow rate of 10 µl/min onto the scCD94/NKG2A, scCD94/NKG2C and NKG2D-Fc recombinant protein chips. After each cycle, the chips were regenerated by an eight second injection of 500 mM NaCl and 10 mM NaOH buffer at flow rate of 40 µl/min. For each antibody the sensorgrams obtained on the different protein chips were superimposed and normalised to an arbitrary value of 100 RU for the Y axis.

Affinity Measurement

For kinetic experiments, serial dilutions from 0.078 to 5 nanoM of soluble antibodies were injected for 2 min at a constant flow rate of 40 µl/min on dextran layers containing immobilized scCD94/NKG2A recombinant proteins and allowed to dissociate for 3 min before regeneration by an eight second injection of 500 mM NaCl and 10 mM NaOH buffer.

The resulting sensorgrams were analysed by global fitting using the appropriate Langmuir model.

HLA-E Tetramers Binding Inhibition

For inhibition experiments, antibodies were injected at a constant concentration of 10 µg/ml on dextran layers containing immobilized scCD94/NKG2A recombinant target proteins. Each competition cycle consisted of three 2 min injection steps at a constant flow rate of 10 µl/min. Firstly, the antibody is injected twice. Secondly, without removing the bound antibody, the HLA-E tetramer at 8 µg/ml is injected and sensorgrams and RU values are monitored. The binding signals of the HLA-E tetramer in the presence of antibodies are compared to those obtained when the HLA-E tetramer is injected directly on nude recombinant scCD94/NKG2A proteins. The percentage of inhibition (I%) was determined from RU values obtained 10 second after the end of injections, using the following formula: I% =(1−(RU+Ab/RUNone))*100. RU+Ab and RUNone are HLA-E binding RU values monitored respectively in the presence and in the absence of an antibody. The sensorgrams corresponding to HLA-E injection (third step) were aligned to zero at the injection start for both X and Y axis and superimposed.

After each cycle, the chips were regenerated by an eight second injection of 500 mM NaCl and 10 mM NaOH buffer at flow rate of 40 µl/min.

Results

Figure 26:
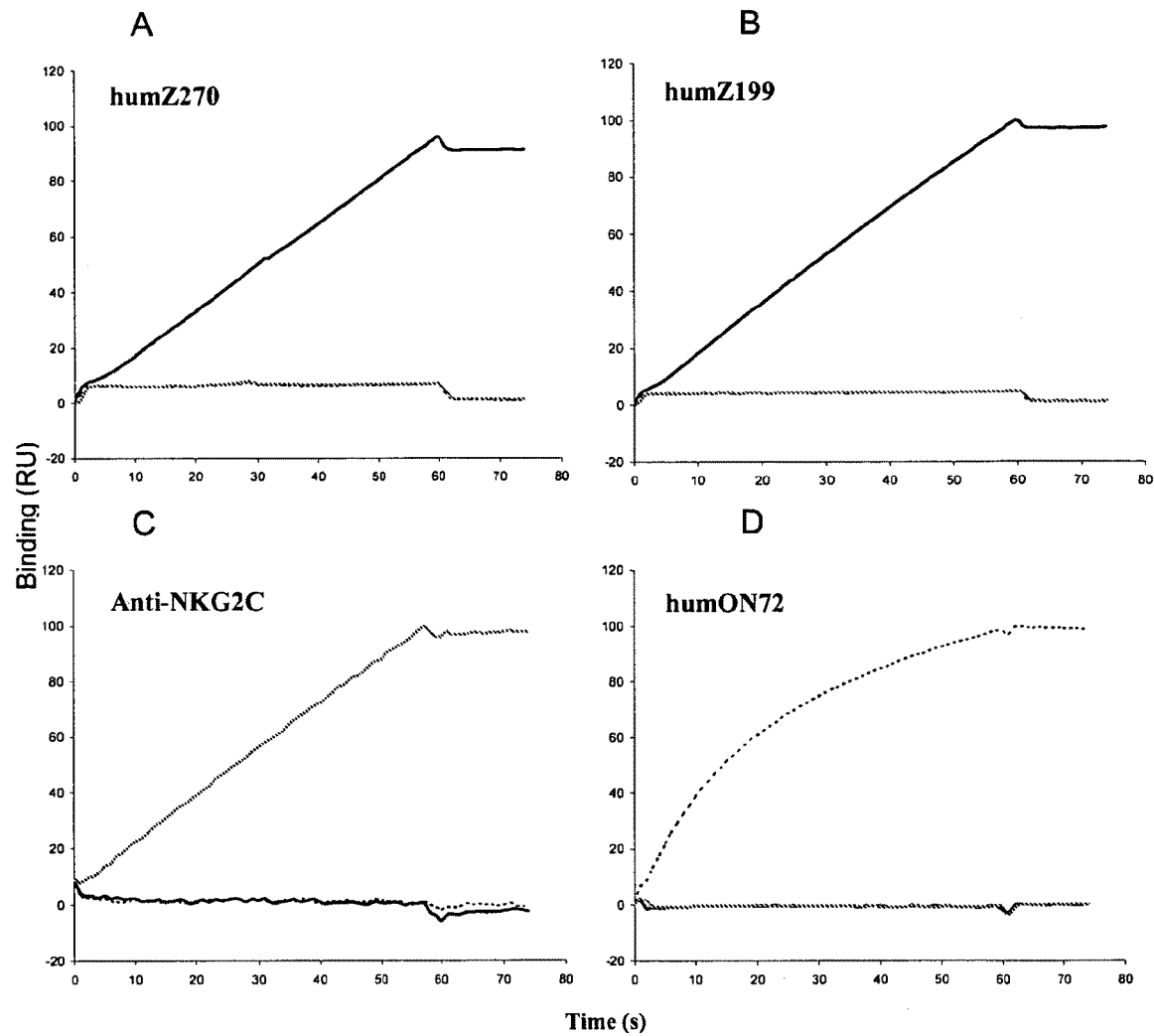
FIG. 26: Superimposed sensorgrams showing humZ270, humZ199, anti-NKG2C-PE and humON72 binding to scCD94/NKG2A chip (solid black line), scCD94/NKG2C chip (grey line) and NKG2D-Fc chip (dashed line). Antibodies at 10 µg/ml were injected for one minute at a flow rate of 10 µl/min.

The binding of humZ270 and humZ199 antibodies to recombinant NKG2A, NKG2C and NKG2D proteins was analysed by SPR (FIG. 26). Both antibodies bound to the scCD94/NKG2A chip whereas they did not bind to the scCD94/NKG2C chip. NKG2D-Fc proteins were used as a negative control.

The scCD94/NKG2C chip was checked using anti-NKG2C-PE (FAB138P, R&D Systems), injected at 2.5 µg/ml for 1 min onto the NKG2C chip. This antibody binds well to native NKG2C expressed at the cell surface. The antibody bound to the scCD94/NKG2C chip, indicating the presence of immobilized proteins in a proper status that mimics the cell surface situation. The NKG2D-Fc chip was checked using humON72 antibodies.

To analyse the HLA-E binding properties, the binding of HLA-E tetramers to scCD94/NKG2A chips was monitored in the absence and in the presence of humZ270. The saturation of scCD94/NKG2A chips using humZ270 antibodies completely inhibits the binding of HLA-E tetramers (IZ270=81.8%).

EXEMPLARY EMBODIMENTS

1. A single-chain soluble CD94/NKG2 receptor comprising a soluble portion of an NKG2 amino acid sequence and a soluble portion of a CD94 amino acid sequence.
2. The single-chain construct of embodiment 1, further comprising an immunoglobulin polypeptide comprising all or part of an Fc domain or variant thereof.
3. The single-chain soluble CD94/NKG2 receptor of embodiment 2, wherein the C-terminal of the soluble portion of a CD94 amino acid sequence is linked to the N-terminal of the soluble portion of an NKG2 amino acid sequence, and the C-terminal of the soluble portion of an NKG2 amino acid sequence is linked to the immunoglobulin polypeptide.
4. The single-chain soluble CD94/NKG2 receptor of embodiment 2, wherein the C-terminal of the soluble portion of an NKG2 amino acid sequence is linked to the N-terminal of the soluble portion of a CD94 amino acid sequence, and the C-terminal of the soluble portion of a CD94 amino acid sequence is linked to the immunoglobulin polypeptide.
5. The single-chain soluble CD94/NKG2 receptor of any of embodiments 3 and 4, wherein the soluble portion of an NKG2 amino acid sequence and soluble portion of a CD94 amino acid sequence are linked by a peptide linker comprising glycine and serine.
6. A dimer of the single-chain soluble CD94/NKG2 receptor of any of the preceding embodiments.
7. A soluble CD94/NKG2 receptor comprising an NKG2 subunit comprising a soluble portion of an NKG2 amino acid sequence and a CD94 subunit comprising a soluble portion of an CD94 amino acid sequence, wherein at least one of the NKG2 subunit and CD94 subunit comprises an immunoglobulin polypeptide comprising all or part of an Fc domain or variant thereof.
8. The soluble CD94/NKG2 receptor of embodiment 7, wherein the immunoglobulin polypeptide comprises a portion of an IgG Fc domain which increases the in vivo half-life of the construct.
9. The soluble CD94/NKG2 receptor of any of embodiments 7-8, wherein the immunoglobulin polypeptide is a functional Fc domain.
10. The soluble CD94/NKG2 receptor of any of embodiments 7-9, wherein the Fc domain is from an IgG4 antibody.
11. The soluble CD94/NKG2 receptor of any of embodiment 7-10, wherein the Fc domain is from an IgG1 antibody.
12. The soluble CD94/NKG2 receptor of any of embodiments 7-11, wherein only one of the NKG2A and CD94 subunits comprises an immunoglobulin polypeptide.
13. The soluble CD94/NKG2 receptor of embodiment 12, wherein the immunoglobulin polypeptide is linked to the C-terminal portion of the subunit.
14. The soluble CD94/NKG2 receptor of any of embodiments 12-13, wherein the NKG2A and CD94 subunits are linked via a peptide linker.
15. The soluble CD94/NKG2 receptor of embodiment 13, wherein the peptide linker comprises the sequence GGSGGS (SEQ ID NO:6).
16. The soluble CD94/NKG2 receptor of any of embodiments 12-15, wherein the NKG2 subunit is covalently bound to the immunoglobulin polypeptide.
17. The soluble CD94/NKG2 receptor of any of embodiments 12-15, wherein the CD94 subunit is covalently bound to the immunoglobulin polypeptide.
18. The soluble CD94/NKG2 receptor of embodiment 7, wherein each of the NKG2 and CD94 subunits is covalently bound to an immunoglobulin polypeptide.
19. The soluble CD94/NKG2 receptor of embodiment 18, wherein the N-terminal of the NKG2 subunit is linked to the C-terminal of a first immunoglobulin polypeptide so as to form a first polypeptide, and the N-terminal of the CD94 subunit is linked to the C-terminal of a second immunoglobulin polypeptide so as to form a second polypeptide.
20. The soluble CD94/NKG2 receptor of embodiment 19, wherein the first immunoglobulin polypeptide comprises a lysine at a residue corresponding to residue 239 and an aspartic acid at a residue corresponding to residue 292 in a human IgG1 Fc domain, and the second immunoglobulin polypeptide comprises a lysine at a residue corresponding to residue 282 and an aspartic acid at a residue corresponding to residue 322 in a human IgG1 Fc domain.

21. The soluble CD94/NKG2 receptor of any of embodiments 19 and 20, wherein the first immunoglobulin polypeptide comprises lysine at residues corresponding to residues 239 and 240 and an aspartic acid at a residue corresponding to residue 292 in a human IgG1 FC domain, and the second immunoglobulin polypeptide comprises a glutamic acid at a residue corresponding to residue 253, a lysine at a residue corresponding to residue 282, and an aspartic acid at a residue corresponding to residue 322 in a human IgG1 Fc domain.

22. The soluble CD94/NKG2 receptor of any of embodiments 20 and 21, wherein both the first and second immunoglobulin polypeptides are variants of a human IgG1 Fc domain, the first immunolobulin polypeptide comprising substitutions corresponding to K253E, D282K, and K322D, and the second immunoglobulin polypeptide comprising substitutions corresponding to D239K, E240K, and K292D, or vice versa.

23. The soluble CD94/NKG2 receptor of any of embodiments 20 and 21, wherein both the first and second immunoglobulin polypeptides are variants of a human IgG4 Fc domain, the first immunolobulin polypeptide comprising substitutions corresponding to K250E, D279K, and K319D, and the second immunoglobulin polypeptide comprising substitutions corresponding to E236K, E237K, R289D, or vice versa.

24. The soluble CD94/NKG2 receptor of any of the preceding embodiments, which is CD94/NKG2A.

25. The soluble CD94/NKG2A receptor of embodiment 25, wherein the NKG2A subunit comprises residues 99-233 of SEQ ID NO:1.

26. The soluble CD94/NKG2 receptor of any of embodiments 1-23, which is CD94/NKG2C.

27. The soluble CD94/NKG2C receptor of embodiment 26, wherein the NKG2C subunit comprises residues 96-231 of SEQ ID NO:3.

28. The soluble CD94/NKG2 receptor of any of the preceding embodiments, wherein the CD94 amino acid sequence is SEQ ID NO:2.

29. The soluble CD94/NKG2A receptor of embodiment 28, wherein the CD94 subunit comprises residues 35-179 of SEQ ID NO:2.

30. The soluble CD94/NKG2 receptor of any of the preceding embodiments, wherein the immunoglobulin polypeptide is covalently bound to a signal sequence.

31. A soluble CD94/NKG2A receptor comprising the sequence of any of SEQ ID NOS:37-39.

32. A soluble CD94/NKG2C receptor comprising the sequence of SEQ ID NO:59.

33. A nucleic acid encoding the soluble CD94/NKG2 receptor of any of the preceding embodiments.

34. A cell transformed with an expression vector comprising the nucleic acid of embodiment 33.

35. The cell of embodiment 34, which is a prokaryotic cell or eukaryotic cell.

36. A method of producing a soluble CD94/NKG2 receptor, comprising culturing the cell of embodiment 35 under conditions suitable for expression of the soluble CD94/NKG2 receptor.

37. A pharmaceutical composition comprising an effective amount of the soluble CD94/NKG2 receptor of any of embodiments 1 to 32 and a pharmaceutically acceptable carrier or excipient.

38. A method of producing an antibody against a CD94/NKG2 receptor, the method comprising:
   a. inoculating an animal with a soluble CD94/NKG2 receptor of any of embodiments 1 to 32, wherein the polypeptide elicits an immune response in the animal to produce the antibody; and
   b. isolating the antibody from the animal.

39. A method of detecting an HLA-E molecule, the method comprising:
   a. contacting a biological sample comprising an HLA-E expressing cell with a soluble CD94/NKG2 receptor of any of embodiments 1 to 32; and
   b. detecting binding of the soluble CD94/NKG2 receptor to the cell.

40. A method of producing an anti-NKG2 antigen-binding compound, the method comprising:
   a. providing an antigen-binding compound that specifically binds to an NKG2 polypeptide;
   b. testing the antigen-binding compound for binding to a soluble CD94/NKG2A receptor of any of embodiments 1 to 32;
   c. selecting the antigen-binding compound if it is determined that the antigen-binding compound binds to the soluble CD94/NKG2A receptor; and
   d. optionally, producing a quantity of the selected antigen-binding compound.

41. A method of producing an anti-NKG2 antigen-binding compound, the method comprising:
   a. producing a quantity of an antigen-binding compound that specifically binds to an NKG2 polypeptide;
   b. testing a sample from said quantity of an antigen-binding compound for binding to a soluble CD94/NKG2 receptor of any of embodiments 1 to 32;
   c. selecting the quantity for use as a medicament and/or in the manufacture of a medicament if it is determined that the antigen-binding compound binds to the soluble CD94/NKG2 receptor; and
   d. optionally, preparing the quantity for administration to a human, optionally formulating a quantity of the selected antigen-binding compound with a pharmaceutically acceptable carrier.

42. A method of producing an anti-NKG2 antigen-binding compound, the method comprising:
   a. providing a plurality of antigen-binding compounds that specifically bind to an NKG2 polypeptide,
   b. testing each of the antigen-binding compounds for binding to a soluble CD94/NKG2 receptor of any of embodiments 1 to 32;
   c. selecting an antigen-binding compound if it is determined that the antigen-binding compound binds to said soluble CD94/NKG2 receptor; and
   d. optionally, making the antigen-binding compound suitable for human administration; and/or
   e. optionally, producing a quantity of the selected antigen-binding compound.

43. The method of any of embodiments 40 to 42, wherein making the antigen-binding compound human suitable comprises making the antigen-binding compound chimeric or humanized.

44. The method of any one of embodiments 40-43, wherein producing a quantity of antigen-binding compound comprises culturing a cell expressing the antigen-binding compound in a suitable medium and recovering the antigen-binding compound.

45. The method of any of embodiments 40-44, wherein the antigen-binding compound comprises an antibody or an antigen-binding fragment thereof.

46. The method of any of embodiments 40-45, wherein the antigen-binding compound is an antibody.

47. The method of any of embodiments 40-46, wherein the NKG2 polypeptide is NKG2A.

48. The method of any of embodiments 40-46, wherein the NKG2 polypeptide is NKG2C.

All references, including publications, patent applications and patents, cited herein are hereby incorporated by reference to the same extent as if each reference was individually and specifically indicated to be incorporated by reference and was set forth in its entirety herein.

All headings and sub-headings are used herein for convenience only and should not be construed as limiting the invention in any way, Any combination of the above-described elements in all possible variations thereof is encompassed by the invention unless otherwise indicated herein or otherwise clearly contradicted by context.

The terms "a" and "an" and "the" and similar referents as used in the context of describing the invention are to be construed to cover both the singular and the plural, unless otherwise indicated herein or clearly contradicted by context.

Recitation of ranges of values herein are merely intended to serve as a shorthand method of referring individually to each separate value falling within the range, unless otherwise indicated herein, and each separate value is incorporated into the specification as if it were individually recited herein. Unless otherwise stated, all exact values provided herein are representative of corresponding approximate values (e.g., all exact exemplary values provided with respect to a particular factor or measurement can be considered to also provide a corresponding approximate measurement, modified by "about," where appropriate).

All methods described herein can be performed in any suitable order unless otherwise indicated herein or otherwise clearly contradicted by context.

The use of any and all examples, or exemplary language (e.g., "such as") provided herein, is intended merely to better illuminate the invention and does not pose a limitation on the scope of the invention unless otherwise indicated. No language in the specification should be construed as indicating any element is essential to the practice of the invention unless as much is explicitly stated.

The citation and incorporation of patent documents herein is done for convenience only and does not reflect any view of the validity, patentability and/or enforceability of such patent documents, The description herein of any aspect or embodiment of the invention using terms such as "comprising", "having", "including" or "containing" with reference to an element or elements is intended to provide support for a similar aspect or embodiment of the invention that "consists of", "consists essentially of", or "substantially comprises" that particular element or elements, unless otherwise stated or clearly contradicted by context (e.g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The invention claimed is:

1. A soluble CD94/NKG2 receptor fusion protein comprising a soluble portion of an NKG2 amino acid sequence and a soluble portion of a CD94 amino acid sequence wherein said fusion protein binds HLA-E.

2. The soluble CD94/NKG2 receptor fusion protein of claim 1, further comprising an immunoglobulin polypeptide comprising all or part of an Fc domain or variant thereof.

3. The soluble CD94/NKG2 receptor fusion protein of claim 2, wherein the C-terminal of the soluble portion of a CD94 amino acid sequence is linked to the N-terminal of the soluble portion of an NKG2 amino acid sequence, and the C-terminal of the soluble portion of an NKG2 amino acid sequence is linked to the immunoglobulin polypeptide.

4. The soluble CD94/NKG2 receptor fusion protein of claim 2, wherein the C-terminal of the soluble portion of an NKG2 amino acid sequence is linked to the N-terminal of the soluble portion of a CD94 amino acid sequence, and the C-terminal of the soluble portion of a CD94 amino acid sequence is linked to the immunoglobulin polypeptide.

5. The soluble CD94/NKG2 receptor fusion protein of claim 3, wherein the soluble portion of an NKG2 amino acid sequence and soluble portion of a CD94 amino acid sequence are linked by a peptide linker comprising glycine and serine.

6. The soluble CD94/NKG2 receptor fusion protein of claim 1, which is a CD94/NKG2A, CD94/NKG2B, CD94/NKG2C, CD94/NKG2E, or CD94/NKG2F receptor fusion protein.

7. The soluble CD94/NKG2 receptor fusion protein of claim 6, which is CD94/NKG2A.

8. The soluble CD94/NKG2A receptor fusion protein of claim 7, comprising residues 99-233 of SEQ ID NO: 1.

9. The soluble CD94/NKG2 receptor fusion protein of claim 6, which is CD94/NKG2C.

10. The soluble CD94/NKG2C receptor fusion protein of claim 9, comprising residues 96-231 of SEQ ID NO: 3.

11. The soluble CD94/NKG2 receptor fusion protein of claim 1, comprising residues 35-179 of SEQ ID NO: 2.

12. A soluble CD94/NKG2A receptor fusion protein comprising the sequence of any one of SEQ ID NOS: 37-39.

13. A dimer of the soluble CD94/NKG2 receptor fusion protein of claim 1.

14. A method of producing a soluble CD94/NKG2 receptor fusion protein, comprising culturing a cell comprising a nucleic acid encoding the soluble CD94/NKG2 receptor fusion protein of claim 1 under conditions suitable for expression of the soluble CD94/NKG2 receptor fusion protein.

15. A composition comprising the soluble CD94/NKG2 receptor fusion protein of claim 1 and a pharmaceutically acceptable carrier or excipient.

16. The soluble CD94/NKG2 receptor fusion protein of claim 4, wherein the soluble portion of an NKG2 amino acid sequence and soluble portion of a CD94 amino acid sequence are linked by a peptide linker comprising glycine and serine.

17. A dimer of the soluble CD94/NKG2 receptor fusion protein of claim 7.

18. A dimer of the soluble CD94/NKG2 receptor fusion protein of claim 8.

19. A composition comprising the soluble CD94/NKG2 receptor fusion protein of claim 12 and a pharmaceutically acceptable carrier or excipient.

20. A method of producing a soluble CD94/NKG2 receptor fusion protein, comprising culturing a cell comprising a nucleic acid encoding the soluble CD94/NKG2 receptor fusion protein of claim 12 under conditions suitable for expression of the soluble CD94/NKG2 receptor fusion protein.

* * * * *

SEQUENCE LISTING

<160> NUMBER OF SEQ ID NOS: 69

<210> SEQ ID NO 1
<211> LENGTH: 233
<212> TYPE: PRT
<213> ORGANISM: Homo sapiens

<400> SEQUENCE: 1

Met Asp Asn Gln Gly Val Ile Tyr Ser Asp Leu Asn Leu Pro Pro Asn
1               5                   10                  15

Pro Lys Arg Gln Gln Arg Lys Pro Lys Gly Asn Lys Ser Ser Ile Leu
            20                  25                  30

Ala Thr Glu Gln Glu Ile Thr Tyr Ala Glu Leu Asn Leu Gln Lys Ala
        35                  40                  45

Ser Gln Asp Phe Gln Gly Asn Asp Lys Thr Tyr His Cys Lys Asp Leu
    50                  55                  60

Pro Ser Ala Pro Glu Lys Leu Ile Val Gly Ile Leu Gly Ile Ile Cys
65                  70                  75                  80

Leu Ile Leu Met Ala Ser Val Val Thr Ile Val Val Ile Pro Ser Thr
                85                  90                  95

Leu Ile Gln Arg His Asn Asn Ser Ser Leu Asn Thr Arg Thr Gln Lys
            100                 105                 110

Ala Arg His Cys Gly His Cys Pro Glu Glu Trp Ile Thr Tyr Ser Asn
        115                 120                 125

Ser Cys Tyr Tyr Ile Gly Lys Glu Arg Arg Thr Trp Glu Glu Ser Leu
    130                 135                 140

Leu Ala Cys Thr Ser Lys Asn Ser Ser Leu Leu Ser Ile Asp Asn Glu
145                 150                 155                 160

Glu Glu Met Lys Phe Leu Ser Ile Ile Ser Pro Ser Ser Trp Ile Gly

```
                165                 170                 175
Val Phe Arg Asn Ser Ser His His Pro Trp Val Thr Met Asn Gly Leu
            180                 185                 190

Ala Phe Lys His Glu Ile Lys Asp Ser Asp Asn Ala Glu Leu Asn Cys
            195                 200                 205

Ala Val Leu Gln Val Asn Arg Leu Lys Ser Ala Gln Cys Gly Ser Ser
            210                 215                 220

Ile Ile Tyr His Cys Lys His Lys Leu
225                 230

<210> SEQ ID NO 2
<211> LENGTH: 179
<212> TYPE: PRT
<213> ORGANISM: Homo sapiens

<400> SEQUENCE: 2

Met Ala Val Phe Lys Thr Thr Leu Trp Arg Leu Ile Ser Gly Thr Leu
1               5                   10                  15

Gly Ile Ile Cys Leu Ser Leu Met Ala Thr Leu Gly Ile Leu Leu Lys
            20                  25                  30

Asn Ser Phe Thr Lys Leu Ser Ile Glu Pro Ala Phe Thr Pro Gly Pro
            35                  40                  45

Asn Ile Glu Leu Gln Lys Asp Ser Asp Cys Cys Ser Cys Gln Glu Lys
        50                  55                  60

Trp Val Gly Tyr Arg Cys Asn Cys Tyr Phe Ile Ser Ser Glu Gln Lys
65                  70                  75                  80

Thr Trp Asn Glu Ser Arg His Leu Cys Ala Ser Gln Lys Ser Ser Leu
                85                  90                  95

Leu Gln Leu Gln Asn Thr Asp Glu Leu Asp Phe Met Ser Ser Ser Gln
            100                 105                 110

Gln Phe Tyr Trp Ile Gly Leu Ser Tyr Ser Glu Glu His Thr Ala Trp
            115                 120                 125

Leu Trp Glu Asn Gly Ser Ala Leu Ser Gln Tyr Leu Phe Pro Ser Phe
        130                 135                 140

Glu Thr Phe Asn Thr Lys Asn Cys Ile Ala Tyr Asn Pro Asn Gly Asn
145                 150                 155                 160

Ala Leu Asp Glu Ser Cys Glu Asp Lys Asn Arg Tyr Ile Cys Lys Gln
                165                 170                 175

Gln Leu Ile

<210> SEQ ID NO 3
<211> LENGTH: 231
<212> TYPE: PRT
<213> ORGANISM: Homo sapiens

<400> SEQUENCE: 3

Met Ser Lys Gln Arg Gly Thr Phe Ser Glu Val Ser Leu Ala Gln Asp
1               5                   10                  15

Pro Lys Arg Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Pro
            35                  40                  45

Ser Leu Asn His Gln Gly Ile Asp Lys Ile Tyr Asp Cys Gln Gly Leu
        50                  55                  60

Leu Pro Pro Pro Glu Lys Leu Thr Ala Glu Val Leu Gly Ile Ile Cys
65                  70                  75                  80
```

```
Ile Val Leu Met Ala Thr Val Leu Lys Thr Ile Val Leu Ile Pro Phe
                85                  90                  95

Leu Glu Gln Asn Asn Ser Ser Pro Asn Thr Arg Thr Gln Lys Ala Arg
            100                 105                 110

His Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Leu Ala
    130                 135                 140

Cys Thr Ser Lys Asn Ser Ser Leu Leu Ser Ile Asp Asn Glu Glu Glu
145                 150                 155                 160

Met Lys Phe Leu Ala Ser Ile Leu Pro Ser Ser Trp Ile Gly Val Phe
            165                 170                 175

Arg Asn Ser Ser His His Pro Trp Val Thr Ile Asn Gly Leu Ala Phe
        180                 185                 190

Lys His Lys Ile Lys Asp Ser Asp Asn Ala Glu Leu Asn Cys Ala Val
    195                 200                 205

Leu Gln Val Asn Arg Leu Lys Ser Ala Gln Cys Gly Ser Ser Met Ile
210                 215                 220

Tyr His Cys Lys His Lys Leu
225                 230

<210> SEQ ID NO 4
<211> LENGTH: 240
<212> TYPE: PRT
<213> ORGANISM: Homo sapiens

<400> SEQUENCE: 4

Met Asn Lys Gln Arg Gly Thr Phe Ser Glu Val Ser Leu Ala Gln Asp
1               5                   10                  15

Pro Lys Pro Gln Gln Arg Lys Pro Lys Gly Asn Lys Ser Ser Ile Ser
            20                  25                  30

Gly Thr Glu Gln Glu Ile Phe Gln Val Glu Leu Asn Leu Gln Asn Ala
        35                  40                  45

Ser Leu Asn His Gln Gly Ile Asp Lys Ile Tyr Asp Cys Gln Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Phe
                85                  90                  95

Leu Glu Gln Asn Asn Ser Ser Pro Asn Thr Arg Thr Gln Lys Ala Arg
            100                 105                 110

Pro Cys Gly His Cys Pro Glu Glu Trp Ile Thr Tyr Ser Asn Ser Cys
        115                 120                 125

Tyr Tyr Ile Gly Lys Glu Arg Arg Thr Trp Glu Glu Ser Leu Gln Ala
    130                 135                 140

Cys Ala Ser Lys Asn Ser Ser Leu Leu Ser Ile Asp Asn Glu Glu Glu
145                 150                 155                 160

Glu Met Lys Phe Leu Ala Ser Ile Leu Pro Ser Ser Trp Ile Gly Val
            165                 170                 175

Phe Arg Asn Ser Ser His His Pro Trp Val Thr Ile Asn Gly Leu Ala
        180                 185                 190

Phe Lys His Glu Ile Lys Asp Ser Asp His Ala Glu Arg Asn Cys Ala
    195                 200                 205

Met Leu His Val Arg Gly Leu Ile Ser Asp Gln Cys Gly Ser Ser Arg
210                 215                 220
```

```
Ile Ile Arg Arg Gly Phe Ile Met Leu Thr Arg Leu Val Leu Asn Ser
225                 230                 235                 240
```

<210> SEQ ID NO 5
<211> LENGTH: 158
<212> TYPE: PRT
<213> ORGANISM: Homo sapiens

<400> SEQUENCE: 5

```
Met Asn Lys Gln Arg Gly Thr Tyr Ser Glu Val Ser Leu Ala Gln Asp
1               5                   10                  15

Pro Lys Arg Gln Gln Arg Lys Leu Lys Gly Asn Lys Ser Ser Ile Ser
            20                  25                  30

Gly Thr Lys Gln Glu Ile Phe Gln Val Glu Leu Asn Leu Gln Asn Ala
        35                  40                  45

Ser Ser Asp His Gln Gly Asn Asp Lys Thr Tyr His Cys Lys Gly Leu
    50                  55                  60

Leu Pro Pro Pro Glu Lys Leu Thr Ala Glu Val Leu Gly Ile Ile Cys
65                  70                  75                  80

Ile Val Leu Met Ala Thr Val Leu Lys Thr Ile Val Leu Ile Pro Cys
                85                  90                  95

Ile Gly Val Leu Glu Gln Asn Ser Phe Ser Leu Asn Arg Arg Met Gln
            100                 105                 110

Lys Ala Arg His Cys Gly His Cys Pro Glu Glu Trp Ile Thr Tyr Ser
        115                 120                 125

Asn Ser Cys Tyr Tyr Ile Gly Lys Glu Arg Arg Thr Trp Glu Glu Arg
    130                 135                 140

Val Cys Trp Pro Val Leu Arg Arg Thr Leu Ile Cys Phe Leu
145                 150                 155
```

<210> SEQ ID NO 6
<211> LENGTH: 6
<212> TYPE: PRT
<213> ORGANISM: Artificial
<220> FEATURE:
<223> OTHER INFORMATION: Linker

<400> SEQUENCE: 6

```
Gly Gly Ser Gly Gly Ser
1               5
```

<210> SEQ ID NO 7
<211> LENGTH: 9
<212> TYPE: PRT
<213> ORGANISM: Artificial
<220> FEATURE:
<223> OTHER INFORMATION: Linker

<400> SEQUENCE: 7

```
Gly Gly Ser Gly Gly Ser Arg Ser Ser
1               5
```

<210> SEQ ID NO 8
<211> LENGTH: 330
<212> TYPE: PRT
<213> ORGANISM: Homo sapiens

<400> SEQUENCE: 8

```
Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30
```

```
Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
        50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 9
<211> LENGTH: 330
<212> TYPE: PRT
<213> ORGANISM: Homo sapiens

<400> SEQUENCE: 9

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80
```

```
Tyr Ile Cys Asn Val Asn His Lys Pro Ser Asn Thr Lys Val Asp Lys
                 85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 10
<211> LENGTH: 106
<212> TYPE: PRT
<213> ORGANISM: Homo sapiens

<400> SEQUENCE: 10

Thr Val Ala Ala Pro Ser Val Phe Ile Phe Pro Pro Ser Asp Glu Gln
1               5                   10                  15

Leu Lys Ser Gly Thr Ala Ser Val Cys Leu Leu Asn Asn Phe Tyr
            20                  25                  30

Pro Arg Glu Ala Lys Val Gln Trp Lys Val Asp Asn Ala Leu Gln Ser
        35                  40                  45

Gly Asn Ser Gln Glu Ser Val Thr Glu Gln Asp Ser Lys Asp Ser Thr
    50                  55                  60

Tyr Ser Leu Ser Ser Thr Leu Thr Leu Ser Lys Ala Asp Tyr Glu Lys
65                  70                  75                  80

His Lys Val Tyr Ala Cys Glu Val Thr His Gln Gly Leu Ser Ser Pro
                85                  90                  95

Val Thr Lys Ser Phe Asn Arg Gly Glu Cys
            100                 105

<210> SEQ ID NO 11
```

<211> LENGTH: 105
<212> TYPE: PRT
<213> ORGANISM: Homo sapiens

<400> SEQUENCE: 11

```
Gln Pro Lys Ala Ala Pro Ser Val Thr Leu Phe Pro Pro Ser Ser Glu
 1               5                  10                  15

Glu Leu Gln Ala Asn Lys Ala Thr Leu Val Cys Leu Ile Ser Asp Phe
            20                  25                  30

Tyr Pro Gly Ala Val Thr Val Ala Trp Lys Ala Asp Ser Ser Pro Val
        35                  40                  45

Lys Ala Gly Val Glu Thr Thr Pro Ser Lys Gln Ser Asn Asn Lys
 50                  55                  60

Tyr Ala Ala Ser Ser Tyr Leu Ser Leu Thr Pro Glu Gln Trp Lys Ser
65                  70                  75                  80

His Arg Ser Tyr Ser Cys Gln Val Thr His Glu Gly Ser Thr Val Glu
                85                  90                  95

Lys Thr Val Ala Pro Thr Glu Cys Ser
            100                 105
```

<210> SEQ ID NO 12
<211> LENGTH: 326
<212> TYPE: PRT
<213> ORGANISM: Rattus norvegicus

<400> SEQUENCE: 12

```
Ala Glu Thr Thr Ala Pro Ser Val Tyr Pro Leu Ala Pro Gly Thr Ala
 1               5                  10                  15

Leu Lys Ser Asn Ser Met Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Thr Ser Ser Val Thr Val Pro Ser Ser Thr Trp Pro Ser Gln Thr Val
65                  70                  75                  80

Thr Cys Asn Val Ala His Pro Ala Ser Ser Thr Lys Val Asp Lys Lys
                85                  90                  95

Ile Val Pro Arg Asn Cys Gly Gly Asp Cys Lys Pro Cys Ile Cys Thr
            100                 105                 110

Gly Ser Glu Val Ser Ser Val Phe Ile Phe Pro Pro Lys Pro Lys Asp
        115                 120                 125

Val Leu Thr Ile Thr Leu Thr Pro Lys Val Thr Cys Val Val Val Asp
    130                 135                 140

Ile Ser Gln Asp Asp Pro Glu Val His Phe Ser Trp Phe Val Asp Asp
145                 150                 155                 160

Val Glu Val His Thr Ala Gln Thr Arg Pro Pro Glu Glu Gln Phe Asn
                165                 170                 175

Ser Thr Phe Arg Ser Val Ser Glu Leu Pro Ile Leu His Gln Asp Trp
            180                 185                 190

Leu Asn Gly Arg Thr Phe Arg Cys Lys Val Thr Ser Ala Ala Phe Pro
        195                 200                 205

Ser Pro Ile Glu Lys Thr Ile Ser Lys Pro Glu Gly Arg Thr Gln Val
    210                 215                 220

Pro His Val Tyr Thr Met Ser Pro Thr Lys Glu Glu Met Thr Gln Asn
225                 230                 235                 240
```

```
Glu Val Ser Ile Thr Cys Met Val Lys Gly Phe Tyr Pro Asp Ile
                245                 250                 255

Tyr Val Glu Trp Gln Met Asn Gly Gln Pro Glu Asn Tyr Lys Asn
            260                 265                 270

Thr Pro Pro Thr Met Asp Thr Asp Gly Ser Tyr Phe Leu Tyr Ser Lys
        275                 280                 285

Leu Asn Val Lys Lys Glu Lys Trp Gln Gln Gly Asn Thr Phe Thr Cys
    290                 295                 300

Ser Val Leu His Glu Gly Leu His Asn His His Thr Glu Lys Ser Leu
305                 310                 315                 320

Ser His Ser Pro Gly Lys
                325

<210> SEQ ID NO 13
<211> LENGTH: 329
<212> TYPE: PRT
<213> ORGANISM: Mus musculus

<400> SEQUENCE: 13

Thr Thr Thr Ala Pro Ser Val Tyr Pro Leu Val Pro Gly Cys Ser Asp
1               5                   10                  15

Thr Ser Gly Ser Ser Val Thr Leu Gly Cys Leu Val Lys Gly Tyr Phe
            20                  25                  30

Pro Glu Pro Val Thr Val Lys Trp Asn Tyr Gly Ala Leu Ser Ser Gly
        35                  40                  45

Val Arg Thr Val Ser Ser Val Leu Gln Ser Gly Phe Tyr Ser Leu Ser
    50                  55                  60

Ser Leu Val Thr Val Pro Ser Ser Thr Trp Pro Ser Gln Thr Val Ile
65                  70                  75                  80

Cys Asn Val Ala His Pro Ala Ser Lys Thr Glu Leu Ile Lys Arg Ile
                85                  90                  95

Glu Pro Arg Ile Pro Lys Pro Ser Thr Pro Pro Gly Ser Ser Cys Pro
            100                 105                 110

Pro Gly Asn Ile Leu Gly Gly Pro Ser Val Phe Ile Phe Pro Pro Lys
        115                 120                 125

Pro Lys Asp Ala Leu Met Ile Ser Leu Thr Pro Lys Val Thr Cys Val
130                 135                 140

Val Val Asp Val Ser Glu Asp Asp Pro Asp Val His Val Ser Trp Phe
145                 150                 155                 160

Val Asp Asn Lys Glu Val His Thr Ala Trp Thr Gln Pro Arg Glu Ala
                165                 170                 175

Gln Tyr Asn Ser Thr Phe Arg Val Val Ser Ala Leu Pro Ile Gln His
            180                 185                 190

Gln Asp Trp Met Arg Gly Lys Glu Phe Lys Cys Lys Val Asn Asn Lys
        195                 200                 205

Ala Leu Pro Ala Pro Ile Glu Arg Thr Ile Ser Lys Pro Lys Gly Arg
    210                 215                 220

Ala Gln Thr Pro Gln Val Tyr Thr Ile Pro Pro Pro Arg Glu Gln Met
225                 230                 235                 240

Ser Lys Lys Lys Val Ser Leu Thr Cys Leu Val Thr Asn Phe Phe Ser
                245                 250                 255

Glu Ala Ile Ser Val Glu Trp Glu Arg Asn Gly Glu Leu Glu Gln Asp
            260                 265                 270

Tyr Lys Asn Thr Pro Pro Ile Leu Asp Ser Asp Gly Thr Tyr Phe Leu
        275                 280                 285
```

```
Tyr Ser Lys Leu Thr Val Asp Thr Asp Ser Trp Leu Gln Gly Glu Ile
        290                 295                 300

Phe Thr Cys Ser Val Val His Glu Ala Leu His Asn His His Thr Gln
305                 310                 315                 320

Lys Asn Leu Ser Arg Ser Pro Gly Lys
                325

<210> SEQ ID NO 14
<211> LENGTH: 330
<212> TYPE: PRT
<213> ORGANISM: Mus musculus

<400> SEQUENCE: 14

Ala Lys Thr Thr Ala Pro Ser Val Tyr Pro Leu Ala Pro Val Cys Gly
1               5                   10                  15

Asp Thr Thr Gly Ser Ser Val Thr Leu Gly Cys Leu Val Lys Gly Tyr
                20                  25                  30

Phe Pro Glu Pro Val Thr Leu Thr Trp Asn Ser Gly Ser Leu Ser Ser
            35                  40                  45

Gly Val His Thr Phe Pro Ala Val Leu Gln Ser Asp Leu Tyr Thr Leu
        50                  55                  60

Ser Ser Ser Val Thr Val Thr Ser Ser Thr Trp Pro Ser Gln Ser Ile
65                  70                  75                  80

Thr Cys Asn Val Ala His Pro Ala Ser Ser Thr Lys Val Asp Lys Lys
                85                  90                  95

Ile Glu Pro Arg Gly Pro Thr Ile Lys Pro Cys Pro Pro Cys Lys Cys
            100                 105                 110

Pro Ala Pro Asn Leu Leu Gly Gly Pro Ser Val Phe Ile Phe Pro Pro
        115                 120                 125

Lys Ile Lys Asp Val Leu Met Ile Ser Leu Ser Pro Ile Val Thr Cys
130                 135                 140

Val Val Val Asp Val Ser Glu Asp Asp Pro Asp Val Gln Ile Ser Trp
145                 150                 155                 160

Phe Val Asn Asn Val Glu Val His Thr Ala Gln Thr Gln Thr His Arg
                165                 170                 175

Glu Asp Tyr Asn Ser Thr Leu Arg Val Val Ser Ala Leu Pro Ile Gln
            180                 185                 190

His Gln Asp Trp Met Ser Gly Lys Glu Phe Lys Cys Lys Val Asn Asn
        195                 200                 205

Lys Asp Leu Pro Ala Pro Ile Glu Arg Thr Ile Ser Lys Pro Lys Gly
210                 215                 220

Ser Val Arg Ala Pro Gln Val Tyr Val Leu Pro Pro Pro Glu Glu Glu
225                 230                 235                 240

Met Thr Lys Lys Gln Val Thr Leu Thr Cys Met Val Thr Asp Phe Met
                245                 250                 255

Pro Glu Asp Ile Tyr Val Glu Trp Thr Asn Asn Gly Lys Thr Glu Leu
            260                 265                 270

Asn Tyr Lys Asn Thr Glu Pro Val Leu Asp Ser Asp Gly Ser Tyr Phe
        275                 280                 285

Met Tyr Ser Lys Leu Arg Val Glu Lys Lys Asn Trp Val Glu Arg Asn
290                 295                 300

Ser Tyr Ser Cys Ser Val Val His Glu Gly Leu His Asn His His Thr
305                 310                 315                 320

Thr Lys Ser Phe Ser Arg Thr Pro Gly Lys
                325                 330
```

```
<210> SEQ ID NO 15
<211> LENGTH: 335
<212> TYPE: PRT
<213> ORGANISM: Mus musculus

<400> SEQUENCE: 15

Ala Lys Thr Thr Ala Pro Ser Val Tyr Pro Leu Val Pro Val Cys Gly
1               5                   10                  15

Gly Thr Thr Gly Ser Ser Val Thr Leu Gly Cys Leu Val Lys Gly Tyr
            20                  25                  30

Phe Pro Glu Pro Val Thr Leu Thr Trp Asn Ser Gly Ser Leu Ser Ser
        35                  40                  45

Gly Val His Thr Phe Pro Ala Leu Leu Gln Ser Gly Leu Tyr Thr Leu
    50                  55                  60

Ser Ser Ser Val Thr Val Thr Ser Asn Thr Trp Pro Ser Gln Thr Ile
65                  70                  75                  80

Thr Cys Asn Val Ala His Pro Ala Ser Ser Thr Lys Val Asp Lys Lys
                85                  90                  95

Ile Glu Pro Arg Val Pro Ile Thr Gln Asn Pro Cys Pro Pro His Gln
            100                 105                 110

Arg Val Pro Pro Cys Ala Ala Pro Asp Leu Leu Gly Gly Pro Ser Val
        115                 120                 125

Phe Ile Phe Pro Pro Lys Ile Lys Asp Val Leu Met Ile Ser Leu Ser
    130                 135                 140

Pro Met Val Thr Cys Val Val Asp Val Ser Glu Asp Asp Pro Asp
145                 150                 155                 160

Val Gln Ile Ser Trp Phe Val Asn Asn Val Glu Val His Thr Ala Gln
                165                 170                 175

Thr Gln Thr His Arg Glu Asp Tyr Asn Ser Thr Leu Arg Val Val Ser
            180                 185                 190

Ala Leu Pro Ile Gln His Gln Asp Trp Met Ser Gly Lys Glu Phe Lys
        195                 200                 205

Cys Lys Val Asn Asn Arg Ala Leu Pro Ser Pro Ile Glu Lys Thr Ile
    210                 215                 220

Ser Lys Pro Arg Gly Pro Val Arg Ala Pro Gln Val Tyr Val Leu Pro
225                 230                 235                 240

Pro Pro Ala Glu Glu Met Thr Lys Lys Glu Phe Ser Leu Thr Cys Met
                245                 250                 255

Ile Thr Gly Phe Leu Pro Ala Glu Ile Ala Val Asp Trp Thr Ser Asn
            260                 265                 270

Gly Arg Thr Glu Gln Asn Tyr Lys Asn Thr Ala Thr Val Leu Asp Ser
        275                 280                 285

Asp Gly Ser Tyr Phe Met Tyr Ser Lys Leu Arg Val Gln Lys Ser Thr
    290                 295                 300

Trp Glu Arg Gly Ser Leu Phe Ala Cys Ser Val Val His Glu Val Leu
305                 310                 315                 320

His Asn His Leu Thr Thr Lys Thr Ile Ser Arg Ser Leu Gly Lys
                325                 330                 335

<210> SEQ ID NO 16
<211> LENGTH: 322
<212> TYPE: PRT
<213> ORGANISM: Rattus norvegicus

<400> SEQUENCE: 16

Ala Glu Thr Thr Ala Pro Ser Val Tyr Pro Leu Ala Pro Gly Thr Ala
```

```
                 1               5                  10                 15
Leu Lys Ser Asn Ser Met Val Thr Leu Gly Cys Leu Val Lys Gly Tyr
                20                 25                 30

Phe Pro Glu Pro Val Thr Val Thr Trp Asn Ser Gly Ala Leu Ser Ser
                35                 40                 45

Gly Val His Thr Phe Pro Ala Val Leu Gln Ser Gly Leu Tyr Thr Leu
                50                 55                 60

Thr Ser Ser Val Thr Val Pro Ser Ser Thr Trp Ser Ser Gln Ala Val
 65                 70                 75                 80

Thr Cys Asn Val Ala His Pro Ala Ser Ser Thr Lys Val Asp Lys Lys
                85                 90                 95

Ile Val Pro Arg Glu Cys Asn Pro Cys Gly Cys Thr Gly Ser Glu Val
                100                105                110

Ser Ser Val Phe Ile Phe Pro Pro Lys Thr Lys Asp Val Leu Thr Ile
                115                120                125

Thr Leu Thr Pro Lys Val Thr Cys Val Val Asp Ile Ser Gln Asn
130                135                140

Asp Pro Glu Val Arg Phe Ser Trp Phe Ile Asp Asp Val Glu Val His
145                150                155                160

Thr Ala Gln Thr His Ala Pro Glu Lys Gln Ser Asn Ser Thr Leu Arg
                165                170                175

Ser Val Ser Glu Leu Pro Ile Val His Arg Asp Trp Leu Asn Gly Lys
                180                185                190

Thr Phe Lys Cys Lys Val Asn Ser Gly Ala Phe Pro Ala Pro Ile Glu
                195                200                205

Lys Ser Ile Ser Lys Pro Glu Gly Thr Pro Arg Gly Pro Gln Val Tyr
                210                215                220

Thr Met Ala Pro Pro Lys Glu Glu Met Thr Gln Ser Gln Val Ser Ile
225                230                235                240

Thr Cys Met Val Lys Gly Phe Tyr Pro Pro Asp Ile Tyr Thr Glu Trp
                245                250                255

Lys Met Asn Gly Gln Pro Gln Glu Asn Tyr Lys Asn Thr Pro Pro Thr
                260                265                270

Met Asp Thr Asp Gly Ser Tyr Phe Leu Tyr Ser Lys Leu Asn Val Lys
                275                280                285

Lys Glu Thr Trp Gln Gln Gly Asn Thr Phe Thr Cys Ser Val Leu His
                290                295                300

Glu Gly Leu His Asn His His Thr Glu Lys Ser Leu Ser His Ser Pro
305                310                315                320

Gly Lys

<210> SEQ ID NO 17
<211> LENGTH: 336
<212> TYPE: PRT
<213> ORGANISM: Mus musculus

<400> SEQUENCE: 17

Ala Lys Thr Thr Pro Pro Ser Val Tyr Pro Leu Ala Pro Gly Cys Gly
 1               5                  10                 15

Asp Thr Thr Gly Ser Ser Val Thr Leu Gly Cys Leu Val Lys Gly Tyr
                20                 25                 30

Phe Pro Glu Ser Val Thr Val Thr Trp Asn Ser Gly Ser Leu Ser Ser
                35                 40                 45

Ser Val His Thr Phe Pro Ala Leu Leu Gln Ser Gly Leu Tyr Thr Met
                50                 55                 60
```

Ser Ser Ser Val Thr Val Pro Ser Ser Thr Trp Pro Ser Gln Thr Val
65                  70                  75                  80

Thr Cys Ser Val Ala His Pro Ala Ser Ser Thr Val Asp Lys Lys
            85                  90                  95

Leu Glu Pro Ser Gly Pro Ile Ser Thr Ile Asn Pro Cys Pro Pro Cys
            100                 105                 110

Lys Glu Cys His Lys Cys Pro Ala Pro Asn Leu Glu Gly Gly Pro Ser
            115                 120                 125

Val Phe Ile Phe Pro Pro Asn Ile Lys Asp Val Leu Met Ile Ser Leu
        130                 135                 140

Thr Pro Lys Val Thr Cys Val Val Asp Val Ser Glu Asp Asp Pro
145                 150                 155                 160

Asp Val Gln Ile Ser Trp Phe Val Asn Asn Val Glu Val His Thr Ala
                165                 170                 175

Gln Thr Gln Thr His Arg Glu Asp Tyr Asn Ser Thr Ile Arg Val Val
            180                 185                 190

Ser Thr Leu Pro Ile Gln His Gln Asp Trp Met Ser Gly Lys Glu Phe
        195                 200                 205

Lys Cys Lys Val Asn Asn Lys Asp Leu Pro Ser Pro Ile Glu Arg Thr
210                 215                 220

Ile Ser Lys Ile Lys Gly Leu Val Arg Ala Pro Gln Val Tyr Ile Leu
225                 230                 235                 240

Pro Pro Pro Ala Glu Gln Leu Ser Arg Lys Asp Val Ser Leu Thr Cys
            245                 250                 255

Leu Val Val Gly Phe Asn Pro Gly Asp Ile Ser Val Glu Trp Thr Ser
            260                 265                 270

Asn Gly His Thr Glu Glu Asn Tyr Lys Asp Thr Ala Pro Val Leu Asp
        275                 280                 285

Ser Asp Gly Ser Tyr Phe Ile Tyr Ser Lys Leu Asn Met Lys Thr Ser
    290                 295                 300

Lys Trp Glu Lys Thr Asp Ser Phe Ser Cys Asn Val Arg His Glu Gly
305                 310                 315                 320

Leu Lys Asn Tyr Tyr Leu Lys Lys Thr Ile Ser Arg Ser Pro Gly Lys
                325                 330                 335

<210> SEQ ID NO 18
<211> LENGTH: 333
<212> TYPE: PRT
<213> ORGANISM: Rattus norvegicus

<400> SEQUENCE: 18

Ala Gln Thr Thr Ala Pro Ser Val Tyr Pro Leu Ala Pro Gly Cys Gly
1               5                   10                  15

Asp Thr Thr Ser Ser Thr Val Thr Leu Gly Cys Leu Val Lys Gly Tyr
            20                  25                  30

Phe Pro Glu Pro Val Thr Val Thr Trp Asn Ser Gly Ala Leu Ser Ser
        35                  40                  45

Asp Val His Thr Phe Pro Ala Val Leu Gln Ser Gly Leu Tyr Thr Leu
    50                  55                  60

Thr Ser Ser Val Thr Ser Ser Thr Trp Pro Ser Gln Thr Val Thr Cys
65                  70                  75                  80

Asn Val Ala His Pro Ala Ser Ser Thr Lys Val Asp Lys Lys Val Glu
            85                  90                  95

Arg Arg Asn Gly Gly Ile Gly His Lys Cys Pro Thr Cys Pro Thr Cys
            100                 105                 110

```
His Lys Cys Pro Val Pro Glu Leu Leu Gly Gly Pro Ser Val Phe Ile
            115                 120                 125

Phe Pro Pro Lys Pro Lys Asp Ile Leu Leu Ile Ser Gln Asn Ala Lys
    130                 135                 140

Val Thr Cys Val Val Asp Val Ser Glu Glu Pro Asp Val Gln
145                 150                 155                 160

Phe Ser Trp Phe Val Asn Asn Val Glu Val His Thr Ala Gln Thr Gln
                165                 170                 175

Pro Arg Glu Glu Gln Tyr Asn Ser Thr Phe Arg Val Val Ser Ala Leu
            180                 185                 190

Pro Ile Gln His Gln Asp Trp Met Ser Gly Lys Glu Phe Lys Cys Lys
        195                 200                 205

Val Asn Asn Lys Ala Leu Pro Ser Pro Ile Glu Lys Thr Ile Ser Lys
    210                 215                 220

Pro Lys Gly Leu Val Arg Lys Pro Gln Val Tyr Val Met Gly Pro Pro
225                 230                 235                 240

Thr Glu Gln Leu Thr Glu Gln Thr Val Ser Leu Thr Cys Leu Thr Ser
                245                 250                 255

Gly Phe Leu Pro Asn Asp Ile Gly Val Glu Trp Thr Ser Asn Gly His
            260                 265                 270

Ile Glu Lys Asn Tyr Lys Asn Thr Glu Pro Val Met Asp Ser Asp Gly
        275                 280                 285

Ser Phe Phe Met Tyr Ser Lys Leu Asn Val Glu Arg Ser Arg Trp Asp
    290                 295                 300

Ser Arg Ala Pro Phe Val Cys Ser Val His Glu Gly Leu His Asn
305                 310                 315                 320

His His Val Glu Lys Ser Ile Ser Arg Pro Gly Lys
                325                 330

<210> SEQ ID NO 19
<211> LENGTH: 329
<212> TYPE: PRT
<213> ORGANISM: Rattus norvegicus

<400> SEQUENCE: 19

Ala Arg Thr Thr Ala Pro Ser Val Tyr Pro Leu Val Pro Gly Cys Ser
1               5                   10                  15

Gly Thr Ser Gly Ser Leu Val Thr Leu Gly Cys Leu Val Lys Gly Tyr
            20                  25                  30

Phe Pro Glu Pro Val Thr Val Lys Trp Asn Ser Gly Ala Leu Ser Ser
        35                  40                  45

Gly Val His Thr Phe Pro Ala Val Leu Gln Ser Gly Leu Tyr Thr Leu
    50                  55                  60

Ser Ser Ser Val Thr Val Pro Ser Ser Thr Trp Ser Ser Gln Thr Val
65                  70                  75                  80

Thr Cys Ser Val Ala His Pro Ala Thr Lys Ser Asn Leu Ile Lys Arg
                85                  90                  95

Ile Glu Pro Arg Arg Pro Lys Pro Arg Pro Thr Asp Ile Cys Ser
            100                 105                 110

Cys Asp Asp Asn Leu Gly Arg Pro Ser Val Phe Ile Phe Pro Pro Lys
        115                 120                 125

Pro Lys Asp Ile Leu Met Ile Thr Leu Thr Pro Lys Val Thr Cys Val
    130                 135                 140

Val Val Asp Val Ser Glu Glu Pro Asp Val Gln Phe Ser Trp Phe
145                 150                 155                 160
```

```
Val Asp Asn Val Arg Val Phe Thr Ala Gln Thr Gln Pro His Glu Glu
            165                 170                 175

Gln Leu Asn Gly Thr Phe Arg Val Val Ser Thr Leu His Ile Gln His
            180                 185                 190

Gln Asp Trp Met Ser Gly Lys Glu Phe Lys Cys Lys Val Asn Asn Lys
            195                 200                 205

Asp Leu Pro Ser Pro Ile Glu Lys Thr Ile Ser Lys Pro Arg Gly Lys
210                 215                 220

Ala Arg Thr Pro Gln Val Tyr Thr Ile Pro Pro Arg Glu Gln Met
225                 230                 235                 240

Ser Lys Asn Lys Val Ser Leu Thr Cys Met Val Thr Ser Phe Tyr Pro
            245                 250                 255

Ala Ser Ile Ser Val Glu Trp Glu Arg Asn Gly Glu Leu Glu Gln Asp
            260                 265                 270

Tyr Lys Asn Thr Leu Pro Val Leu Asp Ser Asp Glu Ser Tyr Phe Leu
            275                 280                 285

Tyr Ser Lys Leu Ser Val Asp Thr Asp Ser Trp Met Arg Gly Asp Ile
            290                 295                 300

Tyr Thr Cys Ser Val Val His Glu Ala Leu His Asn His His Thr Gln
305                 310                 315                 320

Lys Asn Leu Ser Arg Ser Pro Gly Lys
            325

<210> SEQ ID NO 20
<211> LENGTH: 330
<212> TYPE: PRT
<213> ORGANISM: Homo sapiens

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Leu Gly Thr Gln Thr
65                  70                  75                  80

Tyr Ile Cys Asn Val Asn His Lys Pro Ser Asn Thr Lys Val Asp Lys
            85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
            115                 120                 125

Lys Pro Lys Asp Thr Leu Met Ile Ser Arg Thr Pro Glu Val Thr Cys
130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
            165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
            195                 200                 205
```

```
Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 21
<211> LENGTH: 324
<212> TYPE: PRT
<213> ORGANISM: Mus musculus

<400> SEQUENCE: 21

Ala Lys Thr Thr Pro Pro Ser Val Tyr Pro Leu Ala Pro Gly Ser Ala
1               5                   10                  15

Ala Gln Thr Asn Ser Met Val Thr Leu Gly Cys Leu Val Lys Gly Tyr
            20                  25                  30

Phe Pro Glu Pro Val Thr Val Thr Trp Asn Ser Gly Ser Leu Ser Ser
        35                  40                  45

Gly Val His Thr Phe Pro Ala Val Leu Gln Ser Asp Leu Tyr Thr Leu
    50                  55                  60

Ser Ser Ser Val Thr Val Pro Ser Ser Pro Arg Pro Ser Glu Thr Val
65                  70                  75                  80

Thr Cys Asn Val Ala His Pro Ala Ser Ser Thr Lys Val Asp Lys Lys
                85                  90                  95

Ile Val Pro Arg Asp Cys Gly Cys Lys Pro Cys Ile Cys Thr Val Pro
            100                 105                 110

Glu Val Ser Ser Val Phe Ile Phe Pro Pro Lys Pro Lys Asp Val Leu
        115                 120                 125

Thr Ile Thr Leu Thr Pro Lys Val Thr Cys Val Val Val Asp Ile Ser
    130                 135                 140

Lys Asp Asp Pro Glu Val Gln Phe Ser Trp Phe Val Asp Asp Val Glu
145                 150                 155                 160

Val His Thr Ala Gln Thr Gln Pro Arg Glu Glu Gln Phe Asn Ser Thr
                165                 170                 175

Phe Arg Ser Val Ser Glu Leu Pro Ile Met His Gln Asp Trp Leu Asn
            180                 185                 190

Gly Lys Glu Phe Lys Cys Arg Val Asn Ser Ala Ala Phe Pro Ala Pro
        195                 200                 205

Ile Glu Lys Thr Ile Ser Lys Thr Lys Gly Arg Pro Lys Ala Pro Gln
    210                 215                 220

Val Tyr Thr Ile Pro Pro Pro Lys Glu Gln Met Ala Lys Asp Lys Val
225                 230                 235                 240

Ser Leu Thr Cys Met Ile Thr Asp Phe Phe Pro Glu Asp Ile Thr Val
                245                 250                 255
```

```
Glu Trp Gln Trp Asn Gly Gln Pro Ala Glu Asn Tyr Lys Asn Thr Gln
            260                 265                 270
Pro Ile Met Asn Thr Asn Gly Ser Tyr Phe Val Tyr Ser Lys Leu Asn
            275                 280                 285
Val Gln Lys Ser Asn Trp Glu Ala Gly Asn Thr Phe Thr Cys Ser Val
            290                 295                 300
Leu His Glu Gly Leu His Asn His His Thr Glu Lys Ser Leu Ser His
305                 310                 315                 320
Ser Pro Gly Lys

<210> SEQ ID NO 22
<211> LENGTH: 326
<212> TYPE: PRT
<213> ORGANISM: Homo sapiens

<400> SEQUENCE: 22

Ala Ser Thr Lys Gly Pro Ser Val Phe Pro Leu Ala Pro Cys Ser Arg
1               5                   10                  15
Ser Thr Ser Glu Ser Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
            35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Asn Phe Gly Thr Gln Thr
65                  70                  75                  80
Tyr Thr Cys Asn Val Asp His Lys Pro Ser Asn Thr Lys Val Asp Lys
                85                  90                  95
Thr Val Glu Arg Lys Cys Cys Val Glu Cys Pro Pro Cys Pro Ala Pro
            100                 105                 110
Pro Val Ala Gly Pro Ser Val Phe Leu Phe Pro Pro Lys Pro Lys Asp
            115                 120                 125
Thr Leu Met Ile Ser Arg Thr Pro Glu Val Thr Cys Val Val Val Asp
        130                 135                 140
Val Ser His Glu Asp Pro Glu Val Gln Phe Asn Trp Tyr Val Asp Gly
145                 150                 155                 160
Val Glu Val His Asn Ala Lys Thr Lys Pro Arg Glu Glu Gln Phe Asn
                165                 170                 175
Ser Thr Phe Arg Val Val Ser Val Leu Thr Val Val His Gln Asp Trp
            180                 185                 190
Leu Asn Gly Lys Glu Tyr Lys Cys Lys Val Ser Asn Lys Gly Leu Pro
            195                 200                 205
Ala Pro Ile Glu Lys Thr Ile Ser Lys Thr Lys Gly Gln Pro Arg Glu
        210                 215                 220
Pro Gln Val Tyr Thr Leu Pro Pro Ser Arg Glu Glu Met Thr Lys Asn
225                 230                 235                 240
Gln Val Ser Leu Thr Cys Leu Val Lys Gly Phe Tyr Pro Ser Asp Ile
                245                 250                 255
Ala Val Glu Trp Glu Ser Asn Gly Gln Pro Glu Asn Asn Tyr Lys Thr
            260                 265                 270
Thr Pro Pro Met Leu Asp Ser Asp Gly Ser Phe Phe Leu Tyr Ser Lys
            275                 280                 285
Leu Thr Val Asp Lys Ser Arg Trp Gln Gln Gly Asn Val Phe Ser Cys
        290                 295                 300
```

```
Ser Val Met His Glu Ala Leu His Asn His Tyr Thr Gln Lys Ser Leu
305                 310                 315                 320

Ser Leu Ser Pro Gly Lys
                325

<210> SEQ ID NO 23
<211> LENGTH: 290
<212> TYPE: PRT
<213> ORGANISM: Homo sapiens

<400> SEQUENCE: 23

Gln Met Gln Gly Val Asn Cys Thr Val Ser Glu Leu Lys Thr Pro
1               5                   10                  15

Leu Gly Asp Thr Thr His Thr Cys Pro Arg Cys Pro Glu Pro Lys Ser
                20                  25                  30

Cys Asp Thr Pro Pro Cys Pro Arg Cys Pro Glu Pro Lys Ser Cys
        35              40                  45

Asp Thr Pro Pro Cys Pro Arg Cys Pro Glu Pro Lys Ser Cys Asp
    50              55                  60

Thr Pro Pro Pro Cys Pro Arg Cys Pro Ala Pro Glu Leu Leu Gly Gly
65                  70                  75                  80

Pro Ser Val Phe Leu Phe Pro Pro Lys Pro Lys Asp Thr Leu Met Ile
                85                  90                  95

Ser Arg Thr Pro Glu Val Thr Cys Val Val Asp Val Ser His Glu
                100                 105                 110

Asp Pro Glu Val Gln Phe Lys Trp Tyr Val Asp Gly Val Gln Val His
            115                 120                 125

Asn Ala Lys Thr Lys Pro Arg Glu Gln Gln Phe Asn Ser Thr Phe Arg
130                 135                 140

Val Val Ser Val Leu Thr Val Leu His Gln Asn Trp Leu Asp Gly Lys
145                 150                 155                 160

Glu Tyr Lys Cys Lys Val Ser Asn Lys Ala Leu Pro Ala Pro Ile Glu
                165                 170                 175

Lys Thr Ile Ser Lys Thr Lys Gly Gln Pro Arg Glu Pro Gln Val Tyr
            180                 185                 190

Thr Leu Pro Pro Ser Arg Glu Glu Met Thr Lys Asn Gln Val Ser Leu
        195                 200                 205

Thr Cys Leu Val Lys Gly Phe Tyr Pro Ser Asp Ile Ala Val Glu Trp
210                 215                 220

Glu Ser Ser Gly Gln Pro Glu Asn Asn Tyr Asn Thr Thr Pro Pro Met
225                 230                 235                 240

Leu Asp Ser Asp Gly Ser Phe Phe Leu Tyr Ser Lys Leu Thr Val Asp
                245                 250                 255

Lys Ser Arg Trp Gln Gln Gly Asn Ile Phe Ser Cys Ser Val Met His
            260                 265                 270

Glu Ala Leu His Asn Arg Phe Thr Gln Lys Ser Leu Ser Leu Ser Pro
        275                 280                 285

Gly Lys
    290

<210> SEQ ID NO 24
<211> LENGTH: 327
<212> TYPE: PRT
<213> ORGANISM: Homo sapiens

<400> SEQUENCE: 24

Ala Ser Thr Lys Gly Pro Ser Val Phe Pro Leu Ala Pro Cys Ser Arg
```

```
              1               5                  10                 15
Ser Thr Ser Glu Ser Thr Ala Ala Leu Gly Cys Leu Val Lys Asp Tyr
                20                  25                 30

Phe Pro Glu Pro Val Thr Val Ser Trp Asn Ser Gly Ala Leu Thr Ser
                35                  40                 45

Gly Val His Thr Phe Pro Ala Val Leu Gln Ser Ser Gly Leu Tyr Ser
                50                  55                 60

Leu Ser Ser Val Val Thr Val Pro Ser Ser Leu Gly Thr Lys Thr
 65                  70                  75                 80

Tyr Thr Cys Asn Val Asp His Lys Pro Ser Asn Thr Lys Val Asp Lys
                85                  90                 95

Arg Val Glu Ser Lys Tyr Gly Pro Pro Cys Pro Ser Cys Pro Ala Pro
                100                 105                110

Glu Phe Leu Gly Gly Pro Ser Val Phe Leu Phe Pro Pro Lys Pro Lys
                115                 120                125

Asp Thr Leu Met Ile Ser Arg Thr Pro Glu Val Thr Cys Val Val Val
                130                 135                140

Asp Val Ser Gln Glu Asp Pro Glu Val Gln Phe Asn Trp Tyr Val Asp
145                 150                 155                160

Gly Val Glu Val His Asn Ala Lys Thr Lys Pro Arg Glu Glu Gln Phe
                165                 170                175

Asn Ser Thr Tyr Arg Val Val Ser Val Leu Thr Val Leu His Gln Asp
                180                 185                190

Trp Leu Asn Gly Lys Glu Tyr Lys Cys Lys Val Ser Asn Lys Gly Leu
                195                 200                205

Pro Ser Ser Ile Glu Lys Thr Ile Ser Lys Ala Lys Gly Gln Pro Arg
                210                 215                220

Glu Pro Gln Val Tyr Thr Leu Pro Pro Ser Gln Glu Glu Met Thr Lys
225                 230                 235                240

Asn Gln Val Ser Leu Thr Cys Leu Val Lys Gly Phe Tyr Pro Ser Asp
                245                 250                255

Ile Ala Val Glu Trp Glu Ser Asn Gly Gln Pro Glu Asn Asn Tyr Lys
                260                 265                270

Thr Thr Pro Pro Val Leu Asp Ser Asp Gly Ser Phe Phe Leu Tyr Ser
                275                 280                285

Arg Leu Thr Val Asp Lys Ser Arg Trp Gln Gln Gly Asn Val Phe Ser
                290                 295                300

Cys Ser Val Met His Glu Ala Leu His Asn His Tyr Thr Gln Lys Ser
305                 310                 315                320

Leu Ser Leu Ser Leu Gly Lys
                325

<210> SEQ ID NO 25
<211> LENGTH: 227
<212> TYPE: PRT
<213> ORGANISM: Mus musculus

<400> SEQUENCE: 25

Val Pro Arg Asp Cys Gly Cys Lys Pro Cys Ile Cys Thr Val Pro Glu
 1               5                  10                 15

Val Ser Ser Val Phe Ile Phe Pro Pro Lys Pro Lys Asp Val Leu Thr
                20                  25                 30

Ile Thr Leu Thr Pro Lys Val Thr Cys Val Val Val Asp Ile Ser Lys
                35                  40                 45

Asp Asp Pro Glu Val Gln Phe Ser Trp Phe Val Asp Asp Val Glu Val
```

```
                 50                  55                  60
His Thr Ala Gln Thr Lys Pro Arg Glu Glu Phe Asn Ser Thr Phe
 65                  70                  75                  80

Arg Ser Val Ser Glu Leu Pro Ile Met His Gln Asp Trp Leu Asn Gly
                 85                  90                  95

Lys Glu Phe Lys Cys Arg Val Asn Ser Ala Ala Phe Pro Ala Pro Ile
                100                 105                 110

Glu Lys Thr Ile Ser Lys Thr Lys Gly Arg Pro Lys Ala Pro Gln Val
                115                 120                 125

Tyr Thr Ile Pro Pro Pro Lys Glu Gln Met Ala Lys Asp Lys Val Ser
                130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Tyr Ser Lys Leu Asn Val
                180                 185                 190

Gln Lys Ser Asn Trp Glu Ala Gly Asn Thr Phe Thr Cys Ser Val Leu
                195                 200                 205

His Glu Gly Leu His Asn His His Thr Glu Lys Ser Leu Ser His Ser
210                 215                 220

Pro Gly Lys
225

<210> SEQ ID NO 26
<211> LENGTH: 226
<212> TYPE: PRT
<213> ORGANISM: Artificial
<220> FEATURE:
<223> OTHER INFORMATION: Mutant mFc

<400> SEQUENCE: 26

Val Pro Arg Asp Cys Gly Cys Lys Pro Cys Ile Cys Thr Val Pro Glu
 1               5                  10                  15

Val Ser Ser Val Phe Ile Phe Pro Pro Lys Pro Lys Asp Val Leu Thr
                20                  25                  30

Ile Thr Leu Thr Pro Lys Val Thr Cys Val Val Val Asp Ile Ser Lys
                35                  40                  45

Asp Asp Pro Glu Val Gln Phe Ser Trp Phe Val Asp Asp Val Glu Val
 50                  55                  60

His Thr Ala Gln Thr Lys Pro Arg Glu Glu Gln Phe Asn Ser Thr Phe
 65                  70                  75                  80

Arg Ser Val Ser Glu Leu Pro Ile Met His Gln Asp Trp Leu Asn Gly
                85                  90                  95

Lys Glu Phe Lys Cys Arg Val Asn Ser Ala Ala Phe Pro Ala Pro Ile
                100                 105                 110

Glu Lys Thr Ile Ser Lys Thr Lys Gly Arg Pro Lys Ala Pro Gln Val
                115                 120                 125

Tyr Thr Ile Pro Pro Pro Lys Glu Gln Met Ala Lys Asp Lys Val Ser
                130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Lys Thr Asp Gly Ser Tyr Phe Val Tyr Ser Lys Leu Asn Val
                180                 185                 190
```

-continued

```
Gln Lys Ser Asn Trp Glu Ala Gly Asn Thr Phe Thr Cys Ser Val Leu
            195                 200                 205
His Glu Gly Leu His Asn His His Thr Glu Glu Ser Leu Ser His Ser
        210                 215                 220
Pro Gly
225

<210> SEQ ID NO 27
<211> LENGTH: 227
<212> TYPE: PRT
<213> ORGANISM: Artificial
<220> FEATURE:
<223> OTHER INFORMATION: Mutant mFc

<400> SEQUENCE: 27

Val Pro Arg Asp Cys Gly Cys Lys Pro Cys Ile Cys Thr Val Pro Glu
1               5                   10                  15
Val Ser Ser Val Phe Ile Phe Pro Pro Lys Pro Lys Asp Val Leu Thr
            20                  25                  30
Ile Thr Leu Thr Pro Lys Val Thr Cys Val Val Val Asp Ile Ser Lys
        35                  40                  45
Asp Asp Pro Glu Val Gln Phe Ser Trp Phe Val Asp Asp Val Glu Val
    50                  55                  60
His Thr Ala Gln Thr Lys Pro Arg Glu Glu Gln Phe Asn Ser Thr Phe
65                  70                  75                  80
Arg Ser Val Ser Glu Leu Pro Ile Met His Gln Asp Trp Leu Asn Gly
                85                  90                  95
Lys Glu Phe Lys Cys Arg Val Asn Ser Ala Ala Phe Pro Ala Pro Ile
            100                 105                 110
Glu Lys Thr Ile Ser Lys Thr Lys Gly Arg Pro Lys Ala Pro Gln Val
        115                 120                 125
Tyr Thr Ile Pro Pro Pro Lys Glu Gln Met Ala Lys Asp Lys Val Ser
    130                 135                 140
Leu Thr Cys Met Ile Thr Asp Phe Phe Pro Glu Asp Ile Thr Val Glu
145                 150                 155                 160
Trp Gln Trp Asn Gly Gln Pro Ala Glu Asn Tyr Lys Asn Thr Gln Pro
                165                 170                 175
Ile Met Asp Thr Asp Gly Ser Tyr Phe Val Tyr Ser Asp Leu Asn Val
            180                 185                 190
Gln Lys Ser Asn Trp Glu Ala Gly Asn Thr Phe Thr Cys Ser Val Leu
        195                 200                 205
His Glu Gly Leu His Asn His His Thr Glu Lys Ser Leu Ser His Ser
    210                 215                 220
Pro Gly Lys
225

<210> SEQ ID NO 28
<211> LENGTH: 227
<212> TYPE: PRT
<213> ORGANISM: Artificial
<220> FEATURE:
<223> OTHER INFORMATION: Mutant mFc

<400> SEQUENCE: 28

Val Pro Arg Asp Cys Gly Cys Lys Pro Cys Ile Cys Thr Val Pro Glu
1               5                   10                  15
Val Ser Ser Val Phe Ile Phe Pro Pro Lys Pro Lys Asp Val Leu Thr
            20                  25                  30
```

```
Ile Thr Leu Thr Pro Lys Val Thr Cys Val Val Asp Ile Ser Lys
            35                  40                  45

Asp Asp Pro Glu Val Gln Phe Ser Trp Phe Val Asp Asp Val Glu Val
 50                  55                  60

His Thr Ala Gln Thr Lys Pro Arg Glu Glu Gln Phe Asn Ser Thr Phe
 65                  70                  75                  80

Arg Ser Val Ser Glu Leu Pro Ile Met His Gln Asp Trp Leu Asn Gly
                 85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
            115                 120                 125

Tyr Thr Ile Pro Pro Pro Lys Glu Gln Met Ala Lys Asp Lys Val Ser
            130                 135                 140

Leu Thr Cys Met Ile Thr Asp Phe Phe Pro Glu Asp Ile Thr Val Glu
145                 150                 155                 160

Trp Gln Trp Asn Gly Gln Pro Ala Glu Asn Tyr Lys Asn Thr Gln Pro
                165                 170                 175

Ile Met Asp Thr Asp Gly Ser Tyr Phe Val Thr Ser Lys Leu Asn Val
            180                 185                 190

Gln Lys Ser Asn Trp Glu Ala Gly Asn Thr Phe Thr Cys Ser Val Leu
            195                 200                 205

His Glu Gly Leu His Asn His His Thr Glu Lys Ser Leu Ser His Ser
            210                 215                 220

Pro Gly Lys
225

<210> SEQ ID NO 29
<211> LENGTH: 227
<212> TYPE: PRT
<213> ORGANISM: Artificial
<220> FEATURE:
<223> OTHER INFORMATION: Mutant mFc

<400> SEQUENCE: 29

Val Pro Arg Asp Cys Gly Cys Lys Pro Cys Ile Cys Thr Val Pro Glu
1                5                  10                  15

Val Ser Ser Val Phe Ile Phe Pro Pro Lys Pro Lys Asp Val Leu Thr
             20                  25                  30

Ile Thr Leu Thr Pro Lys Val Thr Cys Val Val Asp Ile Ser Lys
            35                  40                  45

Asp Asp Pro Glu Val Gln Phe Ser Trp Phe Val Asp Asp Val Glu Val
 50                  55                  60

His Thr Ala Gln Thr Lys Pro Arg Glu Glu Gln Phe Asn Ser Thr Phe
 65                  70                  75                  80

Arg Ser Val Ser Glu Leu Pro Ile Met His Gln Asp Trp Leu Asn Gly
                 85                  90                  95

Lys Glu Phe Lys Cys Arg Val Asn Ser Ala Ala Phe Pro Ala Pro Ile
            100                 105                 110

Glu Lys Thr Ile Ser Lys Thr Lys Gly Arg Pro Lys Ala Pro Gln Val
            115                 120                 125

Tyr Thr Ile Pro Pro Pro Lys Glu Gln Met Ala Lys Asp Lys Val Ser
            130                 135                 140

Leu Tyr Cys Met Ile Thr Asp Phe Phe Pro Glu Asp Ile Thr Val Glu
145                 150                 155                 160
```

```
Trp Gln Trp Asn Gly Gln Pro Ala Glu Asn Tyr Lys Asn Thr Gln Pro
            165                 170                 175

Ile Met Asp Thr Asp Gly Ser Tyr Phe Val Tyr Ser Lys Leu Asn Val
        180                 185                 190

Gln Lys Ser Asn Trp Glu Ala Gly Asn Thr Phe Thr Cys Ser Val Leu
        195                 200                 205

His Glu Gly Leu His Asn His His Thr Glu Lys Ser Leu Ser His Ser
    210                 215                 220

Pro Gly Lys
225

<210> SEQ ID NO 30
<211> LENGTH: 18
<212> TYPE: PRT
<213> ORGANISM: Artificial
<220> FEATURE:
<223> OTHER INFORMATION: Signal sequence

<400> SEQUENCE: 30

Met Pro Leu Leu Leu Leu Leu Pro Leu Leu Trp Ala Gly Ala Leu Ala
1               5                   10                  15

Met Asp

<210> SEQ ID NO 31
<211> LENGTH: 382
<212> TYPE: PRT
<213> ORGANISM: Artificial
<220> FEATURE:
<223> OTHER INFORMATION: Fusion protein

<400> SEQUENCE: 31

Met Pro Leu Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
            20                  25                  30

Pro Glu Val Ser Ser Val Phe Ile Phe Pro Pro Lys Pro Lys Asp Val
        35                  40                  45

Leu Thr Ile Thr Leu Thr Pro Lys Val Thr Cys Val Val Val Asp Ile
    50                  55                  60

Ser Lys Asp Asp Pro Glu Val Gln Phe Ser Trp Phe Val Asp Asp Val
65                  70                  75                  80

Glu Val His Thr Ala Gln Thr Lys Pro Arg Glu Glu Gln Phe Asn Ser
                85                  90                  95

Thr Phe Arg Ser Val Ser Glu Leu Pro Ile Met His Gln Asp Trp Leu
            100                 105                 110

Asn Gly Lys Glu Phe Lys Cys Arg Val Asn Ser Ala Ala Phe Pro Ala
        115                 120                 125

Pro Ile Glu Lys Thr Ile Ser Lys Thr Lys Gly Arg Pro Lys Ala Pro
    130                 135                 140

Gln Val Tyr Thr Ile Pro Pro Lys Glu Gln Met Ala Lys Asp Lys
145                 150                 155                 160

Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
            180                 185                 190

Gln Pro Ile Met Asp Thr Asp Gly Ser Tyr Phe Val Tyr Ser Lys Leu
        195                 200                 205

Asn Val Gln Lys Ser Asn Trp Glu Ala Gly Asn Thr Phe Thr Cys Ser
```

```
                 210                 215                 220
Val Leu His Glu Gly Leu His Asn His Thr Glu Lys Ser Leu Ser
225                 230                 235                 240

His Ser Pro Gly Lys Gly Ser Gln Arg His Asn Asn Ser Ser Leu Asn
                245                 250                 255

Thr Arg Thr Gln Lys Ala Arg His Cys Gly His Cys Pro Glu Glu Trp
                260                 265                 270

Ile Thr Tyr Ser Asn Ser Cys Tyr Tyr Ile Gly Lys Glu Arg Arg Thr
                275                 280                 285

Trp Glu Glu Ser Leu Leu Ala Cys Thr Ser Lys Asn Ser Ser Leu Leu
290                 295                 300

Ser Ile Asp Asn Glu Glu Glu Met Lys Phe Leu Ser Ile Ile Ser Pro
305                 310                 315                 320

Ser Ser Trp Ile Gly Val Phe Arg Asn Ser Ser His His Pro Trp Val
                325                 330                 335

Thr Met Asn Gly Leu Ala Phe Lys His Glu Ile Lys Asp Ser Asp Asn
                340                 345                 350

Ala Glu Leu Asn Cys Ala Val Leu Gln Val Asn Arg Leu Lys Ser Ala
                355                 360                 365

Gln Cys Gly Ser Ser Ile Ile Tyr His Cys Lys His Lys Leu
                370                 375                 380

<210> SEQ ID NO 32
<211> LENGTH: 393
<212> TYPE: PRT
<213> ORGANISM: Artificial
<220> FEATURE:
<223> OTHER INFORMATION: Fusion protein

<400> SEQUENCE: 32

Met Pro Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
                20                  25                  30

Pro Glu Val Ser Ser Val Phe Ile Phe Pro Pro Lys Pro Lys Asp Val
                35                  40                  45

Leu Thr Ile Thr Leu Thr Pro Lys Val Thr Cys Val Val Val Asp Ile
                50                  55                  60

Ser Lys Asp Asp Pro Glu Val Gln Phe Ser Trp Phe Val Asp Asp Val
65                  70                  75                  80

Glu Val His Thr Ala Gln Thr Lys Pro Arg Glu Glu Gln Phe Asn Ser
                85                  90                  95

Thr Phe Arg Ser Val Ser Glu Leu Pro Ile Met His Gln Asp Trp Leu
                100                 105                 110

Asn Gly Lys Glu Phe Lys Cys Arg Val Asn Ser Ala Ala Phe Pro Ala
                115                 120                 125

Pro Ile Glu Lys Thr Ile Ser Lys Thr Lys Gly Arg Pro Lys Ala Pro
130                 135                 140

Gln Val Tyr Thr Ile Pro Pro Pro Lys Glu Gln Met Ala Lys Asp Lys
145                 150                 155                 160

Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
                180                 185                 190

Gln Pro Ile Met Asp Thr Asp Gly Ser Tyr Phe Val Tyr Ser Lys Leu
                195                 200                 205
```

```
Asn Val Gln Lys Ser Asn Trp Glu Ala Gly Asn Thr Phe Thr Cys Ser
    210                 215                 220
Val Leu His Glu Gly Leu His Asn His His Thr Glu Lys Ser Leu Ser
225                 230                 235                 240
His Ser Pro Gly Lys Gly Ser Ser Phe Thr Lys Leu Ser Ile Glu Pro
                245                 250                 255
Ala Phe Thr Pro Gly Pro Asn Ile Glu Leu Gln Lys Asp Ser Asp Cys
                260                 265                 270
Cys Ser Cys Gln Glu Lys Trp Val Gly Tyr Arg Cys Asn Cys Tyr Phe
            275                 280                 285
Ile Ser Ser Glu Gln Lys Thr Trp Asn Glu Ser Arg His Leu Cys Ala
        290                 295                 300
Ser Gln Lys Ser Ser Leu Leu Gln Leu Gln Asn Thr Asp Glu Leu Asp
305                 310                 315                 320
Phe Met Ser Ser Ser Gln Gln Phe Tyr Trp Ile Gly Leu Ser Tyr Ser
                325                 330                 335
Glu Glu His Thr Ala Trp Leu Trp Glu Asn Gly Ser Ala Leu Ser Gln
                340                 345                 350
Tyr Leu Phe Pro Ser Phe Glu Thr Phe Asn Thr Lys Asn Cys Ile Ala
            355                 360                 365
Tyr Asn Pro Asn Gly Asn Ala Leu Asp Glu Ser Cys Glu Asp Lys Asn
        370                 375                 380
Arg Tyr Ile Cys Lys Gln Gln Leu Ile
385                 390

<210> SEQ ID NO 33
<211> LENGTH: 393
<212> TYPE: PRT
<213> ORGANISM: Artificial
<220> FEATURE:
<223> OTHER INFORMATION: Fusion protein

<400> SEQUENCE: 33

Met Pro Leu Leu Leu Leu Pro Leu Leu Trp Ala Gly Ala Leu Ala
1               5                   10                  15
Met Asp Val Pro Arg Asp Cys Gly Cys Lys Pro Cys Ile Cys Thr Val
                20                  25                  30
Pro Glu Val Ser Ser Val Phe Ile Phe Pro Pro Lys Pro Lys Asp Val
                35                  40                  45
Leu Thr Ile Thr Leu Thr Pro Lys Val Thr Cys Val Val Val Asp Ile
            50                  55                  60
Ser Lys Asp Asp Pro Glu Val Gln Phe Ser Trp Phe Val Asp Asp Val
65                  70                  75                  80
Glu Val His Thr Ala Gln Thr Lys Pro Arg Glu Glu Gln Phe Asn Ser
                85                  90                  95
Thr Phe Arg Ser Val Ser Glu Leu Pro Ile Met His Gln Asp Trp Leu
                100                 105                 110
Asn Gly Lys Glu Phe Lys Cys Arg Val Asn Ser Ala Ala Phe Pro Ala
            115                 120                 125
Pro Ile Glu Lys Thr Ile Ser Lys Thr Lys Gly Arg Pro Lys Ala Pro
        130                 135                 140
Gln Val Tyr Thr Ile Pro Pro Pro Lys Glu Gln Met Ala Lys Asp Lys
145                 150                 155                 160
Val Ser Leu Tyr Cys Met Ile Thr Asp Phe Phe Pro Glu Asp Ile Thr
                165                 170                 175
```

```
Val Glu Trp Gln Trp Asn Gly Gln Pro Ala Glu Asn Tyr Lys Asn Thr
            180                 185                 190

Gln Pro Ile Met Asp Thr Asp Gly Ser Tyr Phe Val Tyr Ser Lys Leu
            195                 200                 205

Asn Val Gln Lys Ser Asn Trp Glu Ala Gly Asn Thr Phe Thr Cys Ser
            210                 215                 220

Val Leu His Glu Gly Leu His Asn His His Thr Lys Ser Leu Ser
225             230                 235                 240

His Ser Pro Gly Lys Gly Ser Ser Phe Thr Lys Leu Ser Ile Glu Pro
            245                 250                 255

Ala Phe Thr Pro Gly Pro Asn Ile Glu Leu Gln Lys Asp Ser Asp Cys
            260                 265                 270

Cys Ser Cys Gln Glu Lys Trp Val Gly Tyr Arg Cys Asn Cys Tyr Phe
            275                 280                 285

Ile Ser Ser Glu Gln Lys Thr Trp Asn Glu Ser Arg His Leu Cys Ala
            290                 295                 300

Ser Gln Lys Ser Ser Leu Leu Gln Leu Gln Asn Thr Asp Glu Leu Asp
305             310                 315                 320

Phe Met Ser Ser Ser Gln Gln Phe Tyr Trp Ile Gly Leu Ser Tyr Ser
            325                 330                 335

Glu Glu His Thr Ala Trp Leu Trp Glu Asn Gly Ser Ala Leu Ser Gln
            340                 345                 350

Tyr Leu Phe Pro Ser Phe Glu Thr Phe Asn Thr Lys Asn Cys Ile Ala
            355                 360                 365

Tyr Asn Pro Asn Gly Asn Ala Leu Asp Glu Ser Cys Glu Asp Lys Asn
            370                 375                 380

Arg Tyr Ile Cys Lys Gln Gln Leu Ile
385             390

<210> SEQ ID NO 34
<211> LENGTH: 382
<212> TYPE: PRT
<213> ORGANISM: Artificial
<220> FEATURE:
<223> OTHER INFORMATION: Fusion protein

<400> SEQUENCE: 34

Met Pro Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
            20                  25                  30

Pro Glu Val Ser Ser Val Phe Ile Phe Pro Pro Lys Pro Lys Asp Val
            35                  40                  45

Leu Thr Ile Thr Leu Thr Pro Lys Val Thr Cys Val Val Val Asp Ile
        50                  55                  60

Ser Lys Asp Asp Pro Glu Val Gln Phe Ser Trp Phe Val Asp Asp Val
65              70                  75                  80

Glu Val His Thr Ala Gln Thr Lys Pro Arg Glu Glu Gln Phe Asn Ser
            85                  90                  95

Thr Phe Arg Ser Val Ser Glu Leu Pro Ile Met His Gln Asp Trp Leu
            100                 105                 110

Asn Gly Lys Glu Phe Lys Cys Arg Val Asn Ser Ala Ala Phe Pro Ala
            115                 120                 125

Pro Ile Glu Lys Thr Ile Ser Lys Thr Lys Gly Arg Pro Lys Ala Pro
            130                 135                 140

Gln Val Tyr Thr Ile Pro Pro Pro Lys Glu Gln Met Ala Lys Asp Lys
```

```
145                 150                 155                 160
Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
                180                 185                 190

Gln Pro Ile Met Asp Thr Asp Gly Ser Tyr Phe Val Thr Ser Lys Leu
                195                 200                 205

Asn Val Gln Lys Ser Asn Trp Glu Ala Gly Asn Thr Phe Thr Cys Ser
    210                 215                 220

Val Leu His Glu Gly Leu His Asn His His Thr Glu Lys Ser Leu Ser
225                 230                 235                 240

His Ser Pro Gly Lys Gly Ser Gln Arg His Asn Asn Ser Ser Leu Asn
                245                 250                 255

Thr Arg Thr Gln Lys Ala Arg His Cys Gly His Cys Pro Glu Glu Trp
                260                 265                 270

Ile Thr Tyr Ser Asn Ser Cys Tyr Tyr Ile Gly Lys Glu Arg Arg Thr
                275                 280                 285

Trp Glu Glu Ser Leu Leu Ala Cys Thr Ser Lys Asn Ser Ser Leu Leu
                290                 295                 300

Ser Ile Asp Asn Glu Glu Glu Met Lys Phe Leu Ser Ile Ile Ser Pro
305                 310                 315                 320

Ser Ser Trp Ile Gly Val Phe Arg Asn Ser Ser His His Pro Trp Val
                325                 330                 335

Thr Met Asn Gly Leu Ala Phe Lys His Glu Ile Lys Asp Ser Asp Asn
                340                 345                 350

Ala Glu Leu Asn Cys Ala Val Leu Gln Val Asn Arg Leu Lys Ser Ala
                355                 360                 365

Gln Cys Gly Ser Ser Ile Ile Tyr His Cys Lys His Lys Leu
                370                 375                 380

<210> SEQ ID NO 35
<211> LENGTH: 393
<212> TYPE: PRT
<213> ORGANISM: Artificial
<220> FEATURE:
<223> OTHER INFORMATION: Fusion protein

<400> SEQUENCE: 35

Met Pro Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
                20                  25                  30

Pro Glu Val Ser Ser Val Phe Ile Phe Pro Pro Lys Pro Lys Asp Val
                35                  40                  45

Leu Thr Ile Thr Leu Thr Pro Lys Val Thr Cys Val Val Val Asp Ile
                50                  55                  60

Ser Lys Asp Asp Pro Glu Val Gln Phe Ser Trp Phe Val Asp Asp Val
65                  70                  75                  80

Glu Val His Thr Ala Gln Thr Lys Pro Arg Glu Glu Gln Phe Asn Ser
                85                  90                  95

Thr Phe Arg Ser Val Ser Glu Leu Pro Ile Met His Gln Asp Trp Leu
                100                 105                 110

Asn Gly Lys Glu Phe Lys Cys Arg Val Asn Ser Ala Ala Phe Pro Ala
                115                 120                 125

Pro Ile Glu Lys Thr Ile Ser Lys Thr Lys Gly Arg Pro Lys Ala Pro
                130                 135                 140
```

```
Gln Val Tyr Thr Ile Pro Pro Lys Lys Gln Met Ala Lys Asp Lys
145                 150                 155                 160

Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
            180                 185                 190

Gln Pro Ile Met Asp Thr Asp Gly Ser Tyr Phe Val Tyr Ser Asp Leu
        195                 200                 205

Asn Val Gln Lys Ser Asn Trp Glu Ala Gly Asn Thr Phe Thr Cys Ser
    210                 215                 220

Val Leu His Glu Gly Leu His Asn His His Thr Glu Lys Ser Leu Ser
225                 230                 235                 240

His Ser Pro Gly Lys Gly Ser Ser Phe Thr Lys Leu Ser Ile Glu Pro
                245                 250                 255

Ala Phe Thr Pro Gly Pro Asn Ile Glu Leu Gln Lys Asp Ser Asp Cys
            260                 265                 270

Cys Ser Cys Gln Glu Lys Trp Val Gly Tyr Arg Cys Asn Cys Tyr Phe
        275                 280                 285

Ile Ser Ser Glu Gln Lys Thr Trp Asn Glu Ser Arg His Leu Cys Ala
    290                 295                 300

Ser Gln Lys Ser Ser Leu Leu Gln Leu Gln Asn Thr Asp Glu Leu Asp
305                 310                 315                 320

Phe Met Ser Ser Ser Gln Gln Phe Tyr Trp Ile Gly Leu Ser Tyr Ser
                325                 330                 335

Glu Glu His Thr Ala Trp Leu Trp Glu Asn Gly Ser Ala Leu Ser Gln
            340                 345                 350

Tyr Leu Phe Pro Ser Phe Glu Thr Phe Asn Thr Lys Asn Cys Ile Ala
        355                 360                 365

Tyr Asn Pro Asn Gly Asn Ala Leu Asp Glu Ser Cys Glu Asp Lys Asn
    370                 375                 380

Arg Tyr Ile Cys Lys Gln Gln Leu Ile
385                 390

<210> SEQ ID NO 36
<211> LENGTH: 382
<212> TYPE: PRT
<213> ORGANISM: Artificial
<220> FEATURE:
<223> OTHER INFORMATION: Fusion protein

<400> SEQUENCE: 36

Met Pro Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
            20                  25                  30

Pro Glu Val Ser Ser Val Phe Ile Phe Pro Pro Lys Pro Lys Asp Val
        35                  40                  45

Leu Thr Ile Thr Leu Thr Pro Lys Val Thr Cys Val Val Val Asp Ile
    50                  55                  60

Ser Lys Asp Asp Pro Glu Val Gln Phe Ser Trp Phe Val Asp Asp Val
65                  70                  75                  80

Glu Val His Thr Ala Gln Thr Lys Pro Arg Glu Glu Gln Phe Asn Ser
                85                  90                  95

Thr Phe Arg Ser Val Ser Glu Leu Pro Ile Met His Gln Asp Trp Leu
            100                 105                 110
```

```
Asn Gly Lys Glu Phe Lys Cys Arg Val Asn Ser Ala Ala Phe Pro Ala
            115                 120                 125

Pro Ile Glu Lys Thr Ile Ser Lys Thr Lys Gly Arg Pro Lys Ala Pro
        130                 135                 140

Gln Val Tyr Thr Ile Pro Pro Lys Glu Gln Met Ala Lys Asp Lys
145                 150                 155                 160

Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
            180                 185                 190

Gln Pro Ile Met Lys Thr Asp Gly Ser Tyr Phe Val Tyr Ser Lys Leu
        195                 200                 205

Asn Val Gln Lys Ser Asn Trp Glu Ala Gly Asn Thr Phe Thr Cys Ser
210                 215                 220

Val Leu His Glu Gly Leu His Asn His His Thr Glu Glu Ser Leu Ser
225                 230                 235                 240

His Ser Pro Gly Lys Gly Ser Gln Arg His Asn Asn Ser Ser Leu Asn
                245                 250                 255

Thr Arg Thr Gln Lys Ala Arg His Cys Gly His Cys Pro Glu Glu Trp
            260                 265                 270

Ile Thr Tyr Ser Asn Ser Cys Tyr Tyr Ile Gly Lys Glu Arg Arg Thr
        275                 280                 285

Trp Glu Glu Ser Leu Leu Ala Cys Thr Ser Lys Asn Ser Ser Leu Leu
290                 295                 300

Ser Ile Asp Asn Glu Glu Glu Met Lys Phe Leu Ser Ile Ile Ser Pro
305                 310                 315                 320

Ser Ser Trp Ile Gly Val Phe Arg Asn Ser Ser His His Pro Trp Val
                325                 330                 335

Thr Met Asn Gly Leu Ala Phe Lys His Glu Ile Lys Asp Ser Asp Asn
            340                 345                 350

Ala Glu Leu Asn Cys Ala Val Leu Gln Val Asn Arg Leu Lys Ser Ala
        355                 360                 365

Gln Cys Gly Ser Ser Ile Ile Tyr His Cys Lys His Lys Leu
370                 375                 380

<210> SEQ ID NO 37
<211> LENGTH: 537
<212> TYPE: PRT
<213> ORGANISM: Artificial
<220> FEATURE:
<223> OTHER INFORMATION: Fusion protein

<400> SEQUENCE: 37

Met Gly Ser Ser His His His His His His Ser Ser Gly Leu Val Pro
1               5                   10                  15

Arg Gly Ser His Met Leu Glu Ser Pro Ile Leu Gly Tyr Trp Lys Ile
            20                  25                  30

Lys Gly Leu Val Gln Pro Thr Arg Leu Leu Leu Glu Tyr Leu Glu Glu
        35                  40                  45

Lys Tyr Glu Glu His Leu Tyr Glu Arg Asp Glu Gly Asp Lys Trp Arg
    50                  55                  60

Asn Lys Lys Phe Glu Leu Gly Leu Glu Phe Pro Asn Leu Pro Tyr Tyr
65                  70                  75                  80

Ile Asp Gly Asp Val Lys Leu Thr Gln Ser Met Ala Ile Ile Arg Tyr
                85                  90                  95

Ile Ala Asp Lys His Asn Met Leu Gly Gly Cys Pro Lys Glu Arg Ala
```

```
                100              105                110
Glu Ile Ser Met Leu Glu Gly Ala Val Leu Asp Ile Arg Tyr Gly Val
        115                 120                125

Ser Arg Ile Ala Tyr Ser Lys Asp Phe Glu Thr Leu Lys Val Asp Phe
    130                 135                 140

Leu Ser Lys Leu Pro Glu Met Leu Lys Met Phe Glu Asp Arg Leu Cys
145                 150                 155                 160

His Lys Thr Tyr Leu Asn Gly Asp His Val Thr His Pro Asp Phe Met
                165                 170                 175

Leu Tyr Asp Ala Leu Asp Val Val Leu Tyr Met Asp Pro Met Cys Leu
                180                 185                 190

Asp Ala Phe Pro Lys Leu Val Cys Phe Lys Lys Arg Ile Glu Ala Ile
            195                 200                 205

Pro Gln Ile Asp Lys Tyr Leu Lys Ser Ser Lys Tyr Ile Ala Trp Pro
            210                 215                 220

Leu Gln Gly Trp Gln Ala Thr Phe Gly Gly Asp His Pro Lys
225                 230                 235                 240

Ser Asp Leu Val Pro Arg Gly Ser Gln Arg His Asn Asn Ser Ser Leu
                245                 250                 255

Asn Thr Arg Thr Gln Lys Ala Arg His Cys Gly His Cys Pro Glu Glu
            260                 265                 270

Trp Ile Thr Tyr Ser Asn Ser Cys Tyr Tyr Ile Gly Lys Glu Arg Arg
                275                 280                 285

Thr Trp Glu Glu Ser Leu Leu Ala Cys Thr Ser Lys Asn Ser Ser Leu
        290                 295                 300

Leu Ser Ile Asp Asn Glu Glu Met Lys Phe Leu Ser Ile Ile Ser
305                 310                 315                 320

Pro Ser Ser Trp Ile Gly Val Phe Arg Asn Ser Ser His His Pro Trp
                325                 330                 335

Val Thr Met Asn Gly Leu Ala Phe Lys His Glu Ile Lys Asp Ser Asp
            340                 345                 350

Asn Ala Glu Leu Asn Cys Ala Val Leu Gln Val Asn Arg Leu Lys Ser
            355                 360                 365

Ala Gln Cys Gly Ser Ser Ile Ile Tyr His Cys Lys His Lys Leu Gly
    370                 375                 380

Gly Ser Gly Gly Ser Arg Ser Ser Phe Thr Lys Leu Ser Ile Glu Pro
385                 390                 395                 400

Ala Phe Thr Pro Gly Pro Asn Ile Glu Leu Gln Lys Asp Ser Asp Cys
                405                 410                 415

Cys Ser Cys Gln Glu Lys Trp Val Gly Tyr Arg Cys Asn Cys Tyr Phe
                420                 425                 430

Ile Ser Ser Glu Gln Lys Thr Trp Asn Glu Ser Arg His Leu Cys Ala
        435                 440                 445

Ser Gln Lys Ser Ser Leu Leu Gln Leu Gln Asn Thr Asp Glu Leu Asp
        450                 455                 460

Phe Met Ser Ser Ser Gln Gln Phe Tyr Trp Ile Gly Leu Ser Tyr Ser
465                 470                 475                 480

Glu Glu His Thr Ala Trp Leu Trp Glu Asn Gly Ser Ala Leu Ser Gln
                485                 490                 495

Tyr Leu Phe Pro Ser Phe Glu Thr Phe Asn Thr Lys Asn Cys Ile Ala
            500                 505                 510

Tyr Asn Pro Asn Gly Asn Ala Leu Asp Glu Ser Cys Glu Asp Lys Asn
            515                 520                 525
```

Arg Tyr Ile Cys Lys Gln Gln Leu Ile
    530                 535

<210> SEQ ID NO 38
<211> LENGTH: 454
<212> TYPE: PRT
<213> ORGANISM: Artificial
<220> FEATURE:
<223> OTHER INFORMATION: Fusion protein

<400> SEQUENCE: 38

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
    50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
            100                 105                 110

Ser Gly His Met His His His His His His Ser Ser Gly Leu Val Pro
        115                 120                 125

Arg Gly Ser Gly Met Lys Glu Thr Ala Ala Ala Lys Phe Glu Arg Gln
    130                 135                 140

His Met Asp Ser Pro Asp Leu Gly Thr Asp Asp Asp Lys Ala Met Ala
145                 150                 155                 160

Ala Asp Ile Gly Ser Gln Arg His Asn Asn Ser Ser Leu Asn Thr Arg
                165                 170                 175

Thr Gln Lys Ala Arg His Cys Gly His Cys Pro Glu Glu Trp Ile Thr
            180                 185                 190

Tyr Ser Asn Ser Cys Tyr Tyr Ile Gly Lys Glu Arg Arg Thr Trp Glu
        195                 200                 205

Glu Ser Leu Leu Ala Cys Thr Ser Lys Asn Ser Ser Leu Leu Ser Ile
    210                 215                 220

Asp Asn Glu Glu Glu Met Lys Phe Leu Ser Ile Ile Ser Pro Ser Ser
225                 230                 235                 240

Trp Ile Gly Val Phe Arg Asn Ser Ser His His Pro Trp Val Thr Met
                245                 250                 255

Asn Gly Leu Ala Phe Lys His Glu Ile Lys Asp Ser Asp Asn Ala Glu
            260                 265                 270

Leu Asn Cys Ala Val Leu Gln Val Asn Arg Leu Lys Ser Ala Gln Cys
        275                 280                 285

Gly Ser Ser Ile Ile Tyr His Cys Lys His Lys Leu Gly Gly Ser Gly
    290                 295                 300

Gly Ser Arg Ser Ser Phe Thr Lys Leu Ser Ile Glu Pro Ala Phe Thr
305                 310                 315                 320

Pro Gly Pro Asn Ile Glu Leu Gln Lys Asp Ser Asp Cys Cys Ser Cys
                325                 330                 335

Gln Glu Lys Trp Val Gly Tyr Arg Cys Asn Cys Tyr Phe Ile Ser Ser
            340                 345                 350

Glu Gln Lys Thr Trp Asn Glu Ser Arg His Leu Cys Ala Ser Gln Lys

```
                355                 360                 365
Ser Ser Leu Leu Gln Leu Gln Asn Thr Asp Glu Leu Asp Phe Met Ser
    370                 375                 380

Ser Ser Gln Gln Phe Tyr Trp Ile Gly Leu Ser Tyr Ser Glu Glu His
385                 390                 395                 400

Thr Ala Trp Leu Trp Glu Asn Gly Ser Ala Leu Ser Gln Tyr Leu Phe
                405                 410                 415

Pro Ser Phe Glu Thr Phe Asn Thr Lys Asn Cys Ile Ala Tyr Asn Pro
                420                 425                 430

Asn Gly Asn Ala Leu Asp Glu Ser Cys Glu Asp Lys Asn Arg Tyr Ile
            435                 440                 445

Cys Lys Gln Gln Leu Ile
        450

<210> SEQ ID NO 39
<211> LENGTH: 536
<212> TYPE: PRT
<213> ORGANISM: Artificial
<220> FEATURE:
<223> OTHER INFORMATION: Fusion protein

<400> SEQUENCE: 39

Met Pro Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
                20                  25                  30

Pro Glu Val Ser Ser Val Phe Ile Phe Pro Pro Lys Pro Lys Asp Val
                35                  40                  45

Leu Thr Ile Thr Leu Thr Pro Lys Val Thr Cys Val Val Val Asp Ile
            50                  55                  60

Ser Lys Asp Asp Pro Glu Val Gln Phe Ser Trp Phe Val Asp Asp Val
65                  70                  75                  80

Glu Val His Thr Ala Gln Thr Lys Pro Arg Glu Gln Phe Asn Ser
                85                  90                  95

Thr Phe Arg Ser Val Ser Glu Leu Pro Ile Met His Gln Asp Trp Leu
                100                 105                 110

Asn Gly Lys Glu Phe Lys Cys Arg Val Asn Ser Ala Ala Phe Pro Ala
            115                 120                 125

Pro Ile Glu Lys Thr Ile Ser Lys Thr Lys Gly Arg Pro Lys Ala Pro
    130                 135                 140

Gln Val Tyr Thr Ile Pro Pro Pro Lys Glu Gln Met Ala Lys Asp Lys
145                 150                 155                 160

Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
                180                 185                 190

Gln Pro Ile Met Asp Thr Asp Gly Ser Tyr Phe Val Tyr Ser Lys Leu
            195                 200                 205

Asn Val Gln Lys Ser Asn Trp Glu Ala Gly Asn Thr Phe Thr Cys Ser
    210                 215                 220

Val Leu His Glu Gly Leu His Asn His His Thr Glu Lys Ser Leu Ser
225                 230                 235                 240

His Ser Pro Gly Lys Gly Ser Gln Arg His Asn Asn Ser Ser Leu Asn
                245                 250                 255

Thr Arg Thr Gln Lys Ala Arg His Cys Gly His Cys Pro Glu Glu Trp
                260                 265                 270
```

Ile Thr Tyr Ser Asn Ser Cys Tyr Tyr Ile Gly Lys Glu Arg Arg Thr
            275                 280                 285

Trp Glu Glu Ser Leu Leu Ala Cys Thr Ser Lys Asn Ser Ser Leu Leu
    290                 295                 300

Ser Ile Asp Asn Glu Glu Met Lys Phe Leu Ser Ile Ile Ser Pro
305                 310                 315                 320

Ser Ser Trp Ile Gly Val Phe Arg Asn Ser Ser His His Pro Trp Val
                325                 330                 335

Thr Met Asn Gly Leu Ala Phe Lys His Glu Ile Lys Asp Ser Asp Asn
                340                 345                 350

Ala Glu Leu Asn Cys Ala Val Leu Gln Val Asn Arg Leu Lys Ser Ala
            355                 360                 365

Gln Cys Gly Ser Ser Ile Ile Tyr His Cys Lys His Lys Leu Gly Gly
            370                 375                 380

Ser Gly Gly Ser Arg Ser Ser Phe Thr Lys Leu Ser Ile Glu Pro Ala
385                 390                 395                 400

Phe Thr Pro Gly Pro Asn Ile Glu Leu Gln Lys Asp Ser Asp Cys Cys
                405                 410                 415

Ser Cys Gln Glu Lys Trp Val Gly Tyr Arg Cys Asn Cys Tyr Phe Ile
            420                 425                 430

Ser Ser Glu Gln Lys Thr Trp Asn Glu Ser Arg His Leu Cys Ala Ser
            435                 440                 445

Gln Lys Ser Ser Leu Leu Gln Leu Gln Asn Thr Asp Glu Leu Asp Phe
450                 455                 460

Met Ser Ser Ser Gln Gln Phe Tyr Trp Ile Gly Leu Ser Tyr Ser Glu
465                 470                 475                 480

Glu His Thr Ala Trp Leu Trp Glu Asn Gly Ser Ala Leu Ser Gln Tyr
                485                 490                 495

Leu Phe Pro Ser Phe Glu Thr Phe Asn Thr Lys Asn Cys Ile Ala Tyr
            500                 505                 510

Asn Pro Asn Gly Asn Ala Leu Asp Glu Ser Cys Glu Asp Lys Asn Arg
        515                 520                 525

Tyr Ile Cys Lys Gln Gln Leu Ile
    530                 535

<210> SEQ ID NO 40
<211> LENGTH: 35
<212> TYPE: DNA
<213> ORGANISM: Artificial
<220> FEATURE:
<223> OTHER INFORMATION: Primer

<400> SEQUENCE: 40
ggatcctctt ttactaaact gagtattgag ccagc                           35

<210> SEQ ID NO 41
<211> LENGTH: 45
<212> TYPE: DNA
<213> ORGANISM: Artificial
<220> FEATURE:
<223> OTHER INFORMATION: Primer

<400> SEQUENCE: 41
gcggccgcag atctattaaa tgagctgttg cttacagata taacg                45

<210> SEQ ID NO 42
<211> LENGTH: 30
<212> TYPE: DNA

```
<213> ORGANISM: Artificial
<220> FEATURE:
<223> OTHER INFORMATION: Primer

<400> SEQUENCE: 42
ggatcccaga ggcacaacaa ttcttccctg                                        30

<210> SEQ ID NO 43
<211> LENGTH: 36
<212> TYPE: DNA
<213> ORGANISM: Artificial
<220> FEATURE:
<223> OTHER INFORMATION: Primer

<400> SEQUENCE: 43
gcggccgcag atctattaaa gcttatgctt acaatg                                 36

<210> SEQ ID NO 44
<211> LENGTH: 80
<212> TYPE: DNA
<213> ORGANISM: Artificial
<220> FEATURE:
<223> OTHER INFORMATION: Primer

<400> SEQUENCE: 44
gctagcatgc cgctgctgct actgctgccc ctgctgtggg cagggcccct ggctatggat       60
gtgcccaggg attgtggttg                                                   80

<210> SEQ ID NO 45
<211> LENGTH: 29
<212> TYPE: DNA
<213> ORGANISM: Artificial
<220> FEATURE:
<223> OTHER INFORMATION: Primer

<400> SEQUENCE: 45 ggatcctttta ccaggagagt gggagaggc                                        29

<210> SEQ ID NO 46
<211> LENGTH: 43
<212> TYPE: DNA
<213> ORGANISM: Artificial
<220> FEATURE:
<223> OTHER INFORMATION: Primer

<400> SEQUENCE: 46
ggccaaggat aaagtcagtc tgtactgcat gataacagac ttc                         43

<210> SEQ ID NO 47
<211> LENGTH: 43
<212> TYPE: DNA
<213> ORGANISM: Artificial
<220> FEATURE:
<223> OTHER INFORMATION: Primer

<400> SEQUENCE: 47
gaagtctgtt atcatgcagt acagactgac tttatccttg gcc                         43

<210> SEQ ID NO 48
<211> LENGTH: 44
<212> TYPE: DNA
<213> ORGANISM: Artificial
<220> FEATURE:
<223> OTHER INFORMATION: Primer

<400> SEQUENCE: 48
```
cagatggctc ttacttcgtc accagcaagc tcaatgtgca gaag 44

<210> SEQ ID NO 49
<211> LENGTH: 44
<212> TYPE: DNA
<213> ORGANISM: Artificial
<220> FEATURE:
<223> OTHER INFORMATION: Primer

<400> SEQUENCE: 49
cttctgcaca ttgagcttgc tggtgacgaa gtaagagcca tctg 44

<210> SEQ ID NO 50
<211> LENGTH: 33
<212> TYPE: DNA
<213> ORGANISM: Artificial
<220> FEATURE:
<223> OTHER INFORMATION: Primer

<400> SEQUENCE: 50
ccattccacc tcccaagaag cagatggcca agg 33

<210> SEQ ID NO 51
<211> LENGTH: 44
<212> TYPE: DNA
<213> ORGANISM: Artificial
<220> FEATURE:
<223> OTHER INFORMATION: Primer

<400> SEQUENCE: 51
gctcttactt cgtctacagc gacctcaatg tgcagaagag caac 44

<210> SEQ ID NO 52
<211> LENGTH: 41
<212> TYPE: DNA
<213> ORGANISM: Artificial
<220> FEATURE:
<223> OTHER INFORMATION: Primer

<400> SEQUENCE: 52
gaacactcag cccatcatga agacagatgg ctcttacttc g 41

<210> SEQ ID NO 53
<211> LENGTH: 36
<212> TYPE: DNA
<213> ORGANISM: Artificial
<220> FEATURE:
<223> OTHER INFORMATION: Primer

<400> SEQUENCE: 53
ccaccatact gaggagagcc tctcccactc tcctgg 36

<210> SEQ ID NO 54
<211> LENGTH: 300
<212> TYPE: PRT
<213> ORGANISM: Artificial
<220> FEATURE:
<223> OTHER INFORMATION: Fusion protein

<400> SEQUENCE: 54

Met Ser Asp Lys Ile Ile His Leu Thr Asp Asp Ser Phe Asp Thr Asp
1               5                   10                  15

Val Leu Lys Ala Asp Gly Ala Ile Leu Val Asp Phe Trp Ala Glu Trp
            20                  25                  30

Cys Gly Pro Cys Lys Met Ile Ala Pro Ile Leu Asp Glu Ile Ala Asp
        35                  40                  45

Glu Tyr Gln Gly Lys Leu Thr Val Ala Lys Leu Asn Ile Asp Gln Asn
        50                  55                  60

Pro Gly Thr Ala Pro Lys Tyr Gly Ile Arg Gly Ile Pro Thr Leu Leu
65                  70                  75                  80

Leu Phe Lys Asn Gly Glu Val Ala Ala Thr Lys Val Gly Ala Leu Ser
                85                  90                  95

Lys Gly Gln Leu Lys Glu Phe Leu Asp Ala Asn Leu Ala Gly Ser Gly
                100                 105                 110

Ser Gly His Met His His His His His Ser Ser Gly Leu Val Pro
                115                 120                 125

Arg Gly Ser Gly Met Lys Glu Thr Ala Ala Ala Lys Phe Glu Arg Gln
        130                 135                 140

His Met Asp Ser Pro Asp Leu Gly Thr Asp Asp Asp Lys Ala Met
145                 150                 155                 160

Ala Asp Ile Gly Ser Gln Arg His Asn Asn Ser Ser Leu Asn Thr Arg
                165                 170                 175

Thr Gln Lys Ala Arg His Cys Gly His Cys Pro Glu Glu Trp Ile Thr
        180                 185                 190

Tyr Ser Asn Ser Cys Tyr Tyr Ile Gly Lys Glu Arg Arg Thr Trp Glu
                195                 200                 205

Glu Ser Leu Leu Ala Cys Thr Ser Lys Asn Ser Ser Leu Leu Ser Ile
        210                 215                 220

Asp Asn Glu Glu Glu Met Lys Phe Leu Ser Ile Ile Ser Pro Ser Ser
225                 230                 235                 240

Trp Ile Gly Val Phe Arg Asn Ser Ser His His Pro Trp Val Thr Met
                245                 250                 255

Asn Gly Leu Ala Phe Lys His Glu Ile Lys Asp Ser Asp Asn Ala Glu
                260                 265                 270

Leu Asn Cys Ala Val Leu Gln Val Asn Arg Leu Lys Ser Ala Gln Cys
        275                 280                 285

Gly Ser Ser Ile Ile Tyr His Cys Lys His Lys Leu
        290                 295                 300

<210> SEQ ID NO 55
<211> LENGTH: 394
<212> TYPE: PRT
<213> ORGANISM: Artificial
<220> FEATURE:
<223> OTHER INFORMATION: Fusion protein

<400> SEQUENCE: 55

Met Gly Ser Ser His His His His His His Ser Ser Gly Leu Val Pro
1               5                   10                  15

Arg Gly Ser His Met Leu Glu Ser Pro Ile Leu Gly Tyr Trp Lys Ile
                20                  25                  30

Lys Gly Leu Val Gln Pro Thr Arg Leu Leu Leu Glu Tyr Leu Glu Glu
        35                  40                  45

Lys Tyr Glu Glu His Leu Tyr Glu Arg Asp Glu Gly Asp Lys Trp Arg
    50                  55                  60

Asn Lys Lys Phe Glu Leu Gly Leu Glu Phe Pro Asn Leu Pro Tyr Tyr
65                  70                  75                  80

Ile Asp Gly Asp Val Lys Leu Thr Gln Ser Met Ala Ile Ile Arg Tyr
                85                  90                  95

Ile Ala Asp Lys His Asn Met Leu Gly Gly Cys Pro Lys Glu Arg Ala
                100                 105                 110

```
Glu Ile Ser Met Leu Glu Gly Ala Val Leu Asp Ile Arg Tyr Gly Val
        115                 120                 125

Ser Arg Ile Ala Tyr Ser Lys Asp Phe Glu Thr Leu Lys Val Asp Phe
    130                 135                 140

Leu Ser Lys Leu Pro Glu Met Leu Lys Met Phe Glu Asp Arg Leu Cys
145                 150                 155                 160

His Lys Thr Tyr Leu Asn Gly Asp His Val Thr His Pro Asp Phe Met
                165                 170                 175

Leu Tyr Asp Ala Leu Asp Val Val Leu Tyr Met Asp Pro Met Cys Leu
            180                 185                 190

Asp Ala Phe Pro Lys Leu Val Cys Phe Lys Lys Arg Ile Glu Ala Ile
        195                 200                 205

Pro Gln Ile Asp Lys Tyr Leu Lys Ser Ser Lys Tyr Ile Ala Trp Pro
    210                 215                 220

Leu Gln Gly Trp Gln Ala Thr Phe Gly Gly Asp His Pro Pro Lys
225                 230                 235                 240

Ser Asp Leu Val Pro Arg Gly Ser Ser Phe Thr Lys Leu Ser Ile Glu
                245                 250                 255

Pro Ala Phe Thr Pro Gly Pro Asn Ile Glu Leu Gln Lys Asp Ser Asp
            260                 265                 270

Cys Cys Ser Cys Gln Glu Lys Trp Val Gly Tyr Arg Cys Asn Cys Tyr
        275                 280                 285

Phe Ile Ser Ser Glu Gly Lys Thr Trp Asn Glu Ser Arg His Leu Cys
290                 295                 300

Ala Ser Gln Lys Ser Ser Leu Leu Gln Leu Gln Asn Thr Asp Glu Leu
305                 310                 315                 320

Asp Phe Met Ser Ser Gln Gln Phe Tyr Trp Ile Gly Leu Ser Tyr
                325                 330                 335

Ser Glu Glu His Thr Ala Trp Leu Trp Glu Asn Gly Ser Ala Leu Ser
                340                 345                 350

Gln Tyr Leu Phe Pro Ser Phe Glu Thr Phe Asn Thr Lys Asn Cys Ile
            355                 360                 365

Ala Tyr Asn Pro Asn Gly Asn Ala Leu Asp Glu Ser Cys Glu Asp Lys
        370                 375                 380

Asn Arg Tyr Ile Cys Lys Gln Gln Leu Ile
385                 390
```

<210> SEQ ID NO 56
<211> LENGTH: 24
<212> TYPE: DNA
<213> ORGANISM: Artificial
<220> FEATURE:
<223> OTHER INFORMATION: Primer

<400> SEQUENCE: 56
agcttggcgg tagcggcggt agca          24

<210> SEQ ID NO 57
<211> LENGTH: 24
<212> TYPE: DNA
<213> ORGANISM: Artificial
<220> FEATURE:
<223> OTHER INFORMATION: Primer

<400> SEQUENCE: 57
gatctgctac cgccgctacc gcca          24

<210> SEQ ID NO 58

-continued

```
<211> LENGTH: 43
<212> TYPE: DNA
<213> ORGANISM: Artificial
<220> FEATURE:
<223> OTHER INFORMATION: Primer

<400> SEQUENCE: 58
gttgtgcctc tggctaccgc cgctaccgcc aatgagctgt tgc          43

<210> SEQ ID NO 59
<211> LENGTH: 537
<212> TYPE: PRT
<213> ORGANISM: Artificial
<220> FEATURE:
<223> OTHER INFORMATION: Fusion protein

<400> SEQUENCE: 59
```

Met Pro Leu Leu Leu Leu Pro Leu Leu Trp Ala Gly Ala Leu Ala
1               5                   10                  15

Met Asp Val Pro Arg Asp Cys Gly Cys Lys Pro Cys Ile Cys Thr Val
            20                  25                  30

Pro Glu Val Ser Ser Val Phe Ile Phe Pro Pro Lys Pro Lys Asp Val
        35                  40                  45

Leu Thr Ile Thr Leu Thr Pro Lys Val Thr Cys Val Val Asp Ile
    50                  55                  60

Ser Lys Asp Asp Pro Glu Val Gln Phe Ser Trp Phe Val Asp Asp Val
65                  70                  75                  80

Glu Val His Thr Ala Gln Thr Lys Pro Arg Glu Glu Gln Phe Asn Ser
                85                  90                  95

Thr Phe Arg Ser Val Ser Glu Leu Pro Ile Met His Gln Asp Trp Leu
            100                 105                 110

Asn Gly Lys Glu Phe Lys Cys Arg Val Asn Ser Ala Ala Phe Pro Ala
        115                 120                 125

Pro Ile Glu Lys Thr Ile Ser Lys Thr Lys Gly Arg Pro Lys Ala Pro
    130                 135                 140

Gln Val Tyr Thr Ile Pro Pro Pro Lys Glu Gln Met Ala Lys Asp Lys
145                 150                 155                 160

Val Ser Leu Thr Cys Met Ile Thr Asp Phe Phe Pro Glu Asp Ile Thr
                165                 170                 175

Val Glu Trp Gln Trp Asn Gly Gln Pro Ala Glu Asn Tyr Lys Asn Thr
            180                 185                 190

Gln Pro Ile Met Asp Thr Asp Gly Ser Tyr Phe Val Tyr Ser Lys Leu
        195                 200                 205

Asn Val Gln Lys Ser Asn Trp Glu Ala Gly Asn Thr Phe Thr Cys Ser
    210                 215                 220

Val Leu His Glu Gly Leu His Asn His His Thr Glu Lys Ser Leu Ser
225                 230                 235                 240

His Ser Pro Gly Lys Gly Ser Phe Leu Glu Asn Asn Ser Ser Pro
                245                 250                 255

Asn Thr Arg Thr Gln Lys Ala Arg His Cys Gly His Cys Pro Glu Glu
            260                 265                 270

Trp Ile Thr Tyr Ser Asn Ser Cys Tyr Tyr Ile Gly Lys Glu Arg Arg
        275                 280                 285

Thr Trp Glu Glu Ser Leu Leu Ala Cys Thr Ser Lys Asn Ser Ser Leu
    290                 295                 300

Leu Ser Ile Asp Asn Glu Glu Glu Met Lys Phe Leu Ala Ser Ile Leu
305                 310                 315                 320

```
Pro Ser Ser Trp Ile Gly Val Phe Arg Asn Ser Ser His His Pro Trp
                325                 330                 335
Val Thr Ile Asn Gly Leu Ala Phe Lys His Lys Ile Lys Asp Ser Asp
            340                 345                 350
Asn Ala Glu Leu Asn Cys Ala Val Leu Gln Val Asn Arg Leu Lys Ser
        355                 360                 365
Ala Gln Cys Gly Ser Ser Met Ile Tyr His Cys Lys His Lys Leu Gly
    370                 375                 380
Gly Ser Gly Gly Ser Arg Ser Ser Phe Thr Lys Leu Ser Ile Glu Pro
385                 390                 395                 400
Ala Phe Thr Pro Gly Pro Asn Ile Glu Leu Gln Lys Asp Ser Asp Cys
                405                 410                 415
Cys Ser Cys Gln Glu Lys Trp Val Gly Tyr Arg Cys Asn Cys Tyr Phe
            420                 425                 430
Ile Ser Ser Glu Gln Lys Thr Trp Asn Glu Ser Arg His Leu Cys Ala
        435                 440                 445
Ser Gln Lys Ser Ser Leu Leu Gln Leu Gln Asn Thr Asp Glu Leu Asp
    450                 455                 460
Phe Met Ser Ser Ser Gln Gln Phe Tyr Trp Ile Gly Leu Ser Tyr Ser
465                 470                 475                 480
Glu Glu His Thr Ala Trp Leu Trp Glu Asn Gly Ser Ala Leu Ser Gln
                485                 490                 495
Tyr Leu Phe Pro Ser Phe Glu Thr Phe Asn Thr Lys Asn Cys Ile Ala
            500                 505                 510
Tyr Asn Pro Asn Gly Asn Ala Leu Asp Glu Ser Cys Glu Asp Lys Asn
        515                 520                 525
Arg Tyr Ile Cys Lys Gln Gln Leu Ile
    530                 535

<210> SEQ ID NO 60
<211> LENGTH: 50
<212> TYPE: DNA
<213> ORGANISM: Artificial
<220> FEATURE:
<223> OTHER INFORMATION: Primer

<400> SEQUENCE: 60
gtaaaggatc cctggagcag aacaattctt ccctaatac aagaactcag          50

<210> SEQ ID NO 61
<211> LENGTH: 50
<212> TYPE: DNA
<213> ORGANISM: Artificial
<220> FEATURE:
<223> OTHER INFORMATION: Primer

<400> SEQUENCE: 61
ctgagttctt gtattagggg aagaattgtt ctgctccagg gatcctttac           50

<210> SEQ ID NO 62
<211> LENGTH: 44
<212> TYPE: DNA
<213> ORGANISM: Artificial
<220> FEATURE:
<223> OTHER INFORMATION: Primer

<400> SEQUENCE: 62
atgaaatttc tggcttccat tttgccatcc tcatggattg gtgt                 44

<210> SEQ ID NO 63
```

```
<211> LENGTH: 45
<212> TYPE: DNA
<213> ORGANISM: Artificial
<220> FEATURE:
<223> OTHER INFORMATION: Primer

<400> SEQUENCE: 63
ccatgaggat ggcaaaatgg aagccagaaa tttcatttct tcttc            45

<210> SEQ ID NO 64
<211> LENGTH: 45
<212> TYPE: DNA
<213> ORGANISM: Artificial
<220> FEATURE:
<223> OTHER INFORMATION: Primer

<400> SEQUENCE: 64
catcatccat gggtgacaat aaatggtttg gctttcaaac atgag            45

<210> SEQ ID NO 65
<211> LENGTH: 45
<212> TYPE: DNA
<213> ORGANISM: Artificial
<220> FEATURE:
<223> OTHER INFORMATION: Primer

<400> SEQUENCE: 65
ctcatgtttg aaagccaaac catttattgt cacccatgga tgatg            45

<210> SEQ ID NO 66
<211> LENGTH: 51
<212> TYPE: DNA
<213> ORGANISM: Artificial
<220> FEATURE:
<223> OTHER INFORMATION: Primer

<400> SEQUENCE: 66
ggctttcaaa cataaaataa aagactcaga taatgctgaa cttaactgtg c      51

<210> SEQ ID NO 67
<211> LENGTH: 51
<212> TYPE: DNA
<213> ORGANISM: Artificial
<220> FEATURE:
<223> OTHER INFORMATION: Primer

<400> SEQUENCE: 67
ctgagtcttt tattttatgt ttgaaagcca aaccattcat tgtcacccat g      51

<210> SEQ ID NO 68
<211> LENGTH: 50
<212> TYPE: DNA
<213> ORGANISM: Artificial
<220> FEATURE:
<223> OTHER INFORMATION: Primer

<400> SEQUENCE: 68
gcccagtgtg gatcttcaat gatatatcat tgtaagcata agcttggcgg        50

<210> SEQ ID NO 69
<211> LENGTH: 50
<212> TYPE: DNA
<213> ORGANISM: Artificial
<220> FEATURE:
<223> OTHER INFORMATION: Primer
```

```
<400> SEQUENCE: 69
ccgccaagct tatgcttaca atgatatatc attgaagatc cacactgggc                50
```